US010912794B2

(12) United States Patent
Horst et al.

(10) Patent No.: US 10,912,794 B2
(45) Date of Patent: Feb. 9, 2021

(54) USE OF BETA-1,3-GLUCAN FOR MODULATING IMMUNE FUNCTION AND TREATING INTESTINAL INFLAMMATION

(71) Applicant: ALGAL SCIENTIFIC CORPORATION, Plymouth, MI (US)

(72) Inventors: Geoffrey Paul Horst, Pointe Farms, MI (US); Robert Bernard Levine, Ann Arbor, MI (US)

(73) Assignee: KEMIN INDUSTRIES, INC., Des Moines, IA (US)

(*) Notice: Subject to any disclaimer, the term of this patent is extended or adjusted under 35 U.S.C. 154(b) by 0 days.

(21) Appl. No.: 15/771,809

(22) PCT Filed: Oct. 27, 2016

(86) PCT No.: PCT/US2016/059192
§ 371 (c)(1),
(2) Date: Apr. 27, 2018

(87) PCT Pub. No.: WO2017/075262
PCT Pub. Date: May 4, 2017

(65) Prior Publication Data
US 2018/0311271 A1    Nov. 1, 2018

Related U.S. Application Data

(60) Provisional application No. 62/305,875, filed on Mar. 9, 2016, provisional application No. 62/247,629, filed on Oct. 28, 2015.

(51) Int. Cl.
| | |
|---|---|
| *A61K 31/716* | (2006.01) |
| *A61K 35/68* | (2006.01) |
| *A61K 45/06* | (2006.01) |
| *A61P 39/00* | (2006.01) |
| *A61P 1/00* | (2006.01) |
| *A61P 3/00* | (2006.01) |
| *A61P 3/06* | (2006.01) |
| *A61P 31/04* | (2006.01) |
| *A61P 37/04* | (2006.01) |
| *A23L 33/125* | (2016.01) |
| *A61K 9/14* | (2006.01) |
| *A61K 33/30* | (2006.01) |
| *A61K 39/39* | (2006.01) |
| *A61K 39/00* | (2006.01) |

(52) U.S. Cl.
CPC .......... *A61K 31/716* (2013.01); *A23L 33/125* (2016.08); *A61K 9/14* (2013.01); *A61K 33/30* (2013.01); *A61K 35/68* (2013.01); *A61K 39/39* (2013.01); *A61K 45/06* (2013.01); *A61P 1/00* (2018.01); *A61P 3/00* (2018.01); *A61P 3/06* (2018.01); *A61P 31/04* (2018.01); *A61P 37/04* (2018.01); *A61P 39/00* (2018.01); *A23V 2002/00* (2013.01); *A61K 2039/55583* (2013.01)

(58) Field of Classification Search
None
See application file for complete search history.

(56) References Cited

U.S. PATENT DOCUMENTS

| | | | |
|---|---|---|---|
| 2004/0138172 A1 | 7/2004 | Murata et al. | |
| 2005/0271613 A1 | 12/2005 | Suzuki et al. | |
| 2009/0181925 A1 | 7/2009 | Liu et al. | |
| 2011/0008476 A1 | 1/2011 | Johansen et al. | |
| 2011/0158932 A1* | 6/2011 | Jiang .................. | A61K 31/4375 424/78.16 |
| 2013/0216586 A1 | 8/2013 | LeBrun et al. | |
| 2015/0181909 A1 | 7/2015 | Levine et al. | |
| 2017/0020939 A1 | 1/2017 | Nakashima et al. | |

FOREIGN PATENT DOCUMENTS

| | | |
|---|---|---|
| JP | 2009062337 A | 3/2009 |
| JP | 2011178700 A | 9/2011 |
| JP | 2013075869 A | 4/2013 |
| JP | 2014118374 A | 6/2014 |
| WO | 2009063221 A2 | 5/2009 |
| WO | 2013126669 A | 8/2013 |
| WO | 2013169768 A1 | 11/2013 |
| WO | 2015156339 A1 | 4/2017 |

OTHER PUBLICATIONS

Watanabe et al., "Antitumor activity of the B-glucan paramylon from Euglena against preneoplastic colonic aberrant crypt foci in mice," Journal of Food and Function, Aug. 2013, pp. 1685-1690.
Shimada et al., "Oral administration of green algae, *Euglena gracilis*, inhibits hyperglycemia in OLETF rats, a model of spontaneous type 2 diabetes," Journal of Food and Function, Oct. 2016, pp. 4655-4659.
International Bureau, "Search Report and Written Opinion," issued in connection with International Patent Application No. PCT/US2016/059192, dated Jan. 3, 2017, 8 pages.
International Bureau, "International Preliminary Report on Patentability," issued in connection with International Patent Application No. PCT/US2016/059192, dated May 11, 2018, 7 pages.

* cited by examiner

*Primary Examiner* — Patricia Duffy
*Assistant Examiner* — Garen Gotfredson
(74) *Attorney, Agent, or Firm* — Nyemaster Goode P.C.

(57) ABSTRACT

The present application relates to beta-1,3-glucan and uses thereof to modulate immunity in the human body. Also provided are methods for treatment and/or prevention of high cholesterol, diabetes, and allergies. Also provided are methods for treatment and/or prevention of intestinal inflammation.

25 Claims, 28 Drawing Sheets

1A

1B

4A

4B

9A

9B

10A

10B

11A

11B

12A

12B

12C

18A

18B

19A

19B

USE OF BETA-1,3-GLUCAN FOR MODULATING IMMUNE FUNCTION AND TREATING INTESTINAL INFLAMMATION

CROSS-REFERENCE TO RELATED APPLICATIONS

This application claims the benefit of U.S. Provisional Application No. 62/247,629, filed Oct. 28, 2015 and U.S. Provisional Application No. 62/305,875, filed Mar. 9, 2016; the contents of each of which are incorporated herein by reference in their entirety.

FIELD OF THE INVENTION

The present application relates to beta-1,3-glucan and uses thereof to modulate immunity in the human body. Also provided are methods for treatment and/or prevention of high cholesterol, diabetes, and allergies. The present application also relates to beta-1,3-glucan and uses thereof to enhance the immune function of a human having intestinal inflammation. Also provided are methods for treatment and/or prevention of intestinal inflammation.

BACKGROUND OF THE INVENTION

Beta glucans are polymers of D-glucose linked by beta-glycosidic bonds produced by a variety of organisms including yeast, fungi, bacteria, algae, oats, barley, and kelp. Different organisms produce beta glucans with differing branching structures, average molecular weights, solubility, and/or tertiary structure. For example, beta glucan derived from yeast is generally insoluble and has both beta-1,3- and 1,6-glycosidic bonds (beta-1,3-/1,6-glucan). On the other hand, beta glucan derived from oats is typically more soluble and has both beta-1,3- and 1,4-glycosidic bonds (beta-1,3-/1,4-glucan). In contrast, beta glucan derived from algae such as *Euglena* has almost exclusively 1,3-glycosidic bonds and no 1,6-glycosidic bonds. The specific glycosidic linkages of the various beta glucan forms affect the properties of these molecules.

Some beta glucans have been identified as having beneficial health properties. As beta glucan is typically associated with the surface of pathogenic microorganisms, the immune system of higher organisms has evolved to recognize beta glucan and to mount an immune response. For example, it has been shown that beta glucan derived from yeast can impact immune function by binding complement receptor 3 or dectin-1 on macrophages (see Brown et al., *Journal of Experimental Medicine*, vol. 196(3), pp. 407-412 (2002)). At the physiological level, beta glucan interacts with cell surface receptors to initiate a cascade of events including phagocytosis and the production of certain cytokines. By introducing certain beta glucans, the immune system can be primed so that its response to an actual disease challenge is more robust.

Modulation of the immune function in an individual to combat disease represents an alternative to the administration of conventional medicines. A modulated immune function may effectively treat a disease in an individual, or may prevent the onset of disease in an individual. Also, modulation or enhancement of the immune function in an individual to combat disease represents an alternative to the administration of conventional medicines. A modulated or enhanced immune function may effectively treat a disease in an individual, or may prevent the onset of disease in an individual. Many conventional medicines cause undesirable side effects in patients. Furthermore, antibiotic-resistant strains of bacteria pose an ever-increasing health risk. As such, there is a need for alternative disease treatment that has fewer, if any, side effects. There is also a need for more natural methods to prevent the onset of disease.

Whereas beta glucans derived from yeast and oats have been extensively studied, the health benefits arising from beta-1,3-glucan derived from algae, such as *Euglena*, have received less attention. Described herein are methods of modulating immune function in an individual by administering beta-1,3-glucan derived from *Euglena*. Certain diseases can be treated and/or prevented by modulating the immune function of an individual.

Current treatments of intestinal inflammation include changes in diet and/or lifestyle, medication, and surgery. However, there is a need for more effective treatments of intestinal inflammation, as well as for treatments that have fewer, if any, side effects. Described herein are methods of enhancing immune function in an individual having intestinal inflammation by administering beta-1,3-glucan derived from *Euglena*.

SUMMARY OF THE INVENTION

The present disclosure provides a method of treating a condition selected from the group consisting of hyperlipidemia, metabolic syndrome, inflammatory bowel disease, colitis, Crohn's disease, and colon cancer in a human with said condition, the method comprising orally administering to the human an effective amount of a composition comprising beta-1,3-glucan from *Euglena* grown using fermentation. In certain embodiments, the condition is selected from the group consisting of hyperlipidemia, metabolic syndrome, inflammatory bowel disease, colitis, and Crohn's disease.

In certain embodiments, the condition is hyperlipidemia. In certain embodiments, the administration of the composition reduces the level of cholesterol in the human. In certain embodiments, the effective amount of the composition comprises between 0.1 mg beta-1,3-glucan/kg body weight and 100 mg beta-1,3-glucan/kg body weight. In certain embodiments, the effective amount of the composition comprises between 0.1 mg beta-1,3-glucan/kg body weight and 50 mg beta-1,3-glucan/kg body weight. In certain embodiments, the composition is administered in combination with statins, nicotinic acid, bile acid resins, fibric acid derivatives, or cholesterol absorption inhibitors.

In certain embodiments, the condition is selected from the group consisting of inflammatory bowel disease, colitis, Crohn's disease, and colon cancer. In certain embodiments, the condition is selected from the group consisting of inflammatory bowel disease, colitis, and Crohn's disease. In certain embodiments, the condition is colitis. In certain embodiments, the condition is inflammatory bowel disease. In certain embodiments, the condition is Crohn's disease. In certain embodiments, the condition is colon cancer. In certain embodiments, the effective amount of the composition comprises between 0.1 mg beta-1,3-glucan/kg body weight and 100 mg beta-1,3-glucan/kg body weight. In certain embodiments, administering the composition increases anti-inflammatory cytokine production. In certain embodiments, the composition is administered in combination with anti-inflammatory drugs, immunosuppression drugs, or antibiotics.

In certain embodiments, the *Euglena* is *Euglena gracilis*. In certain embodiments, the *Euglena* is heterotrophically grown. In certain embodiments, the beta-1,3-glucan is in the form of paramylon. In certain embodiments, the beta-1,3-glucan does not contain beta-1,6-glycosidic bonds. In certain embodiments, the beta-1,3-glucan is purified from *Euglena*. In certain embodiments, the composition comprises *Euglena* biomass, the *Euglena* biomass comprising the beta-1,3-glucan. In certain embodiments, the *Euglena* biomass is dried to a moisture content of about 40% or less. In certain embodiments, the *Euglena* biomass has been further processed to have an average particle size of 1000 microns or less.

In certain embodiments, the composition is administered daily as a single dose. In certain embodiments, the composition is administered as multiple separate doses in a single day.

In certain embodiments, the composition further comprises an additional component selected from the group consisting of alpha tocopherol, cholecalciferol, zinc, chromium, selenium, arginine, ascorbic acid, alkylglycerol, caffeine, kava kava, *Curcuma longa, Spirulina, Chlorella, stevia*, calcium D-glucarate, coenzyme Q10, peptides, dimethylglycine, docosahexaenoic acid, eicosapentaenoic acid, alpha-lineolenic acid, astaxanthin, beta carotene, lutein, *lactobacillus* probiotics, *bifidobacterium* probiotics, mannoligosaccharide, fructooligosaccharides, *Astragalus, Echinacea*, Esberitox, garlic, glutathione, kelp, L-arginine, L-ornithine, lecithin granules, extracts from maiitake, reishi or shiitake mushrooms, manganese, quercetin, bromelain, Olive Leaf, *Sambucus*, Umcka, panthothenic acid, quercetin, alpha lipoic acid, essential oils, fish oils, spices and their derivatives, pterostilbene, and combinations thereof. In certain embodiments, the additional component is zinc.

In certain embodiments, the composition further comprises a metal. In certain embodiments, the metal comprises a member selected from the group consisting of iron, magnesium, lithium, zinc, copper, chromium, nickel, cobalt, vanadium, molybdenum, manganese, selenium, and combinations thereof. In certain embodiments, the beta-(1,3)-glucan and the metal form a complex. In certain embodiments, the complex comprises a zinc beta-(1,3)-glucan complex.

In certain embodiments, the composition further comprises an additional component selected from the group consisting of *Haematococcus pluvialis*, astaxanthin, and colostrum.

In certain embodiments, the composition is administered as a solid. In certain embodiments, the composition is administered as a suspension.

The present disclosure provides that the methods disclosed herein can also be adapted to the corresponding uses.

The present disclosure provides a composition comprising beta-1,3-glucan from *Euglena* grown using fermentation for use in the treatment of a condition selected from the group consisting of hyperlipidemia, metabolic syndrome, inflammatory bowel disease, colitis, Crohn's disease, and colon cancer. In certain embodiments, the condition is selected from the group consisting of hyperlipidemia, metabolic syndrome, inflammatory bowel disease, colitis, and Crohn's disease.

The present disclosure provides use of a composition comprising beta-1,3-glucan from *Euglena* grown using fermentation for the manufacture of a medicament for the treatment of a condition selected from the group consisting of hyperlipidemia, metabolic syndrome, inflammatory bowel disease, colitis, Crohn's disease, and colon cancer. In certain embodiments, the condition is selected from the group consisting of hyperlipidemia, metabolic syndrome, inflammatory bowel disease, colitis, and Crohn's disease.

In one aspect, the application discloses a method of modulating the immune function in a human in need thereof comprising orally administering to the human an effective amount of a composition comprising beta-1,3-glucan derived from *Euglena* grown using fermentation.

In some embodiments, the effective daily amount of the composition is between 0.1 mg beta-1,3-glucan/kg body weight and 50 mg beta-1,3-glucan/kg body weight.

In some embodiments, administration of the composition modulates an autoimmune response, blood sugar level, an infection, or inflammation. In one embodiment, the inflammation is associated with allergies. In another embodiment, the autoimmune response is associated with diabetes. In another embodiment, the infection is a bacterial, fungal, or viral infection.

In some embodiments, the *Euglena* is heterotrophically grown. In one embodiment, the beta-1,3-glucan comprises paramylon. In another embodiment, the beta-1,3-glucan does not contain beta-1,6-glycosidic bonds. In a further embodiment, the beta-1,3-glucan is purified from *Euglena*.

In some embodiments, the composition comprises *Euglena* biomass, the *Euglena* biomass comprising the beta-1,3-glucan. In some embodiments, the *Euglena* biomass is dried. In further embodiments, the *Euglena* biomass has been further processed to have an average particle size of 1000 microns or less.

In one embodiment, the composition is administered daily as a single dose. In another embodiment, the composition is administered as multiple separate doses in a single day.

In some embodiments, the composition further comprises an additional component selected from the group consisting of alpha tocopherol, cholecalciferol, zinc, chromium, selenium, arginine, ascorbic acid, alkylglycerol, caffeine, kava kava, *Curcuma longa, Spirulina, Chlorella, stevia*, calcium D-glucarate, coenzyme Q10, peptides, dimethylglycine, docosahexaenoic acid, eicosapentaenoic acid, alpha-lineolenic acid, astaxanthin, beta carotene, lutein, *lactobacillus* probiotics, *bifidobacterium* probiotics, mannoligosaccharide, fructooligosaccharides, *Astragalus, Echinacea*, Esberitox, garlic, glutathione, kelp, L-arginine, L-ornithine, lecithin granules, extracts from maiitake, reishi or shiitake mushrooms, manganese, quercetin, bromelain, Olive Leaf, *Sambucus*, Umcka, panthothenic acid, quercetin, alpha lipoic acid, essential oils, fish oils, spices and their derivatives, pterostilbene, and combinations thereof. In one embodiment, the composition is administered as a solid. In another embodiment, the composition is administered as a suspension.

In another aspect, the application provides a method of modulating the immune function in a human having high cholesterol or at risk of having high cholesterol comprising orally administering to the human an effective amount of a composition comprising beta-1,3-glucan derived from *Euglena* grown using fermentation. In some aspects, administration of the composition reduces the level of cholesterol in the human.

In one embodiment, the effective amount of the composition is between 0.1 mg beta-1,3-glucan/kg body weight and 50 mg beta-1,3-glucan/kg body weight. In another embodiment, the *Euglena* is heterotrophically grown. In a further embodiment, the beta-1,3-glucan comprises paramylon. In yet another embodiment, the beta-1,3-glucan does not contain beta-1,6-glycosidic bonds. In another embodiment, the beta-1,3-glucan is purified from *Euglena*.

In some embodiments, the composition comprises *Euglena* biomass, the *Euglena* biomass comprising the beta-1,3-glucan. In further embodiments, the *Euglena* biomass is dried. In some embodiments, the *Euglena* biomass has been further processed to have an average particle size of 1000 microns or less.

In one embodiment, the composition is administered daily as a single dose. In another embodiment, the composition is administered as multiple separate doses in a single day.

In one embodiment, the composition further comprises an additional component selected from the group consisting of alpha tocopherol, cholecalciferol, zinc, chromium, selenium, arginine, ascorbic acid, alkylglycerol, caffeine, kava kava, *Curcuma longa, Spirulina, Chlorella, stevia*, calcium D-glucarate, coenzyme Q10, peptides, dimethylglycine, docosahexaenoic acid, eicosapentaenoic acid, alpha-linolenic acid, astaxanthin, beta carotene, lutein, *lactobacillus* probiotics, *bifidobacterium* probiotics, mannoligosaccharide, fructooligosaccharides, *Astragalus, Echinacea*, Esberitox, garlic, glutathione, kelp, L-arginine, L-ornithine, lecithin granules, extracts from maiitake, reishi or shiitake mushrooms, manganese, quercetin, bromelain, Olive Leaf, *Sambucus*, Umcka, panthothenic acid, quercetin, alpha lipoic acid, essential oils, fish oils, spices and their derivatives, pterostilbene, and combinations thereof. In other embodiments, the composition is administered in combination with statins, nicotinic acid, bile acid resins, fabric acid derivatives, or cholesterol absorption inhibitors. In a further embodiment, the composition is administered as a solid. In another embodiment, the composition is administered as a suspension.

The present disclosure provides that the methods disclosed herein can also be adapted to the corresponding uses.

The present disclosure provides a composition comprising beta-1,3-glucan derived from *Euglena* grown using fermentation for use in modulating the immune function in a human in need thereof. In some embodiments, the composition is orally administered to the human. The present disclosure provides use of a composition comprising beta-1,3-glucan derived from *Euglena* grown using fermentation for the manufacture of a medicament for modulating the immune function in a human in need. In some embodiments, the composition is orally administered to the human.

The present disclosure provides a composition comprising beta-1,3-glucan derived from *Euglena* grown using fermentation for use in modulating the immune function in a human having high cholesterol or at risk of having high cholesterol. In some embodiments, the composition is orally administered to the human. The present disclosure provides use of a composition comprising beta-1,3-glucan derived from *Euglena* grown using fermentation for the manufacture of a medicament for modulating the immune function in a human having high cholesterol or at risk of having high cholesterol. In some embodiments, the composition is orally administered to the human.

Also described herein are methods of enhancing the immune function in a human having intestinal inflammation by administering beta-1,3-glucan derived from *Euglena*. These methods are useful for treating conditions such as inflammatory bowel disease, colitis, and Crohn's disease.

In one aspect, the application discloses a method of enhancing the immune function in a human having intestinal inflammation comprising orally administering to the human an effective amount of a composition comprising beta-1,3-glucan derived from *Euglena* grown using fermentation.

In some embodiments, the effective daily amount of the composition is between 0.1 mg beta-1,3-glucan/kg body weight and 100 mg beta-1,3-glucan/kg body weight.

In some embodiments, the intestinal inflammation is inflammatory bowel disease. In one embodiment, the intestinal inflammation is colitis. In another embodiment, the intestinal inflammation is Crohn's disease.

In some embodiments, the *Euglena* is heterotrophically grown. In one embodiment, the beta-1,3-glucan comprises paramylon. In another embodiment, the beta-1,3-glucan does not contain beta-1,6-glycosidic bonds. In a further embodiment, the beta-1,3-glucan is purified from *Euglena*.

In some embodiments, the composition comprises *Euglena* biomass, the *Euglena* biomass comprising the beta-1,3-glucan. In some embodiments, the *Euglena* biomass is dried. In further embodiments, the *Euglena* biomass has been further processed to have an average particle size of 1000 microns or less.

In one embodiment, the composition is administered daily as a single dose. In another embodiment, the composition is administered as multiple separate doses in a single day.

In some embodiments, the composition further comprises an additional component selected from the group consisting of alpha tocopherol, cholecalciferol, zinc, chromium, selenium, arginine, ascorbic acid, alkylglycerol, caffeine, kava kava, *Curcuma longa, Spirulina, Chlorella, stevia*, calcium D-glucarate, coenzyme Q10, peptides, dimethylglycine, docosahexaenoic acid, eicosapentaenoic acid, alpha-linolenic acid, astaxanthin, beta carotene, lutein, *lactobacillus* probiotics, *bifidobacterium* probiotics, mannoligosaccharide, fructooligosaccharides, *Astragalus, Echinacea*, Esberitox, garlic, glutathione, kelp, L-arginine, L-ornithine, lecithin granules, extracts from maiitake, reishi or shiitake mushrooms, manganese, quercetin, bromelain, Olive Leaf, *Sambucus*, Umcka, panthothenic acid, quercetin, alpha lipoic acid, essential oils, fish oils, spices and their derivatives, pterostilbene, and combinations thereof. In one embodiment, the composition is administered as a solid. In another embodiment, the composition is administered as a suspension.

In some embodiments, administration of the composition increases anti-inflammatory cytokine production. In further embodiments, the composition is administered in combination with anti-inflammatory drugs, immunosuppression drugs, or antibiotics.

The present disclosure provides that the methods disclosed herein can also be adapted to the corresponding uses.

The present disclosure provides a composition comprising beta-1,3-glucan derived from *Euglena* grown using fermentation for use in enhancing the immune function in a human having intestinal inflammation. These uses are useful for treating conditions such as inflammatory bowel disease, colitis, and Crohn's disease. In some embodiments, the composition is orally administered to the human. The present disclosure provides use of a composition comprising beta-1,3-glucan derived from *Euglena* grown using fermentation for the manufacture of a medicament for enhancing the immune function in a human having intestinal inflammation. These methods are useful for treating conditions such as inflammatory bowel disease, colitis, and Crohn's disease. In some embodiments, the composition is orally administered to the human.

BRIEF DESCRIPTION OF THE DRAWINGS

In FIGS. 9A-9C, the doses of beta-1,3-glucan are 0 mg/kg (A), 5 mg/kg (B), 20 mg/kg (C), and 200 mg/kg (D).

In FIGS. 12A-12C, individual lines represent the results for individual mice.

*gracilis* ("A50") to mice with DSS-induced colitis. Bars represent means±standard error (n=3 mice per treatment group).

Figure 20:
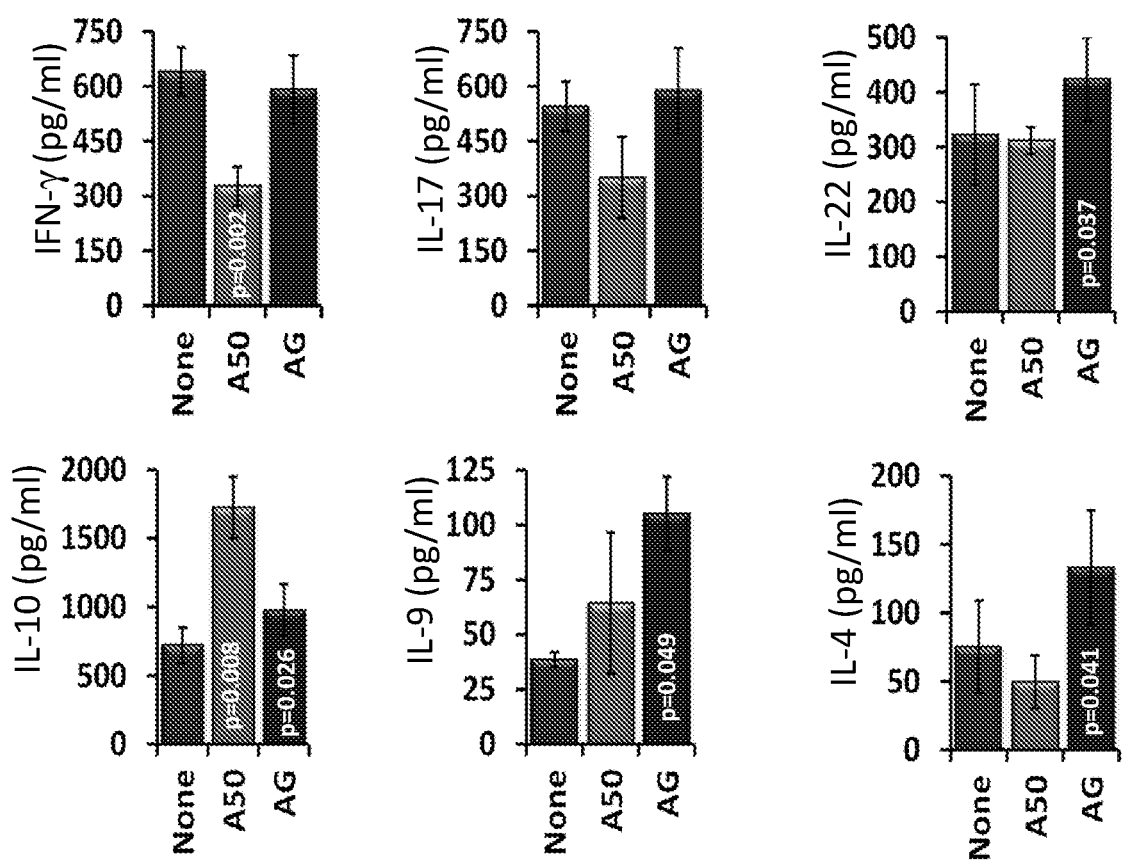

FIG. 20 graphically shows the effect of beta-1,3-glucan on cytokine production by colonic immune cells in mice with DSS-induced colitis. Bars represent means±standard error (n=3 mice per treatment group). The graph shows the cytokine profile of mice treated with PBS ("None"), purified beta-1,3-glucan ("AG"), or dried *Euglena gracilis* ("A50"). Bars represent means±standard error (n=3 mice per treatment group).

Figure 21:
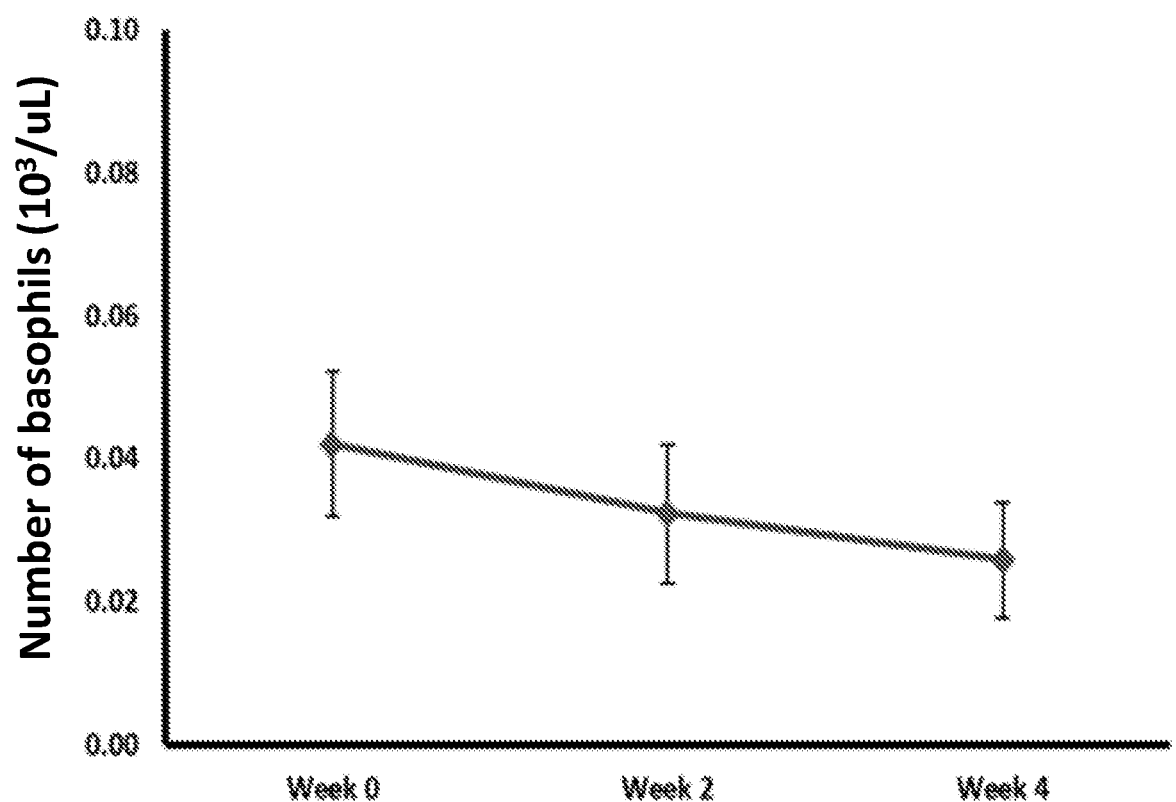

FIG. 21 graphically shows reduction in the number of basophils in an individual following daily consumption of 250 mg of beta-1,3-glucan derived from *Euglena*.

Figure 22:
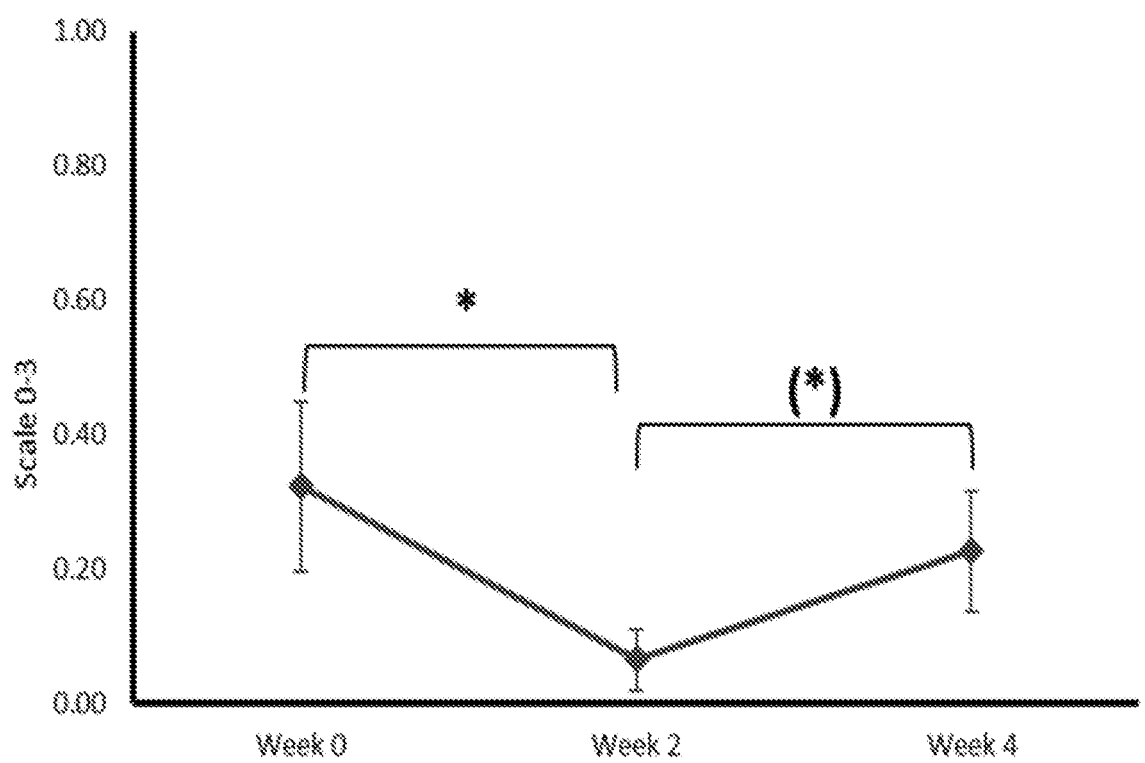

FIG. 22 graphically shows the effect on urgent bowel movements or diarrhea in an individual following daily consumption of 250 mg of beta-1,3-glucan derived from *Euglena*.

Figure 23:
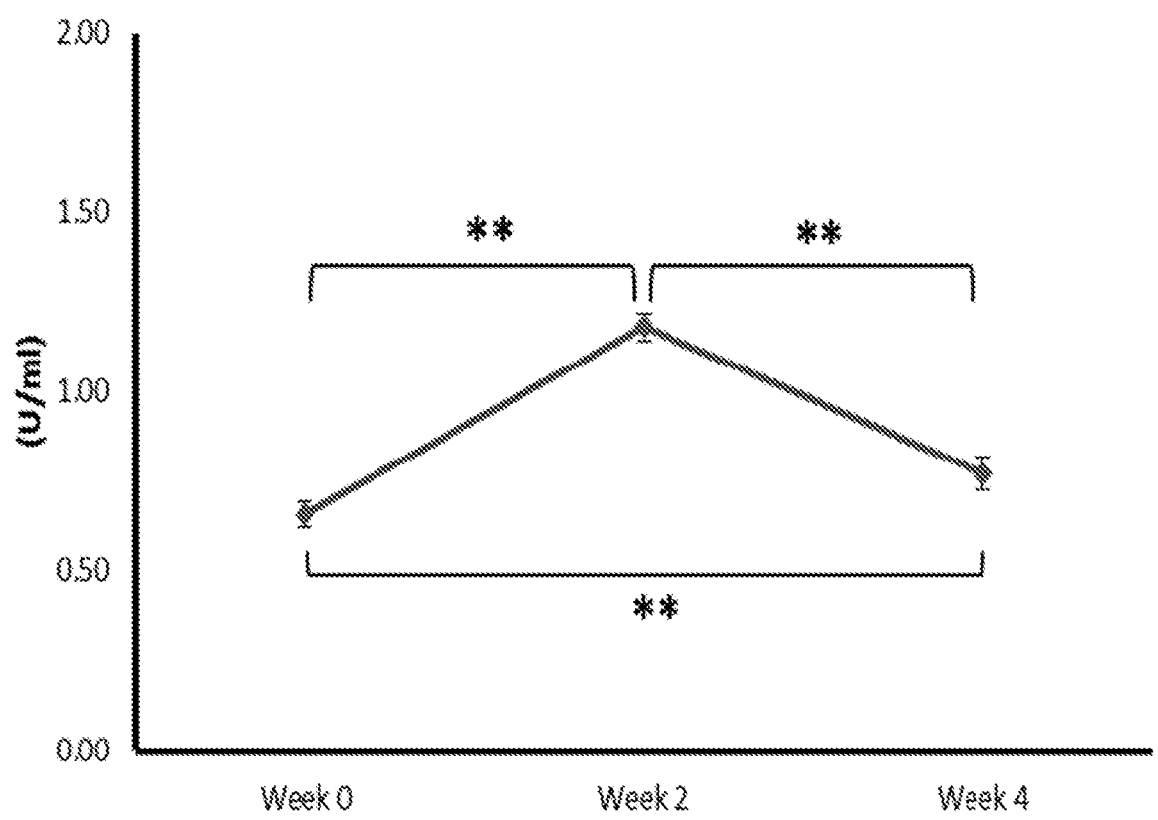

FIG. 23 graphically shows the effect on levels of the enzyme Superoxide Dismutase (SOD) in an individual following daily consumption of 250 mg of beta-1,3-glucan derived from *Euglena*.

Figure 24:
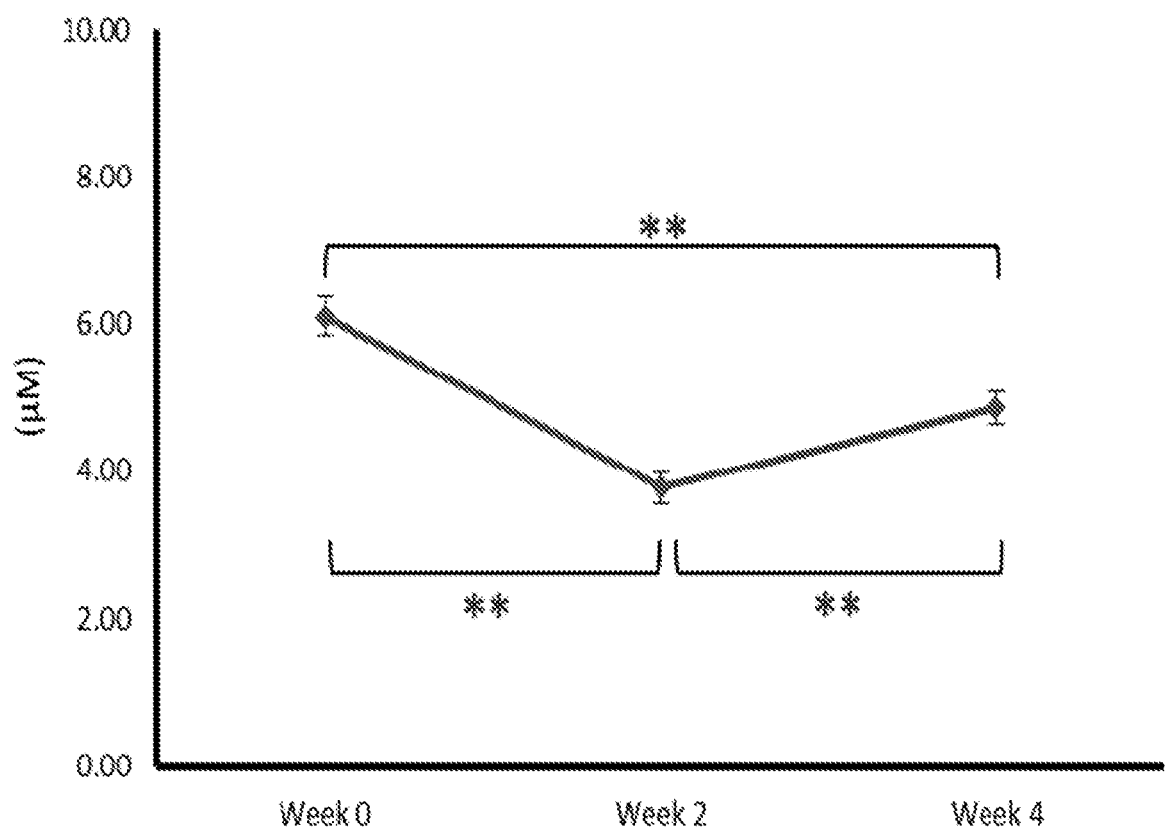

FIG. 24 graphically shows the effect on levels of malondialdehyde in an individual following daily consumption of 250 mg of beta-1,3-glucan derived from *Euglena*.

Figure 25:
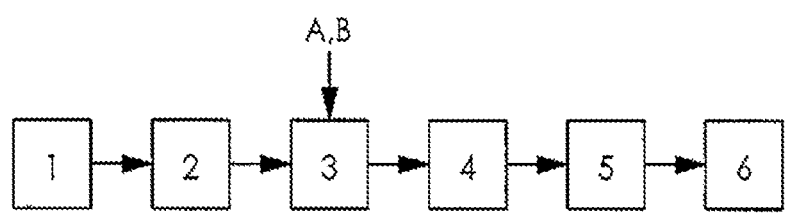

FIG. 25 is a schematic of an embodiment of a fermentation process to prepare a complex of beta glucan with a trace metal.

Figure 26:
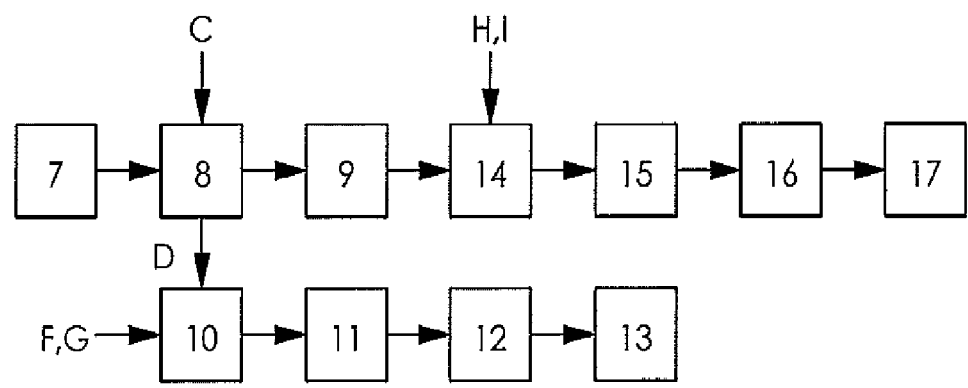

FIG. 26 is a schematic of another embodiment of a fermentation process to prepare a complex of beta glucan with a trace metal.

DETAILED DESCRIPTION

The present disclosure provides a method of treating a condition selected from the group consisting of hyperlipidemia, metabolic syndrome, inflammatory bowel disease, colitis, Crohn's disease, and colon cancer in a human with said condition, the method comprising orally administering to the human an effective amount of a composition comprising beta-1,3-glucan from *Euglena* grown using fermentation. In certain embodiments, the condition is selected from the group consisting of hyperlipidemia, metabolic syndrome, inflammatory bowel disease, colitis, and Crohn's disease. In certain embodiments, the composition comprising beta-1,3-glucan from *Euglena* grown using fermentation can include *Euglena* biomass, beta-1,3-glucan from *Euglena*, or purified beta-1,3-glucan from *Euglena* or combinations thereof. The composition can be used for treating a condition selected from the group consisting of hyperlipidemia, metabolic syndrome, inflammatory bowel disease, colitis, Crohn's disease, and colon cancer in a human with said condition. In certain embodiments, the composition can be used for treating a condition selected from the group consisting of hyperlipidemia, metabolic syndrome, inflammatory bowel disease, colitis, and Crohn's disease in a human with said condition. In certain embodiments, the composition can be used for treating hyperlipidemia. In certain embodiments, the composition can be used for treating metabolic syndrome. In certain embodiments, the composition can be used for treating inflammatory bowel disease. In certain embodiments, the composition can be used for treating colitis. In certain embodiments, the composition can be used for treating Crohn's disease. In certain embodiments, the composition can be used for treating colon cancer.

The present application is directed to beta-1,3-glucan derived from *Euglena* and uses thereof. Beta-1,3-glucan derived from *Euglena* can modulate the immune function in an individual. The present application is also directed to beta-1,3-glucan derived from *Euglena* and uses thereof to modulate or enhance the immune function of a human having intestinal inflammation. Beta-1,3-glucan derived from *Euglena* can modulate or enhance the immune function in an individual having intestinal inflammation. The beta-1,3-glucan derived from *Euglena* can be orally administered as an edible composition containing either *Euglena* biomass or beta-1,3-glucan purified from *Euglena*. Purified beta-1,3-glucan derived from *Euglena* can also be administered as a pharmaceutical formulation, which may be administered orally or intravenously.

The inventors have discovered that administration of beta-1,3-glucan derived from *Euglena* grown using fermentation can be used to promote immune system health and to treat and/or prevent disease in animals, including humans. For example, beta-1,3-glucan derived from *Euglena* can be used to modulate an autoimmune response, blood sugar levels, an infection, or inflammation. Administration of beta-1,3-glucan derived from *Euglena* grown by fermentation also results in decreased blood serum cholesterol or decreased blood serum triglycerides in an animal, including humans.

The inventors have also surprisingly shown that administration of beta-1,3-glucan derived from *Euglena* grown using fermentation can be used to promote immune system health and to treat and/or prevent intestinal inflammation in animals, including humans. For example, beta-1,3-glucan derived from *Euglena* can be used to modulate or enhance the immune function of a human having inflammatory bowel disease, colitis, or Crohn's disease. Administration of beta-1,3-glucan derived from *Euglena* grown by fermentation also results in increased production of anti-inflammatory cytokines in an animal, including humans.

There are several advantages to using beta-1,3-glucan derived from *Euglena*. First, beta-1,3-glucan is efficiently produced by *Euglena* grown using fermentation. *Euglena* grown by fermentation as described herein accumulate beta-1,3-glucan to between about 30% and about 70% of the total *Euglena* cell mass. In contrast, yeast-derived beta glucan, for example, accounts for less than 15% of the total yeast cell mass. Second, beta-1,3-glucan derived from *Euglena* can be readily extracted and purified. Beta glucan derived from yeast, on the other hand, is bound to the yeast cell wall, making extraction difficult and costly. As discussed below, beta-1,3-glucan accumulates in granules in *Euglena*. This facilitates the purification process, as the beta-1,3-glucan derived from *Euglena* is not associated with cell wall components that can be difficult to separate. Third, beta-1,3-glucan derived from *Euglena* is readily bioavailable, with little or no processing of the *Euglena* cells. This allows the beta-1,3-glucan derived from *Euglena* to be effectively administered as a *Euglena* biomass and without the need for purification. Furthermore, if purified beta-1,3-glucan is desired, for example in a pharmaceutical formulation, it can be readily purified using a safe and cost-effective process as described herein. In contrast, beta glucan produced by oats or yeast must be extracted from the cell wall and requires the use of dangerous chemicals or expensive enzymes.

*Euglena* produces unique beta glucans that are particularly useful to modulate immune function or to treat or prophylactically treat hyperlipidemia. Also, *Euglena* produces unique beta glucans that are particularly useful to treat or prophylactically treat intestinal inflammation. A substantial portion of the beta-1,3-glucan produced by *Euglena* is located in the organism's pyrenoid or cytoplasm as paramylon bodies, which are water-insoluble granules of the beta-1,3-glucan. This unique beta glucan is commonly referred to as paramylon. Compared to many other organisms, such as oat or fungal beta glucan, beta glucan produced by *Euglena* is substantially more linear, containing predominately beta-1,3-linkages. The beta-1,3-glucan form is particularly effective at modulating immune function and reducing blood serum cholesterol and triglyceride levels. Also, the beta-1,3-glucan form is particularly effective at treating or preventing intestinal inflammation.

Definitions

The term "effective amount" describes an amount of a compound or component which, when used within the context of its use, produces or effects an intended result, whether that result relates to the prophylaxis or treatment of an infection or disease state or as otherwise described herein.

The terms "modulate", "modulating", "modulation", "enhance", "enhancing", and "enhancement" are used synonymously herein to describe the improved ability of any human or animal (including, but not limited to, a dog, cat, rodent, horse, sheep, cow, pig, goat, donkey, chicken, or rabbit) to mount an immune response.

The term "*Euglena*" is understood to mean any species or strain within the *Euglena* genus, unless otherwise specified. In a preferred embodiment, the *Euglena* is *Euglena gracilis*, but other *Euglena* species are contemplated.

The term "biomass" is used to describe the *Euglena* cell material. The product may be processed or unprocessed. For example, *Euglena* biomass may be dried or provided as a wet cell mass.

The term "derived from" means that the compound or material originated from a particular source. For example, beta-1,3-glucan derived from *Euglena* indicates that the beta-1,3-glucan originated from *Euglena*. The beta-1,3-glucan may be associated with the *Euglena* or may be purified and hence separated from the *Euglena*.

The term "pharmaceutically acceptable" as used herein means that the compound or composition is suitable for administration to a subject, including a human patient, to achieve the treatments described herein, without unduly deleterious side effects in light of the severity of the disease and necessity of the treatment.

The terms "subject", "patient", and "individual" are used synonymously herein to describe any human or animal (including, but not limited to, a dog, cat, rodent, horse, sheep, cow, pig, goat, donkey, chicken, or rabbit). In some embodiments, the terms "subject", "patient", and "individual" are used synonymously herein to describe any human or animal (including, but not limited to, a dog, cat, rodent, horse, sheep, cow, pig, goat, donkey, llama, fish, chicken or rabbit).

The terms "treat," "treating," and "treatment" are used synonymously herein to refer to any action providing a benefit to a patient at risk for or afflicted with a disease state or condition, including improvement in the condition through lessening, inhibition, suppression, or elimination of at least one symptom, delay in progression of the disease, or inhibition of the disease.

The term "prophylactic administration" or "prophylactic treatment" refers to any action in advance of the occurrence of disease to reduce the likelihood of that disease or any action to reduce the likelihood of the subsequent occurrence of disease in the subject.

The term "about" includes and describes the value or parameter per se. For example, "about x" includes and describes "x" per se. In certain embodiments, the term "about" when used in association with a measurement, or used to modify a value, a unit, a constant, or a range of values, refers to variations of ±1-10%. In some embodiments, the term "about" when used in association with a measurement, or used to modify a value, a unit, a constant, or a range of values, refers to variations of ±5%. In some embodiments, the term "about" when used in association with a measurement, or used to modify a value, a unit, a constant, or a range of values, refers to variations of ±10%.

The term "and/or" includes subject matter in the alternative as well as subject matter in combination. For instance, "x and/or y" includes "x or y" and "x and y".

It is understood that aspects and embodiments of the invention described herein include "consisting of" and/or "consisting essentially of" aspects and embodiments.

As used herein, the singular forms "a," "an," and "the" include the plural reference unless the context clearly dictates otherwise.

Properties of Beta-1,3-Glucan Derived from *Euglena*

Beta-1,3-glucan derived from *Euglena* is structurally distinct from beta glucans produced by other organisms in terms of its carbohydrate branching structure, three-dimensional structure, solubility, and bioavailability.

Carbohydrate Branching Structure

Figure 1:
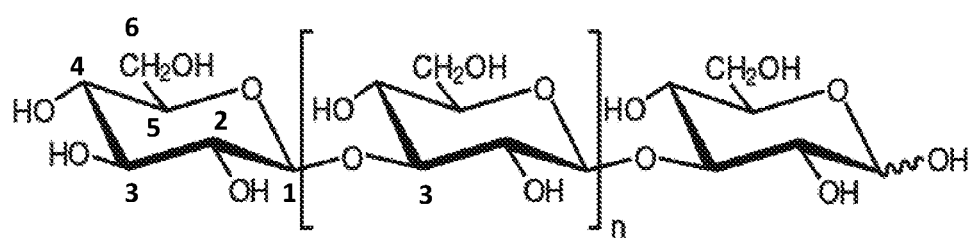
FIG. 1A shows the structure of a beta-1,3-glucan chain, such as that derived from *Euglena*.
FIG. 1B shows the structure of a beta-1,3-glucan backbone with beta-1,6-glucan side chains, such as that derived from yeast.
Figure 1:
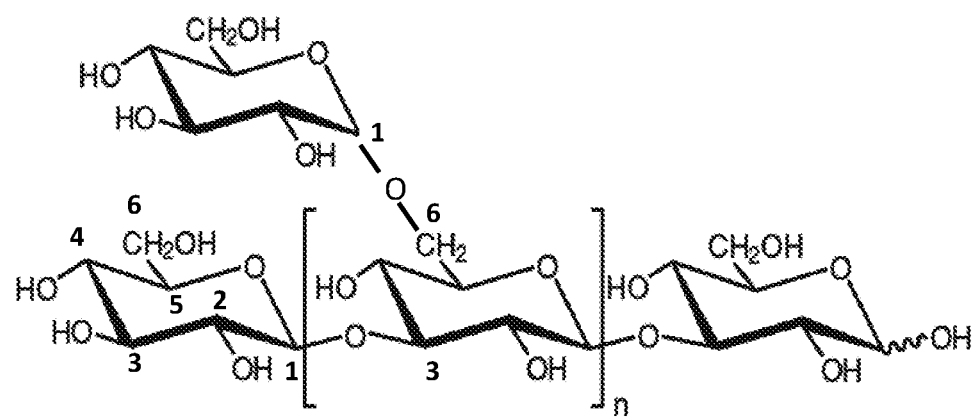

Beta glucans produced by different organisms can vary substantially in the carbohydrate branching structure of the polymer. For example, beta glucan derived from algae such as *Euglena* has almost exclusively 1,3-glycosidic bonds and no 1,6-glycosidic bonds (FIG. 1A). In contrast, beta glucan derived from yeast has a mixture of beta-1,3- and beta-1,6-glycosidic linkages, generally with a beta-1,3-glucan backbone that includes beta-1,6-side chains (2-3 glucose units long) every 10-30 glucose monomers (FIG. 1B). Beta glucan derived from oats or barley has a mixture of beta-1,3- and beta-1,4-glycosidic linkages. Beta glucan derived from kelp (e.g., *Laminaria*) has a mixture of beta-1,3- and beta-1,6-glycosidic linkages.

A substantial portion of the beta glucan produced by *Euglena* is located in the algal cytoplasm as paramylon bodies, and is commonly referred to as "paramylon." Paramylon derived from *Euglena* has a linear structure with almost exclusively beta-1,3-glucan with no beta-1,6-side branches. The unbranched nature of paramylon is an important distinction compared to other sources of beta glucans when considering its use in immune support applications.

A study of the branching structure of paramylon reveals its unique structure, and is disclosed in U.S. Patent Publication No. 2013/0216586. After isolating paramylon from whole *Euglena* cells, a linkage analysis was performed to determine the relative amounts of each type of bond between glucose monomers. The results are summarized in Table 1.

TABLE 1

Linkage Analysis of Two Paramylon Samples Extracted from *Euglena gracilis*.

| GLYCOSYL RESIDUE | Sample 1 (%) | Sample 2 (%) |
| --- | --- | --- |
| Terminally-linked glucopyranosyl residue (t-glc) | 0.34 | 0.3 |
| 3-linked glucopyranosyl residue (3-glc) | 93.03 | 94.1 |
| 4-linked glucopyranosyl residue (4-glc) | 2.25 | 2.4 |

TABLE 1-continued

Linkage Analysis of Two Paramylon Samples Extracted from *Euglena gracilis*.

| GLYCOSYL RESIDUE | Sample 1 (%) | Sample 2 (%) |
|---|---|---|
| 2,3-linked glucopyranosyl residue (2,3 glc) | 3.47 | 2.3 |
| 3,6-linked glucopyranosyl residue (3,5-glc) | 0.36 | 0.8 |
| 2,3,4-linked glucopyranosyl residue (2,3,4-glc) | 0.55 | 0.1 |
| TOTAL | 100.0 | 100.0 |

This linkage analysis indicates that both paramylon samples are mainly composed of 3-linked glucopyranosyl residues. Minor amounts of 4-linked and 2,3 linked glucopyranosyl residues were found along with negligible amounts of 3,6-linked, terminal and 2,3,4-linked glucopyranosyl residues. These data confirm that paramylon is comprised mostly of a linear, unbranched beta-1,3-glucan.

Beta-1,3-glucan is the form of beta glucan that predominantly binds to receptors on the surface of immune system cells, such as Dectin-1 (a macrophage receptor) and complement receptor 3. Beta-1,3-glucan can also be fermented by microflora in an individual's intestine, which may result in the production of beneficial metabolites like short chain fatty acids that may affect the animal's health. Beta-1,3-glucan can also be fermented by microflora in an individual's intestine, which may result in the production of beneficial metabolites such as short chain fatty acids that may affect the individual's health.

Beta-1,3-glucan derived from *Euglena* grown using fermentation useful for the methods described herein contains about 85% or more beta-1,3-glycosidic linkages, about 87% or more beta-1,3-glycosidic linkages, about 90% or more beta-1,3-glycosidic linkages, about 91% or more beta-1,3-glycosidic linkages, about 92% or more beta-1,3-glycosidic linkages, about 93% or more beta-1,3-glycosidic linkages, or about 94% or more beta-1,3-glycosidic linkages.

Three-Dimensional Structure

The three-dimensional structure and folding of beta-1,3-glucan can affect the bioavailability, surface area, and overall efficacy in immune stimulation applications. In linear beta-1,3-glucan chains, the structure is governed by the glycosidic linkage pattern. Because the chair-form ring of glucopyranosyl is rather rigid, most of the flexibility of the glucan chain arises from rotations around the bonds of the glycosidic linkages. X-ray crystallography and spectroscopy techniques indicate that linear glucans have a triple-helix backbone in the solid state. Paramylon produced by *Euglena* is considered to be one of the more structurally simple of the beta glucans, with few glycosyl side chains. This is in direct contrast to laminaran, lentinan, scleroglucan, schizopylann, or yeast-derived beta glucans that have 1,4- or 1,6-linked side chains exposed toward the exterior of the helical structure.

The triple-helix structure is stable over a broad range of temperatures at a neutral pH, resulting in a polymer that is water insoluble. However, the hydrogen bonds can be destabilized by various means to change the conformation of the paramylon polymer. For example, paramylon can be dissolved in alkaline solutions (for example, in 0.2 M NaOH or stronger), aprotic polar solvents like DMSO, in the presence of strong chaotropic agents (e.g., urea), or by increasing temperatures above the triple-helix melting temperatures (~135° C.). Different immunological effects can be obtained that are related to the beta-1,3-glucan conformation, be it the native state, denatured, or denatured and re-natured. Beta-1,3-glucan in any of these three conformations can serve as the building block for additional reactions that add or improve its functionality. Several of these modifications to produce functionalized beta-1,3-glucans and some of their respective applications are discussed herein. The conformation of the beta glucan and its resulting solubility may also affect how it is delivered. For example, water soluble beta-1,3-glucan can be injected intravenously.

Particle Size

The particle size is a factor that affects the function and bioavailability of the beta-1,3-glucan particle. Beta-1,3-glucan particles derived from *Euglena* are useful for the methods described herein. Generally, the beta-1,3-glucan particles derived from *Euglena* have an average diameter of about 7 microns or less, about 6 microns or less, about 5 microns or less, about 4 microns or less, about 3 microns or less, about 2.5 microns or less, about 2 microns or less, about 1.5 microns or less, about 1 micron or less, about 0.5 microns or less, about 0.4 microns or less, about 0.3 microns or less, about 0.2 microns or less, or about 0.1 microns or less.

Level of Purity of Beta-1,3-Glucan

The level of purity of a beta glucan compound has been determined to have an effect on efficacy, possibly stemming from other material present that inhibits the interaction between the beta glucan and immune cells. Using the methods described herein, beta-1,3-glucan can be easily isolated in the form of granules from *Euglena* cells. As a result, the purity of the beta-1,3-glucan derived from *Euglena* is very high relative to common preparations of beta glucans from yeast and other organisms. For example, beta-1,3-glucan derived from *Euglena* is not associated with cell wall components, as is the case for beta glucans derived from yeast and certain other organisms. Rather, the beta-1,3-glucan derived from *Euglena* is extracted predominantly in the form of water-insoluble granules. Accordingly, purification of beta-1,3-glucan derived from *Euglena* is not complicated by association of the beta glucan with cell wall components. Using the methods described herein, purity levels greater than 95 weight percent can be obtained on an as-received basis. In some embodiments, purity levels greater than 99 weight percent can be obtained on an as-received basis. In comparison, the highest-grade yeast-derived beta glucans can rarely achieve greater than 90% purity and most are about 70-80% purity. Moreover, high purity beta-1,3-glucan can be achieved more cost-effectively when produced by *Euglena* than with yeast-derived glucans due to the ease of separation resulting from the lack of a cell wall in *Euglena* and easy recovery of the beta-1,3-glucan granules. Finally, since no harsh chemicals (e.g., strong acids and bases or solvents) are required to recover the beta-1,3-glucan derived from *Euglena*, the beta-1,3-glucan can be recovered in its native form without modifying its chemical composition and configuration. The use of pure, unmodified beta-1,3-glucan derived from *Euglena* is advantageous in comparison to solubilized and modified beta glucans obtained from other organisms that are modified during the extraction and/or purification process, in part because of the higher bioavailability of beta-1,3-glucan derived from *Euglena*. In some embodiments, purified beta-1,3-glucan derived from *Euglena* is more that 85% pure, more than 90% pure, more than 92% pure, more than 94% pure, more than 95% pure, more than 96% pure, more than 97% pure, more than 98% pure, or more than 99% pure.

Methods of Treating Hyperlipidemia

Oral administration of beta glucan derived from *Aureobasidium pullulans* was recently found to prevent the development of high fat diet (HFD)-induced fatty liver in mice (Aoki, S. et al. Scientific Reports 2015, 5, 10457). Beta glucan derived from *Aureobasidium pullulans* consists of both beta-1,3- and -1,6-glycosidic bonds. In the study, the rate limiting enzymes for cholesterol synthesis, HMGR, and cholesterol degradation, CYP7A1, were significantly upregulated in mice. The authors of the study specifically pointed to the upregulation of CYP7A1 mRNA expression as a possible molecular basis for the observed improvements of fatty liver, liver injury, and cholesterol levels. Induction of IL-6 was also implicated in the prevention of HFD-induced fatty liver in mice. In a separate study involving beta glucan derived from yeast, reduction of cholesterol plasma levels in mice was proposed to be mediated by macrophages (Vetvicka, V. et al. *J. of Immunotoxicology*, 2009, 6, 30-35). Clearly, the exact molecular mechanism by which beta glucans modulate the immune system and, in turn, regulate cholesterol levels, is complex and may depend on the exact structure of the beta glucan.

Hyperlipidemia, or abnormally high blood cholesterol or triglyceride levels, creates substantial risk for heart attacks and cardiovascular disease. Hyperlipidemia may result from genetic factors or certain health or lifestyle factors, including a high-fat or high-cholesterol diet, obesity, or lack of regular exercise. Hyperlipidemia includes any condition resulting in elevated blood cholesterol (i.e., hypercholesterolemia) or blood triglyceride (hypertriglyceridemia) levels. Cholesterol and triglycerides are associated with lipoproteins, including low-density lipoprotein (LDL) and high-density lipoprotein (HDL). LDL, which is frequently referred to as "bad" cholesterol, collects in the walls of blood vessels and can lead to plaque growth and atherosclerosis. In contrast, HDL (often referred to as "good" cholesterol) transfers fats away from cells, artery walls, and tissues through the bloodstream. Increasing concentrations of HDL particles are associated with decreasing accumulation of atherosclerosis within the walls of arteries. Beta-1,3-glucan derived from *Euglena* grown using fermentation (e.g., *Euglena* biomass, beta-1,3-glucan from *Euglena*, or purified beta-1,3-glucan from *Euglena* or combinations thereof) can be administered to a subject, including a human, to treat hyperlipidemia or prophylactically administered to a subject at risk for hyperlipidemia. Beta-1,3-glucan derived from *Euglena* grown using fermentation (e.g., *Euglena* biomass, beta-1,3-glucan from *Euglena*, or purified beta-1,3-glucan from *Euglena* or combinations thereof) can be administered to a subject, including a human, to lower LDL. Beta-1,3-glucan derived from *Euglena* grown using fermentation (e.g., *Euglena* biomass, beta-1,3-glucan from *Euglena*, or purified beta-1,3-glucan from *Euglena* or combinations thereof) can be administered to a subject, including a human, to increase HDL. A person at risk for hyperlipidemia can include, but is not limited to, a person who has been previously diagnosed with hyperlipidemia, a person with a high-fat or high-cholesterol diet, or a person with one or more parents with hyperlipidemia.

Beta-1,3-glucan derived from *Euglena* grown using fermentation (e.g., *Euglena* biomass, beta-1,3-glucan from *Euglena*, or purified beta-1,3-glucan from *Euglena* or combinations thereof) can also be administered to a subject, including a human, to treat non-alcoholic fatty liver disease (NAFLD), or prophylactically administered to a subject at risk for NAFLD. Closely associated with obesity and type 2 diabetes, NAFLD is known to be a major risk factor for cardiovascular diseases.

Beta-1,3-glucan derived from *Euglena* grown using fermentation (e.g., *Euglena* biomass, beta-1,3-glucan from *Euglena*, or purified beta-1,3-glucan from *Euglena* or combinations thereof) can be administered to a subject, including a human, to treat metabolic syndrome, or prophylactically administered to a subject at risk for metabolic syndrome. Metabolic syndrome refers to a cluster of conditions including increased blood pressure, high blood sugar levels, excess body fat, abnormal cholesterol levels that occur together to increase risk of heart disease, stroke, and diabetes.

Administration of beta-1,3-glucan derived from *Euglena* grown using fermentation as described herein (e.g., *Euglena* biomass, beta-1,3-glucan from *Euglena*, or purified beta-1,3-glucan from *Euglena* or combinations thereof) has been shown to lower blood cholesterol and triglyceride levels (see Example 7). Such administration can be oral, such as by administering an edible composition or an oral pharmaceutical formulation, or intravenous, such as by administering an intravenous pharmaceutical formulation. Alternate routes of administration, such as by inhalation, are also contemplated. The oral edible composition or oral pharmaceutical formulation includes either purified or non-purified beta-1,3-glucans derived from *Euglena* grown using fermentation as described herein. Generally, the intravenous pharmaceutical formulation includes purified beta-1,3-glucans derived from *Euglena* grown using fermentation. Typically, the pharmaceutical formulation suitable for inhalation includes purified beta-1,3-glucans derived from *Euglena* grown using fermentation and may be administered by, for example, a nasal spray. The edible composition or pharmaceutical formulation can be administered in combination with one or more statins, nicotinic acid, bile acid resins, fibric acid derivatives, or cholesterol absorption inhibitors to enhance the treatment of hyperlipidemia.

The fermented *Euglena* useful to produce the beta-1,3-glucan for the treatment of hyperlipidemia generally rely on a growth media to provide nutrients for growth and production of the beta-1,3-glucan. While it is contemplated that the *Euglena* could grow in full or partial light exposure, it is generally preferred that the *Euglena* grown using fermentation are heterotrophically grown. During fermentation, the growing *Euglena* efficiently produce beta-1,3-glucan. In some embodiments, the *Euglena* cells accumulate beta-1,3-glucan between about 30 wt % to about 70 wt % beta-1,3-glucan, about 30 wt % to about 40 wt % beta-1,3-glucan, about 40 wt % to about 50 wt % beta-1,3-glucan, about 60 wt % to about 70 wt % beta-1,3-glucan, about 40 wt % to about 70 wt % beta-1,3-glucan, or about 50 wt % to about 70 wt % beta-1,3-glucan. In some embodiments, the *Euglena* cells accumulate beta-1,3-glucan between about 50 wt % to about 60 wt % beta-1,3-glucan, or about 50 wt % to about 55 wt % beta-1,3-glucan.

The beta-1,3-glucan derived from *Euglena* and grown using fermentation is administered to a subject for treating hyperlipidemia in a purified form or in an unpurified form. For example, a *Euglena* biomass grown using fermentation can be orally administered to a subject to treat hyperlipidemia. Because the *Euglena* grown using fermentation contain effective amounts of the beta-1,3-glucan, the *Euglena* biomass is effective for reducing blood cholesterol levels or blood triglyceride levels even without purifying the beta-1,3-glucan. This is due, in part, to the high bioavailability of the beta-1,3-glucan produced by *Euglena* grown by fermentation. In contrast, beta glucan produce by yeast is tightly associated with the cell wall of the yeast, and has lower amounts of bioavailable beta glucan.

For example, the *Euglena* biomass is provided in an edible composition that is orally administered to reduce blood cholesterol levels and/or blood triglyceride levels. The edible composition may be a food product or a dietary supplement. To aid consumption, the *Euglena* biomass can be processed into sheet, a paste, a cream, a powder, a capsule, a tablet, or any other edible solid or liquid (such as a suspension) and consumed by itself or in combination with another food product. For example, in some embodiments the *Euglena* biomass is administered in a beverage, such as a nutritional shake, in a nutritional bar, in baked goods, or in a cereal.

In one exemplary embodiment, the *Euglena* biomass is dried to prepare it for oral administration. For example, the *Euglena* biomass can be dried by freeze-drying the biomass, heating the biomass in an oven, double drum dryer, or similar drying device, or applying a vacuum to the biomass to a moisture content of about 40% or less, about 30% or less, about 25% or less, about 20% or less, about 15% or less, about 10% or less, about 5% or less, about 4% or less, about 3% or less, about 2% or less, or about 1% or less. Optionally, either before or after drying the *Euglena* biomass, the biomass is processed into a powder. For example, the *Euglena* cells are suspended in solution, pulverized by a shear mixer, and dried to produce the powder. In some embodiments, the powdered *Euglena* biomass is processed to an average particle size of about 1000 microns or less, about 900 microns or less, about 800 microns or less, about 700 microns or less, about 600 microns or less, about 500 microns or less, about 400 microns or less, about 300 microns or less, about 250 microns or less, about 200 microns or less, about 100 microns or less, about 50 microns or less, about 25 microns or less, about 15 microns or less, about 10 microns or less, about 5 microns or less, about 3 microns or less, about 2 microns or less, about 1 micron or less, or about 0.5 microns or less. The dried and/or powdered *Euglena* biomass can then be orally administered to a subject, either directly or by mixing with another edible composition, to reduce blood cholesterol levels and/or blood triglyceride levels in the subject.

The orally administered *Euglena* biomass can further include nutritional supplements in addition to the beta-1,3-glucan. The nutritional supplements may be pre-existing in the *Euglena* biomass or may be added to the *Euglena* biomass. Exemplary additional supplements include alpha tocopherol, cholecalciferol, zinc, chromium, selenium, arginine, ascorbic acid, alkylglycerol, caffeine, kava kava, *Curcuma longa, Spirulina, Chlorella, stevia*, calcium D-glucarate, coenzyme Q10, peptides, dimethylglycine, docosahexaenoic acid, eicosapentaenoic acid, alpha-linolenic acid, astaxanthin, beta carotene, lutein, *lactobacillus* probiotics, *bifidobacterium* probiotics, mannoligosaccharide, fructooligosaccharides, *Astragalus, Echinacea*, Esberitox, garlic, glutathione, kelp, L-arginine, L-ornithine, lecithin granules, extracts from maiitake, reishi or shiitake mushrooms, manganese, quercetin, bromelain, olive leaf, *Sambucus*, Umcka, panthothenic acid, quercetin, alpha lipoic acid, essential oils, fish oils, spices and their derivatives, and pterostilbene. These additional supplements can function independently of, or synergistically with, the beta-1,3-glucan derived from *Euglena* grown using fermentation to reduce blood cholesterol levels and/or blood triglyceride levels. Additional components include any of *Haematococcus pluvialis*, astaxanthin, and colostrum.

The orally administered *Euglena* biomass may further comprise a pharmaceutically acceptable excipient. Example pharmaceutically acceptable excipients include fillers, binders, coatings, preservatives, lubricants, flavoring agents, sweetening agents, coloring agents, surfactants, solvents, buffering agents, chelating agents, or stabilizers. Examples of pharmaceutically acceptable fillers include cellulose, dibasic calcium phosphate, calcium carbonate, microcrystalline cellulose, sucrose, lactose, glucose, mannitol, sorbitol, maltitol, pregelatinized starch, corn starch, and potato starch. Examples of pharmaceutically acceptable binders include polyvinylpyrrolidone, starch, lactose, xylitol, sorbitol, maltitol, gelatin, sucrose, polyethylene glycol, methyl cellulose, and cellulose. Examples of pharmaceutically acceptable coatings include hydroxypropyl methylcellulose (HPMC), shellac, corn protein zein, and gelatin. Examples of pharmaceutically acceptable disintegrants include polyvinylpyrrolidone, carboxymethyl cellulose, and sodium starch glycolate. Examples of pharmaceutically acceptable lubricants include polyethylene glycol, magnesium stearate, and stearic acid. Examples of pharmaceutically acceptable preservatives include methyl parabens, ethyl parabens, propyl paraben, benzoic acid, and sorbic acid. Examples of pharmaceutically acceptable sweetening agents include sucrose, saccharine, aspartame, or sorbitol. Examples of pharmaceutically acceptable buffering agents include carbonates, citrates, gluconates, acetates, phosphates, or tartrates.

Beta-1,3-glucan derived from *Euglena* grown using fermentation can also be administered to a subject to reduce blood cholesterol levels and/or blood triglyceride levels in a purified form. In some embodiments, beta-1,3-glucan is purified from *Euglena* to be more than 85% pure, more than 90% pure, more than 92% pure, more than 94% pure, more than 95% pure, more than 96% pure, more than 97% pure, more than 98% pure, or more than 99% pure. Generally, the beta-1,3-glucan is extracted by lysing the *Euglena* cells and isolating the beta-1,3-glucan. The *Euglena* cells can be lysed using sonication or high pressure homogenization. Optionally, additional chemicals are included during the lysis step to aid the lysis, but such chemicals are not necessarily required. Exemplary additional chemicals included during the lysis step include detergents (such as sodium dodecyl sulfate), enzymes, bases (such as sodium hydroxide), or acids (such as acetic acid or hydrochloric acid). The beta-1,3-glucan can be isolated from the lysed *Euglena* cells using filtration or gravity separation (such as gravity settling or centrifugation). To obtain higher levels of purity, the isolated beta-1,3-glucan is washed, for example with an aqueous solution or ethanol.

Purified beta-1,3-glucan can also be modified to increase its potency in reducing blood serum cholesterol levels or blood serum triglyceride levels. For example, the beta-1,3-glucan can be sulfated, conjugated to pyridinium moiety, or conjugated to a cationic moiety (such as dimethylethanolamine (DMAE)).

Similar to the *Euglena* biomass, the purified beta-1,3-glucan derived from *Euglena* can be orally administered in an edible composition, such as a food product or a dietary supplement, to reduce blood cholesterol levels and/or blood triglyceride levels. The purified beta-1,3-glucan can be provided as a paste, a powder, capsule, tablet, or liquid (such as a suspension), and may be administered by itself or mixed with another food product. For example, the purified beta-1,3-glucan is orally administered in a beverage, such as a nutritional shake, in a nutritional bar, in baked goods, or in a cereal.

Orally administered purified beta-1,3-glucan in a composition can further include one or more added supplements, for example alpha tocopherol, cholecalciferol, zinc, chromium, selenium, arginine, ascorbic acid, alkylglycerol, caffeine, kava kava, *Curcuma longa, Spirulina, Chlorella, stevia*, calcium D-glucarate, coenzyme Q10, peptides, dimethylglycine, docosahexaenoic acid, eicosapentaenoic acid, alpha-lineolenic acid, astaxanthin, beta carotene, lutein, *lactobacillus* probiotics, *bifidobacterium* probiotics, mannoligosaccharide, fructooligosaccharides, *Astragalus, Echinacea*, Esberitox, garlic, glutathione, kelp, L-arginine, L-ornithine, lecithin granules, extracts from maiitake, reishi or shiitake mushrooms, manganese, quercetin, bromelain, olive leaf, *Sambucus*, Umcka, panthothenic acid, quercetin, alpha lipoic acid, essential oils, fish oils, spices and their derivatives, and pterostilbene. Additional components include any of *Haematococcus pluvialis*, astaxanthin, and colostrum.

Purified beta-1,3-glucan can also be used in a pharmaceutical formulation that is administered to a subject, such as a human, to reduce blood cholesterol levels and/or blood triglyceride levels. The pharmaceutical formulation may further comprise a pharmaceutically acceptable excipient. Example pharmaceutically acceptable excipients include fillers, binders, coatings, preservatives, lubricants, flavoring agents, sweetening agents, coloring agents, surfactants, solvents, buffering agents, chelating agents, or stabilizers. Examples of pharmaceutically acceptable fillers include cellulose, dibasic calcium phosphate, calcium carbonate, microcrystalline cellulose, sucrose, lactose, glucose, mannitol, sorbitol, maltitol, pregelatinized starch, corn starch, and potato starch. Examples of pharmaceutically acceptable binders include polyvinylpyrrolidone, starch, lactose, xylitol, sorbitol, maltitol, gelatin, sucrose, polyethylene glycol, methyl cellulose, and cellulose. Examples of pharmaceutically acceptable coatings include hydroxypropyl methylcellulose (HPMC), shellac, corn protein zein, and gelatin. Examples of pharmaceutically acceptable disintegrants include polyvinylpyrrolidone, carboxymethyl cellulose, and sodium starch glycolate. Examples of pharmaceutically acceptable lubricants include polyethylene glycol, magnesium stearate, and stearic acid. Examples of pharmaceutically acceptable preservatives include methyl parabens, ethyl parabens, propyl paraben, benzoic acid, and sorbic acid. Examples of pharmaceutically acceptable sweetening agents include sucrose, saccharine, aspartame, or sorbitol. Examples of pharmaceutically acceptable buffering agents include carbonates, citrates, gluconates, acetates, phosphates, or tartrates.

The pharmaceutical formulation can be orally administered to a subject or intravenously administered to a subject to reduce blood cholesterol levels and/or blood triglyceride levels. Orally administered pharmaceutical formulations can be administered as a solid or a liquid, such as in a tablet, capsule, or syrup. For intravenously administered pharmaceutical formulations, the purified beta-1,3-glucan derived from *Euglena* is suspended or dissolved in an aqueous solution, such as a saline solution.

Administration of effective amounts of an edible composition or a pharmaceutical formulation containing beta-1,3-glucan derived from *Euglena* grown using fermentation can reduce blood serum cholesterol levels after the course of a dosing regimen. For example, the reduction in blood serum cholesterol levels can be measured after 7 days, after 14 days, after 21 days, after 30 days, or after 60 days. In some embodiments, administration of beta-1,3-glucan derived from *Euglena* grown using fermentation results in about 5% decrease or more in blood serum cholesterol levels after 30 days of an effective dose, about 10% decrease or more in blood serum cholesterol levels after 30 days of an effective dose, about 15% decrease or more in blood serum cholesterol levels after 30 days of an effective dose, about 20% decrease or more in blood serum cholesterol levels after 30 days of an effective dose, about 25% decrease or more in blood serum cholesterol levels after 30 days of an effective dose, about 30% decrease or more in blood serum cholesterol levels after 30 days of an effective dose, or about 35% decrease or more in blood serum cholesterol levels after 30 days of an effective dose.

Similarly, administration of effective amounts of an edible composition or a pharmaceutical formulation containing beta-1,3-glucan derived from *Euglena* grown using fermentation can reduce blood serum triglyceride levels after the course of a dosing regimen. In some embodiments, administration of beta-1,3-glucan derived from *Euglena* results in about 5% decrease or more in blood serum triglyceride levels after 30 days of an effective dose, about 10% decrease or more in blood serum triglyceride levels after 30 days of an effective dose, about 15% decrease or more in blood serum triglyceride levels after 30 days of an effective dose, about 20% decrease or more in blood serum triglyceride levels after 30 days of an effective dose, about 25% decrease or more in blood serum triglyceride levels after 30 days of an effective dose, about 30% decrease or more in blood serum triglyceride levels after 30 days of an effective dose, about 35% decrease or more in blood serum triglyceride levels after 30 days of an effective dose, about 40% decrease or more in blood serum triglyceride levels after 30 days of an effective dose, or about 45% decrease or more in blood serum triglyceride levels after 30 days of an effective dose.

Each of the orally administered composition containing beta-1,3-glucan derived from *Euglena* grown using fermentation, the orally administered pharmaceutical formulation containing beta-1,3-glucan derived from *Euglena* grown using fermentation, and the intravenously administered pharmaceutical formulation containing beta-1,3-glucan derived from *Euglena* grown using fermentation are administered in an effective dose to reduce blood serum cholesterol levels and/or blood serum triglyceride levels. Such dosing regimens are generally understood as an amount of beta-1,3-glucan per kg body weight for each of the composition or pharmaceutical formulation. In some embodiments, the composition or pharmaceutical formulation is administered to the subject at an effective amount of about 0.1 mg beta-1,3-glucan per kg body weight or more, about 0.25 mg beta-1,3-glucan per kg body weight or more, about 0.5 mg beta-1,3-glucan per kg body weight or more, about 1 mg beta-1,3-glucan per kg body weight or more, about 2 mg beta-1,3-glucan per kg body weight or more, about 5 mg beta-1,3-glucan per kg body weight or more, about 10 mg beta-1,3-glucan per kg body weight or more, about 15 mg beta-1,3-glucan per kg body weight or more, about 25 mg beta-1,3-glucan per kg body weight or more, or about 50 mg beta-1,3-glucan per kg body weight or more. In some embodiments, the effective amount of the composition or pharmaceutical composition is between about 0.1 mg beta-1,3-glucan per kg body weight and about 50 mg beta-1,3-glucan per kg body weight, between about 0.1 mg beta-1,3-glucan per kg body weight and about 25 mg beta-1,3-glucan per kg body weight, between about 0.2 mg beta-1,3-glucan per kg body weight and about 15 mg beta-1,3-glucan per kg body weight, between about 0.5 mg beta-1,3-glucan per kg body weight and about 10 mg beta-1,3-glucan per kg body weight, or between about 1 mg beta-1,3-glucan per kg body weight and about 10 mg beta-1,3-glucan per kg body weight. As described herein, an effective amount of the composition or pharmaceutical formulation can be administered to the subject once per day. In some embodiments, an effective amount of the composition or pharmaceutical formulation can be administered to a subject as multiple doses per day, for example twice per day or more frequently, three times per day or more frequently, or four times per day or more frequently. In some embodiments, an effective amount of the composition or pharmaceutical formulation can be administered to a subject once per week or more frequently, twice per week or more frequently, three times per week or more frequently, four times per week or more frequently, five times per week or more frequently, or six times per week or more frequently.

In some embodiments, the effective amount of the composition or pharmaceutical composition is between about 0.1 mg beta-1,3-glucan per kg body weight and about 100 mg beta-1,3-glucan per kg body weight, between about 0.1 mg beta-1,3-glucan per kg body weight and about 75 mg beta-1,3-glucan per kg body weight, between about 0.1 mg beta-1,3-glucan per kg body weight and about 50 mg beta-1,3-glucan per kg body weight, between about 0.1 mg beta-1,3-glucan per kg body weight and about 25 mg beta-1,3-glucan per kg body weight, between about 0.2 mg beta-1,3-glucan per kg body weight and about 15 mg beta-1,3-glucan per kg body weight, between about 0.5 mg beta-1,3-glucan per kg body weight and about 10 mg beta-1,3-glucan per kg body weight, between about 1 mg beta-1,3-glucan per kg body weight and about 10 mg beta-1,3-glucan per kg body weight, between about 50 mg beta-1,3-glucan per kg body weight and about 100 mg beta-1,3-glucan per kg body weight, between about 50 mg beta-1,3-glucan per kg body weight and about 75 mg beta-1,3-glucan per kg body weight, or between about 25 mg beta-1,3-glucan per kg body weight and about 75 mg beta-1,3-glucan per kg body weight. As described herein, an effective amount of the composition or pharmaceutical formulation can be administered to the subject once per day. In some embodiments, an effective amount of the composition or pharmaceutical formulation can be administered to a subject as multiple doses per day, for example twice per day or more frequently, three times per day or more frequently, or four times per day or more frequently. In some embodiments, an effective amount of the composition or pharmaceutical formulation can be administered to a subject once per week or more frequently, twice per week or more frequently, three times per week or more frequently, four times per week or more frequently, five times per week or more frequently, or six times per week or more frequently.

An effective amount of the composition or pharmaceutical formulation containing the beta-1,3-glucan derived from *Euglena* grown using fermentation can be administered to the subject to reduce blood serum cholesterol levels and/or blood serum triglyceride levels once per day. In some embodiments, an effective amount of an edible or pharmaceutical composition comprising beta-1,3-glucan derived from *Euglena* grown using fermentation is administered to a subject as multiple doses per day, for example twice per day or more frequently, three times per day or more frequently, or four times per day or more frequently. In some embodiments, an effective amount of an edible or pharmaceutical composition comprising beta-1,3-glucan derived from *Euglena* grown using fermentation is administered to a subject once per week or more frequently, twice per week or more frequently, three times per week or more frequently, four times per week or more frequently, five times per week or more frequently, or six times per week or more frequently.

Methods of Modulating Immune Function

Beta-1,3-glucan derived from *Euglena* (e.g., *Euglena* biomass, beta-1,3-glucan from *Euglena*, or purified beta-1,3-glucan from *Euglena* or combinations thereof) can be administered to a subject, such as a human, to modulate immune function. Administration of the beta-1,3-glucan derived from *Euglena* to the subject results in a measureable increase of cytokine production, antibody titers, and activity of immune system cells (e.g., rates of phagocytosis and natural killer cell cytotoxicity), demonstrating modulated immune function. Subjects administered beta-1,3-glucan derived from *Euglena* also demonstrate an enhanced response to infection.

Beta-1,3-glucan derived from *Euglena* useful for modulating immune function is grown by fermenting the *Euglena* by the methods described herein. The fermented *Euglena* generally rely on a growth media to provide nutrients for growth and production of the beta-1,3-glucan. While it is contemplated that the *Euglena* could grow in full or partial light exposure, it is generally preferred that the *Euglena* grown using fermentation are heterotrophically grown. During fermentation, the growing *Euglena* efficiently produce beta-1,3-glucan. In some embodiments, the *Euglena* cells accumulate beta-1,3-glucan between about 30 wt % to about 70 wt % beta-1,3-glucan, about 30 wt % to about 40 wt % beta-1,3-glucan, about 40 wt % to about 50 wt % beta-1,3-glucan, about 60 wt % to about 70 wt % beta-1,3-glucan, about 40 wt % to about 70 wt % beta-1,3-glucan, or about 50 wt % to about 70 wt % beta-1,3-glucan. In some embodiments, the *Euglena* cells accumulate beta-1,3-glucan between about 50 wt % to about 60 wt % beta-1,3-glucan, or about 50 wt % to about 55 wt % beta-1,3-glucan.

The beta-1,3-glucan derived from *Euglena* and grown using fermentation is administered to a subject for modulating immune function in a purified form or an unpurified form. For example, a *Euglena* biomass grown using fermentation can be orally administered to a subject to modulate immune function. Because the *Euglena* grown using fermentation contains effective amounts of the beta-1,3-glucan, the *Euglena* biomass is effective even without purifying the beta-1,3-glucan. This is due, in part, to the high bioavailability of the beta-1,3-glucan produced by *Euglena*. In contrast, beta glucan produce by yeast is tightly associated with the cell wall of the yeast, and has lower amounts of beta glucan that are readily bioavailable.

The *Euglena* biomass is provided as an edible composition that is orally administered to modulate immune function. The edible composition may be a food product or a dietary supplement. To aid consumption, the *Euglena* biomass can be processed into sheet, a paste, a cream, a powder, a capsule, a tablet, or any other edible solid or liquid (such as a suspension) and consumed by itself or in combination with some other food product. For example, in some embodiments the *Euglena* biomass is administered in a beverage, such as a nutritional shake, in a nutritional bar, in baked goods, or in a cereal.

In one exemplary embodiment, the *Euglena* biomass is dried to prepare it for oral administration. For example, the *Euglena* biomass can be dried by freeze-drying the biomass, heating the biomass, or applying a vacuum to the biomass to a moisture content of about 40% or less, about 30% or less, about 25% or less, about 20% or less, about 15% or less, about 10% or less, about 5% or less, about 4% or less, about 3% or less, about 2% or less, or about 1% or less. Optionally, either before or after drying the *Euglena* biomass, it can be processed into a powder. For example, the *Euglena* cells are suspended in solution, pulverized by a shear mixer, and dried to produce the powder. The powdered *Euglena* biomass can processed to have an average particle size of about 1000 microns or less, about 900 microns or less, about 800 microns or less, about 700 microns or less, about 600 microns or less, about 500 microns or less, about 400 microns or less, about 300 microns or less, about 250 microns or less, about 200 microns or less, about 100 microns or less, about 50 microns or less, about 25 microns or less, about 15 microns or less, about 10 microns or less, about 5 microns or less, about 3 microns or less, about 2 microns or less, about 1 micron or less, or about 0.5 microns or less. The dried and/or powdered *Euglena* biomass can then be orally administered to the subject, either directly or by mixing with another edible composition, to modulate the immune function of the subject.

The orally administered *Euglena* biomass can further include nutritional supplements in addition to the beta-1,3-glucan. The nutritional supplements may be pre-existing in the *Euglena* biomass or may be added to the *Euglena* biomass. Exemplary additional supplements include alpha tocopherol, cholecalciferol, zinc, chromium, selenium, arginine, ascorbic acid, alkylglycerol, caffeine, kava kava, *Curcuma longa, Spirulina, Chlorella, stevia*, calcium D-glucarate, coenzyme Q10, peptides, dimethylglycine, docosahexaenoic acid, eicosapentaenoic acid, alpha-lineolenic acid, astaxanthin, beta carotene, lutein, *lactobacillus* probiotics, *bifidobacterium* probiotics, mannoligosaccharide, fructooligosaccharides, *Astragalus, Echinacea*, Esberitox, garlic, glutathione, kelp, L-arginine, L-ornithine, lecithin granules, extracts from maiitake, reishi or shiitake mushrooms, manganese, quercetin, bromelain, olive leaf, *Sambucus*, Umcka, panthothenic acid, quercetin, alpha lipoic acid, essential oils, fish oils, spices and their derivatives, and pterostilbene. These additional supplements can function independently of, or synergistically with, the beta-1,3-glucan derived from *Euglena* grown using fermentation to modulate immune function. Additional components include any of *Haematococcus pluvialis*, astaxanthin, and colostrum.

The orally administered *Euglena* biomass may further comprise a pharmaceutically acceptable excipient. Example pharmaceutically acceptable excipients include fillers, binders, coatings, preservatives, lubricants, flavoring agents, sweetening agents, coloring agents, surfactants, solvents, buffering agents, chelating agents, or stabilizers. Examples of pharmaceutically acceptable fillers include cellulose, dibasic calcium phosphate, calcium carbonate, microcrystalline cellulose, sucrose, lactose, glucose, mannitol, sorbitol, maltitol, pregelatinized starch, corn starch, and potato starch. Examples of pharmaceutically acceptable binders include polyvinylpyrrolidone, starch, lactose, xylitol, sorbitol, maltitol, gelatin, sucrose, polyethylene glycol, methyl cellulose, and cellulose. Examples of pharmaceutically acceptable coatings include hydroxypropyl methylcellulose (HPMC), shellac, corn protein zein, and gelatin. Examples of pharmaceutically acceptable disintegrants include polyvinylpyrrolidone, carboxymethyl cellulose, and sodium starch glycolate. Examples of pharmaceutically acceptable lubricants include polyethylene glycol, magnesium stearate, and stearic acid. Examples of pharmaceutically acceptable preservatives include methyl parabens, ethyl parabens, propyl paraben, benzoic acid, and sorbic acid. Examples of pharmaceutically acceptable sweetening agents include sucrose, saccharine, aspartame, or sorbitol. Examples of pharmaceutically acceptable buffering agents include carbonates, citrates, gluconates, acetates, phosphates, or tartrates.

Beta-1,3-glucan derived from *Euglena* grown using fermentation can also be administered in a purified form to a subject to modulate function. In some embodiments, beta-1,3-glucan is purified from *Euglena* to be more than 85% pure, more than 90% pure, more than 92% pure, more than 94% pure, more than 95% pure, more than 96% pure, more than 97% pure, more than 98% pure, or more than 99% pure. Generally, the beta-1,3-glucan is extracted by lysing the *Euglena* cells and isolating the beta-1,3-glucan. The *Euglena* cells can be lysed using sonication or high pressure homogenization. Optionally, additional chemicals are included during the lysis step to aid the lysis, but such chemicals are not necessarily required. Exemplary additional chemical included during the lysis step include detergents (such as sodium dodecyl sulfate), enzymes, bases (such as sodium hydroxide), or acids (such as acetic acid or hydrochloric acid). The beta-1,3-glucan can be isolated from the lysed *Euglena* cells using filtration or gravity separation (such as gravity settling or centrifugation). To obtain higher levels of purity, the isolated beta-1,3-glucan is washed, for example with an aqueous solution or ethanol.

Purified beta-1,3-glucan can also be modified to increase its potency as a modulator of immune function. For example, the beta-1,3-glucan can be sulfated, conjugated to pyridinium moiety, or conjugated to a cationic moiety (such as dimethylethanolamine (DMAE)).

Similar to the *Euglena* biomass, the purified beta-1,3-glucan derived from *Euglena* can be orally administered to modulate immune function in an edible composition, such as a food product or a dietary supplement. The purified beta-1,3-glucan can be provided as a paste, a powder, capsule, tablet, or liquid (such as a suspension), and may be administered by itself or mixed with another food product. For example, the purified beta-1,3-glucan can be orally administered in a beverage, such as a nutritional shake, in a nutritional bar, in baked goods, or in a cereal.

Orally administered purified beta-1,3-glucan in a composition can further include one or more added supplements, for example alpha tocopherol, cholecalciferol, zinc, chromium, selenium, arginine, ascorbic acid, alkylglycerol, caffeine, kava kava, *Curcuma longa, Spirulina, Chlorella, stevia*, calcium D-glucarate, coenzyme Q10, peptides, dimethylglycine, docosahexaenoic acid, eicosapentaenoic acid, alpha-lineolenic acid, astaxanthin, beta carotene, lutein, *lactobacillus* probiotics, *bifidobacterium* probiotics, mannoligosaccharide, fructooligosaccharides, *Astragalus, Echinacea*, Esberitox, garlic, glutathione, kelp, L-arginine, L-ornithine, lecithin granules, extracts from maiitake, reishi or shiitake mushrooms, manganese, quercetin, bromelain, olive leaf, *Sambucus*, Umcka, panthothenic acid, quercetin, alpha lipoic acid, essential oils, fish oils, spices and their derivatives, and pterostilbene. Additional components include any of *Haematococcus pluvialis*, astaxanthin, and colostrum.

Purified beta-1,3-glucan can also be used in a pharmaceutical formulation that is administered to a subject, such as a human, to modulate immune function. The pharmaceutical formulation may further comprise a pharmaceutically acceptable excipient. Example pharmaceutically acceptable excipients include fillers, binders, coatings, preservatives, lubricants, flavoring agents, sweetening agents, coloring agents, surfactants, solvents, buffering agents, chelating agents, or stabilizers. Examples of pharmaceutically acceptable fillers include cellulose, dibasic calcium phosphate, calcium carbonate, microcrystalline cellulose, sucrose, lactose, glucose, mannitol, sorbitol, maltitol, pregelatinized starch, corn starch, and potato starch. Examples of pharmaceutically acceptable binders include polyvinylpyrrolidone, starch, lactose, xylitol, sorbitol, maltitol, gelatin, sucrose, polyethylene glycol, methyl cellulose, and cellulose. Examples of pharmaceutically acceptable coatings include hydroxypropyl methylcellulose (HPMC), shellac, corn protein zein, and gelatin. Examples of pharmaceutically acceptable disintegrants include polyvinylpyrrolidone, carboxymethyl cellulose, and sodium starch glycolate. Examples of pharmaceutically acceptable lubricants include polyethylene glycol, magnesium stearate, and stearic acid. Examples of pharmaceutically acceptable preservatives include methyl parabens, ethyl parabens, propyl paraben, benzoic acid, and sorbic acid. Examples of pharmaceutically acceptable sweetening agents include sucrose, saccharine, aspartame, or sorbitol. Examples of pharmaceutically acceptable buffering agents include carbonates, citrates, gluconates, acetates, phosphates, or tartrates.

The pharmaceutical formulation can be orally administered to a subject or intravenously administered to a subject to modulate immune function. Alternate routes of administration, such as by inhalation, are also contemplated. Orally administered pharmaceutical formulations can be administered as a solid or a liquid, such as in a tablet, capsule, or syrup. For intravenously administered pharmaceutical formulations, the purified beta-1,3-glucan derived from *Euglena* is suspended or dissolved in an aqueous solution, such as a saline solution. The pharmaceutical formulation suitable for inhalation may be administered by, for example, a nasal spray. The edible composition or pharmaceutical formulation can be administered in combination with one or more drugs to enhance the treatment of allergies, diabetes, or infection. For example, the edible composition or pharmaceutical formulation can be administered in combination with anti-histamines, insulin, or antibiotics.

Modulating the immune function of a subject by administering an effective amount of beta-1,3-glucan derived from *Euglena* grown using fermentation, such as by administering an edible composition or a pharmaceutical formulation described herein, provides a number of health benefits. The compositions and formulations containing beta-1,3-glucan derived from *Euglena* can be administered to modulate an immune function for the treatment of a disease or for prophylactic treatment. For example, administration of the composition or pharmaceutical formulation can be used to modulate an autoimmune response in a subject, modulate blood sugar levels in a subject, modulate an infection in a subject, or modulate inflammation in a subject.

The compositions or pharmaceutical formulations containing the beta-1,3-glucans derived from *Euglena* (e.g., *Euglena* biomass, beta-1,3-glucan from *Euglena*, or purified beta-1,3-glucan from *Euglena* or combinations thereof) can be administered to a subject, including a human, to modulate an autoimmune response associated with diabetes, Crohn's disease, rheumatoid arthritis, fibromyalgia, systemic lupus erythematosus, glomerulonephritis, scleroderma, or multiple sclerosis. In some embodiments, the edible composition or pharmaceutical composition is prophylactically administered to limit the progression of diabetes, Crohn's disease, rheumatoid arthritis, fibromyalgia, systemic lupus erythematosus, glomerulonephritis, scleroderma, or multiple sclerosis.

The compositions or pharmaceutical formulations containing beta-1,3-glucans derived from *Euglena* grown using fermentation (e.g., *Euglena* biomass, beta-1,3-glucan from *Euglena*, or purified beta-1,3-glucan from *Euglena* or combinations thereof) as described herein can also be administered to a subject to modulate blood sugar levels in the subject. After administration of the compositions or pharmaceutical formulations containing beta-1,3-glucans, postprandial blood sugars are generally lower than without the administration of the beta-1,3-glucan. The modulation of blood sugars, particularly postprandial blood sugars, is important for general diabetes care and management in both Type I and Type II diabetics. Blood sugar levels can be measured using the A1C test, which reflects average blood sugar levels of the past two to three months. Specifically, the A1C test measures the percentage of hemoglobin that is coated with sugar (i.e. glycated). The compositions and pharmaceutical compositions containing beta-1,3-glucans derived from *Euglena* as described herein are therefore useful to treat hyperglycemia in a diabetic. In some embodiments, edible compositions or pharmaceutical formulations containing beta-1,3-glucans derived from *Euglena* as described herein are prophylactically administered to a subject to limit hyperglycemia.

Beta-1,3-glucan derived from *Euglena* grown using fermentation (e.g., *Euglena* biomass, beta-1,3-glucan from *Euglena*, or purified beta-1,3-glucan from *Euglena* or combinations thereof) in compositions or pharmaceutical formulations can also be administered to a subject to modulate an infection, such as a bacterial infection, a fungal infection, or a viral infection, in a subject. Administration of compositions or pharmaceutical formulations containing the beta-1,3-glucan described herein results in increased activity of both innate and adaptive immune functions. For example, administration of the compositions or pharmaceutical formulations results an increase in phagocytizing neutrophils, natural killer cell cytotoxicity, and antibody production. Each of these modulated immune functions affects infections. The compositions or pharmaceutical formulations containing the beta-1,3-glucan derived from *Euglena* grown by fermentation can be administered to a subject that has an infection to treat the infection, or prophylactically administered to a subject to limit the risk of infection. These advances in the treatment or prophylactic treatment of infection are particularly important for bacterial infections, due to the risk of antibiotic resistant bacteria, including methicillin-resistant *Staphylococcus aureus* (MRSA).

Administration of compositions or pharmaceutical formulations comprising beta-1,3-glucans derived from *Euglena* grown using fermentation (e.g., *Euglena* biomass, beta-1,3-glucan from *Euglena*, or purified beta-1,3-glucan from *Euglena* or combinations thereof) as described herein can be administered to a subject, including a human, to modulate inflammation in the subject. The administered beta-1,3-glucan functions to suppress the production of inflammatory cytokines, resulting in a modulated inflammatory response in the subject. In some embodiments, the inflammation is associated with allergies or asthma. The compositions or pharmaceutical formulations comprising beta-1,3-glucans derived from *Euglena* as described herein can be administered to a subject to treat inflammation, such as allergies or asthma. Additionally, the compositions or pharmaceutical formulations comprising beta-1,3-glucans derived from *Euglena* as described herein can be prophylactically administered to a subject to limit inflammation, such as allergies or asthma.

Each of the orally administered composition containing beta-1,3-glucan derived from *Euglena* grown using fermentation, the orally administered pharmaceutical formulation containing beta-1,3-glucan derived from *Euglena* grown using fermentation, and the intravenously administered pharmaceutical formulation containing beta-1,3-glucan derived from *Euglena* grown using fermentation are administered in an effective dose to modulate immune function. Such dosing regimens are generally understood as an amount of beta-1,3-glucan per kg body weight for each of the composition or pharmaceutical formulation. In some embodiments, the composition or pharmaceutical formulation is administered to the subject at an effective amount of about 0.1 mg beta-1,3-glucan per kg body weight or more, about 0.25 mg beta-1,3-glucan per kg body weight or more, about 0.5 mg beta-1,3-glucan per kg body weight or more, about 1 mg beta-1,3-glucan per kg body weight or more, about 2 mg beta-1,3-glucan per kg body weight or more, about 5 mg beta-1,3-glucan per kg body weight or more, about 10 mg beta-1,3-glucan per kg body weight or more, about 15 mg beta-1,3-glucan per kg body weight or more, about 25 mg beta-1,3-glucan per kg body weight or more, or about 50 mg beta-1,3-glucan per kg body weight or more. In other embodiments, the effective amount of the composition or pharmaceutical composition used to modulate the immune function of the subject, to treat a disease, or for prophylactic administration can be is between about 0.1 mg beta-1,3-glucan per kg body weight and about 50 mg beta-1,3-glucan per kg body weight, between about 0.1 mg beta-1,3-glucan per kg body weight and about 25 mg beta-1,3-glucan per kg body weight, between about 0.2 mg beta-1,3-glucan per kg body weight and about 15 mg beta-1,3-glucan per kg body weight, between about 0.5 mg beta-1,3-glucan per kg body weight and about 10 mg beta-1,3-glucan per kg body weight, or between about 1 mg beta-1,3-glucan per kg body weight and about 10 mg beta-1,3-glucan per kg body weight. As described herein, an effective amount of the composition or pharmaceutical formulation can be administered to the subject once per day. In some embodiments, an effective amount of the composition or pharmaceutical formulation can be administered to a subject as multiple doses per day, for example twice per day or more frequently, three times per day or more frequently, or four times per day or more frequently. In some embodiments, an effective amount of the composition or pharmaceutical formulation can be administered to a subject once per week or more frequently, twice per week or more frequently, three times per week or more frequently, four times per week or more frequently, five times per week or more frequently, or six times per week or more frequently.

In some embodiments, the effective amount of the composition or pharmaceutical composition is between about 0.1 mg beta-1,3-glucan per kg body weight and about 100 mg beta-1,3-glucan per kg body weight, between about 0.1 mg beta-1,3-glucan per kg body weight and about 75 mg beta-1,3-glucan per kg body weight, between about 0.1 mg beta-1,3-glucan per kg body weight and about 50 mg beta-1,3-glucan per kg body weight, between about 0.1 mg beta-1,3-glucan per kg body weight and about 25 mg beta-1,3-glucan per kg body weight, between about 0.2 mg beta-1,3-glucan per kg body weight and about 15 mg beta-1,3-glucan per kg body weight, between about 0.5 mg beta-1,3-glucan per kg body weight and about 10 mg beta-1,3-glucan per kg body weight, between about 1 mg beta-1,3-glucan per kg body weight and about 10 mg beta-1,3-glucan per kg body weight, between about 50 mg beta-1,3-glucan per kg body weight and about 100 mg beta-1,3-glucan per kg body weight, between about 50 mg beta-1,3-glucan per kg body weight and about 75 mg beta-1,3-glucan per kg body weight, or between about 25 mg beta-1,3-glucan per kg body weight and about 75 mg beta-1,3-glucan per kg body weight. As described herein, an effective amount of the composition or pharmaceutical formulation can be administered to the subject once per day. In some embodiments, an effective amount of the composition or pharmaceutical formulation can be administered to a subject as multiple doses per day, for example twice per day or more frequently, three times per day or more frequently, or four times per day or more frequently. In some embodiments, an effective amount of the composition or pharmaceutical formulation can be administered to a subject once per week or more frequently, twice per week or more frequently, three times per week or more frequently, four times per week or more frequently, five times per week or more frequently, or six times per week or more frequently.

An effective amount of the composition or pharmaceutical formulation containing the beta-1,3-glucan derived from *Euglena* grown using fermentation can be administered to the subject to modulate immune function once per day. In some embodiments, an effective amount of an edible or pharmaceutical composition comprising beta-1,3-glucan derived from *Euglena* grown using fermentation is administered to a subject as multiple doses per day, for example twice per day or more frequently, three times per day or more frequently, or four times per day or more frequently. In some embodiments, an effective amount of an edible or pharmaceutical composition comprising beta-1,3-glucan derived from *Euglena* grown using fermentation is administered to a subject once per week or more frequently, twice per week or more frequently, three times per week or more frequently, four times per week or more frequently, five times per week or more frequently, or six times per week or more frequently.

Methods of Treating Intestinal Inflammation

Inflammation can be modulated by beta-1,3-glucans. In a recent study, oral administration of paramylon, a beta-1,3-glucan derived from *Euglena*, was found to inhibit the development of atopic dermatitis-like skin lesions in mice (*J. Vet. Med. Sci.* 2010, 72(2), 755-763). In humans, atopic dermatitis is a common skin disease characterized by chronic and relapsing inflammation of the skin, resulting in itchy, red, swollen, and cracked skin. The exact cause of atopic dermatitis is unknown, although likely factors include genetics, immune system dysfunction, and environmental exposures. The authors of the mouse study found that oral administration of paramylon reduced IL-4 and IFN-γ levels in the serum, and also reduced IL-18 and IL-12 levels in the skin lesions. These results suggest that purified beta-1,3-glucan derived from *Euglena* may inhibit atopic dermatitis-like skin lesions in mice by activation of certain cytokine pathways. However, the exact mechanism by which beta-1,3-glucan modulates inflammation in general remains to be elucidated. In addition, beta-1,3-glucan may modulate inflammation of different body organs by different pathways.

Intestinal inflammation can affect all or part of the digestive tract. Intestinal inflammation is a type of autoimmune disease and refers to inflammation of the small intestine, the large intestine, the bowel, or any combination thereof. Symptoms of intestinal inflammation include severe or chronic abdominal pain, diarrhea, sudden weight loss, lack of appetite, and rectal bleeding. In addition, an individual having intestinal inflammation may also have symptoms unrelated to the gastrointestinal tract such as joint pain, skin rashes, eye pain, mouth sores, and fever. Intestinal inflammation may lead to life-threatening complications, as well as increase an individual's risk for colon cancer. The exact underlying physiological cause of intestinal inflammation is unknown, but genetic and environmental factors are generally believed to shift an individual's immune response such that an abnormal immune response results.

Inflammatory bowel disease is a group of inflammatory conditions of the large and small intestine that include colitis and Crohn's disease. Crohn's disease affects the full thickness of the bowel wall, whereas colitis is restricted to the epithelial lining of the colon. Specific examples of colitis include ulcerative colitis, macroscopic colitis, lymphocytic colitis, collagenous colitis, diversion colitis, chemical colitis, ischemic colitis, and infection colitis. As discussed herein, the use of beta-1,3-glucan to treat intestinal inflammation refers equally to the use of beta-1,3-glucan to treat inflammatory bowel disease, colitis, and Crohn's disease. As also discussed herein, the use of beta-1,3-glucan to treat intestinal inflammation refers equally to the use of beta-1,3-glucan to prophylactically treat intestinal inflammation. Similarly, as discussed herein, the use of beta-1,3-glucan to prophylactically treat intestinal inflammation refers equally to the use of beta-1,3-glucan to prophylactically treat inflammatory bowel disease, colitis, and Crohn's disease.

Ulcerative colitis is one of the major forms of inflammatory bowel disease (IBD). It is a chronic disease that causes inflammation and ulcers on the inner lining of the colon. While the other major form, Crohn's disease, most commonly affects the end of the small bowel (the ileum) and the beginning of the colon, ulcerative colitis is typically limited to the colon. Ulcerative colitis most often progresses slowly and can become worse over time. Symptoms can be mild to severe. Most people have periods of remission that can last for weeks or years. While there is no ideal animal model for studying human colitis, among the various chemically induced colitis animal models, the dextran sulfate sodium (DSS)-induced colitis model is the most widely used because of its simplicity and many similarities primarily with human ulcerative colitis. (*Comp. Clin. Pathol.* 2010, 19, 235-239).

DSS mainly affects the large intestine and particularly the middle and distal third of the colon. Disruption of the intestinal epithelial barrier and thereby the entry of luminal bacteria or bacterial antigens into the mucosa and immune activation are major events in human colitis. A similar phenomenon occurs in DSS colitis, but in this case a sulfated polysaccharide that is directly toxic to colonic epithelium causes epithelial cell injury and the resulting immune responses alter mucosal barrier function throughout the colonic epithelium. Administration of DSS to mice in their drinking water for a short period of time results in the induction of a very reproducible acute inflammation limited to the colon and characterized by ulcers, loss of crypts, and infiltration of granulocytes. The DSS colitis model has also been used extensively to study colon cancer developing in relation to colonic inflammation, such as that occurring in patients with long-standing ulcerative colitis. Even though DSS-induced colitis is caused primarily by disruption of the epithelium and activation of macrophages and neutrophils in the absence of adaptive immunity, T-cell responses can aggravate the inflammatory response. In fact, a strong T cell response has been implicated in human ulcerative colitis. Therefore, positive therapeutic outcomes for a composition or pharmaceutical tested in rodents using the DSS model may suggest a therapeutic value for the treatment of human ulcerative colitis. Importantly, if an agent has anti-inflammatory properties and produces protection from DSS-induced colitis, then that agent may have therapeutic value in other IBDs.

Beta-1,3-glucan derived from *Euglena* grown using fermentation (e.g., *Euglena* biomass, beta-1,3-glucan from *Euglena*, or purified beta-1,3-glucan from *Euglena* or combinations thereof) can be administered to a subject, including a human, to treat intestinal inflammation or prophylactically administered to a subject at risk for intestinal inflammation. Beta-1,3-glucan derived from *Euglena* grown using fermentation can be administered to a subject, including a human, to treat inflammatory bowel disease. Beta-1,3-glucan derived from *Euglena* grown using fermentation can be administered to a subject, including a human, to treat colitis. Beta-1,3-glucan derived from *Euglena* grown using fermentation can be administered to a subject, including a human, to treat Crohn's disease. A person at risk for intestinal inflammation can include, but is not limited to, a person who has been previously diagnosed with intestinal inflammation, or a person with one or more parents with intestinal inflammation.

As described herein, administration of beta-1,3-glucan derived from *Euglena* grown using fermentation protects from chemically-induced colitis (see Examples 12-19). Such administration can be oral, such as by administering an edible composition or an oral pharmaceutical formulation, or intravenous, such as by administering an intravenous pharmaceutical formulation. Alternate routes of administration, such as by inhalation, are also contemplated. The oral edible composition or oral pharmaceutical formulation includes either purified or non-purified beta-1,3-glucans derived from *Euglena* grown using fermentation as described herein. Generally, the intravenous pharmaceutical formulation includes purified beta-1,3-glucans derived from *Euglena* grown using fermentation. Typically, the pharmaceutical formulation suitable for inhalation includes purified beta-1,3-glucans derived from *Euglena* grown using fermentation and may be administered by, for example, a nasal spray. The edible composition or pharmaceutical formulation can be administered in combination with one or more anti-inflammatory drugs, immunosuppression drugs, or antibiotics to enhance the treatment of intestinal inflammation. Examples of suitable drugs include, but are not limited to, mesalamine, budesonide, cyclosporine, and infliximab.

The fermented *Euglena* useful to produce the beta-1,3-glucan for the treatment of intestinal inflammation generally rely on a growth medium to provide nutrients for growth and production of the beta-1,3-glucan. While it is contemplated that the *Euglena* could grow in full or partial light exposure, it is generally preferred that the *Euglena* grown using fermentation are heterotrophically grown. During fermentation, the growing *Euglena* efficiently produce beta-1,3-glucan. In some embodiments, the *Euglena* cells accumulate beta-1,3-glucan between about 30 wt % to about 70 wt % beta-1,3-glucan, about 30 wt % to about 40 wt % beta-1,3-glucan, about 40 wt % to about 50 wt % beta-1,3-glucan, about 60 wt % to about 70 wt % beta-1,3-glucan, about 40 wt % to about 70 wt % beta-1,3-glucan, or about 50 wt % to about 70 wt % beta-1,3-glucan. In some embodiments, the *Euglena* cells accumulate beta-1,3-glucan between about 50 wt % to about 60 wt % beta-1,3-glucan, or about 50 wt % to about 55 wt % beta-1,3-glucan.

The beta-1,3-glucan derived from *Euglena* and grown using fermentation is administered to a subject for treating intestinal inflammation in a purified form or in an unpurified form. For example, a *Euglena* biomass grown using fermentation can be orally administered to a subject to treat intestinal inflammation. Because the *Euglena* grown using fermentation contain effective amounts of the beta-1,3-glucan, the *Euglena* biomass is effective for treating intestinal inflammation even without purifying the beta-1,3-glucan. This is due, in part, to the high bioavailability of the beta-1,3-glucan produced by *Euglena* grown by fermentation. Specifically, beta-1,3-glucan derived from *Euglena* accumulates in water-insoluble granules and is not associate with cell wall components. In contrast, beta glucan produce by yeast is tightly associated with the cell wall of the yeast, and has lower amounts of bioavailable beta glucan. In some embodiments, dried *Euglena* biomass containing unpurified beta-1,3-glucan is more effective than purified beta-1,3-glucan for treating intestinal inflammation in a subject using the methods described herein.

The *Euglena* biomass is provided in an edible composition that is orally administered to treat intestinal inflammation. The edible composition may be a food product or a dietary supplement. To aid consumption, the *Euglena* biomass can be processed into a sheet, a paste, a cream, a powder, a capsule, a tablet, or any other edible solid or liquid (such as a suspension) and consumed by itself or in combination with another food product. For example, in some embodiments the *Euglena* biomass is administered in a beverage, such as a nutritional shake, in a nutritional bar, in baked goods, or in a cereal.

In one exemplary embodiment, the *Euglena* biomass is dried to prepare it for oral administration. For example, the *Euglena* biomass can be dried by freeze-drying the biomass, heating the biomass in an oven, double drum dryer, or similar drying device, or applying a vacuum to the biomass to a moisture content of about 40% or less, about 30% or less, about 25% or less, about 20% or less, about 15% or less, about 10% or less, about 5% or less, about 4% or less, about 3% or less, about 2% or less, or about 1% or less. Optionally, during or after drying the *Euglena* biomass, the biomass is processed into a powder. For example, the *Euglena* cells are dried and then pulverized by a shear mixer or hammer mill to produce the powder. In some embodiments, the powdered *Euglena* biomass is processed to an average particle size of about 1000 microns or less, about 900 microns or less, about 800 microns or less, about 700 microns or less, about 600 microns or less, about 500 microns or less, about 400 microns or less, about 300 microns or less, about 250 microns or less, about 200 microns or less, about 100 microns or less, about 50 microns or less, about 25 microns or less, about 15 microns or less, about 10 microns or less, about 5 microns or less, about 3 microns or less, about 2 microns or less, about 1 micron or less, or about 0.5 microns or less. In some embodiments, the *Euglena* cells are disrupted or lysed prior to drying the *Euglena* biomass. For example, the *Euglena* cells can be suspended in an aqueous solution prior to drying, exposed to high shear forces that break apart the cells, and then dried. Optionally, the dried biomass can be further milled as described above to achieve an average particle size of about 1000 microns or less. The dried and/or powdered *Euglena* biomass can then be orally administered to a subject, either directly or by mixing with another edible composition, to treat intestinal inflammation in the subject.

The orally administered *Euglena* biomass can further include nutritional supplements in addition to the beta-1,3-glucan. The nutritional supplements may be pre-existing in the *Euglena* biomass or may be added to the *Euglena* biomass. For example, additional supplements may include metals, amino acids, enzymes, probiotics, fatty acids, oligosaccharides, vitamins, and immune stimulating substances. Exemplary additional supplements include alpha tocopherol, cholecalciferol, zinc, chromium, selenium, arginine, ascorbic acid, alkylglycerol, caffeine, kava kava, *Curcuma longa, Spirulina, Chlorella*, stevia, calcium D-glucarate, coenzyme Q10, peptides, dimethylglycine, docosahexaenoic acid, eicosapentaenoic acid, alpha-linolenic acid, astaxanthin, beta carotene, lutein, *lactobacillus* probiotics, *bifidobacterium* probiotics, mannoligosaccharide, fructooligosaccharides, *Astragalus, Echinacea*, Esberitox, garlic, glutathione, kelp, L-arginine, L-ornithine, lecithin granules, extracts from maiitake, reishi or shiitake mushrooms, manganese, quercetin, bromelain, olive leaf, *Sambucus*, Umcka, panthothenic acid, quercetin, alpha lipoic acid, essential oils, fish oils, spices and their derivatives, and pterostilbene. These additional supplements can function independently of, or synergistically with, the beta-1,3-glucan derived from *Euglena* grown using fermentation to treat intestinal inflammation. Additional components include any of *Haematococcus pluvialis*, astaxanthin, and colostrum.

The orally administered *Euglena* biomass may further comprise a pharmaceutically acceptable excipient. Example pharmaceutically acceptable excipients include fillers, binders, coatings, preservatives, lubricants, flavoring agents, sweetening agents, coloring agents, surfactants, solvents, buffering agents, chelating agents, or stabilizers. Examples of pharmaceutically acceptable fillers include cellulose, dibasic calcium phosphate, calcium carbonate, microcrystalline cellulose, sucrose, lactose, glucose, mannitol, sorbitol, maltitol, pregelatinized starch, corn starch, and potato starch. Examples of pharmaceutically acceptable binders include polyvinylpyrrolidone, starch, lactose, xylitol, sorbitol, maltitol, gelatin, sucrose, polyethylene glycol, methyl cellulose, and cellulose. Examples of pharmaceutically acceptable coatings include hydroxypropyl methylcellulose (HPMC), shellac, corn protein zein, and gelatin. Examples of pharmaceutically acceptable disintegrants include polyvinylpyrrolidone, carboxymethyl cellulose, and sodium starch glycolate. Examples of pharmaceutically acceptable lubricants include polyethylene glycol, magnesium stearate, and stearic acid. Examples of pharmaceutically acceptable preservatives include methyl parabens, ethyl parabens, propyl paraben, benzoic acid, and sorbic acid. Examples of pharmaceutically acceptable sweetening agents include sucrose, saccharine, aspartame, and sorbitol. Examples of pharmaceutically acceptable buffering agents include carbonates, citrates, gluconates, acetates, phosphates, and tartrates.

Beta-1,3-glucan derived from *Euglena* grown using fermentation can also be administered to a subject to treat intestinal inflammation in a purified form. In some embodiments, beta-1,3-glucan is purified from *Euglena* to be more than 85% pure, more than 90% pure, more than 92% pure, more than 94% pure, more than 95% pure, more than 96% pure, more than 97% pure, more than 98% pure, or more than 99% pure. Generally, the beta-1,3-glucan is extracted by lysing the *Euglena* cells and isolating the beta-1,3-glucan. The *Euglena* cells can be lysed using sonication or high pressure homogenization. Optionally, additional chemicals are included during the lysis step to aid the lysis, but such chemicals are not necessarily required. Exemplary additional chemicals included during the lysis step include detergents (such as sodium dodecyl sulfate), enzymes, bases (such as sodium hydroxide), or acids (such as acetic acid or hydrochloric acid). The beta-1,3-glucan can be isolated from the lysed *Euglena* cells using filtration or gravity separation (such as gravity settling or centrifugation). To obtain higher levels of purity, the isolated beta-1,3-glucan is washed, for example with an aqueous solution or ethanol.

Purified beta-1,3-glucan can also be modified to increase its potency in treating intestinal inflammation. For example, the beta-1,3-glucan can be sulfated, conjugated to pyridinium moiety, or conjugated to a cationic moiety (such as dimethylethanolamine (DMAE)).

Similar to the *Euglena* biomass, the purified beta-1,3-glucan derived from *Euglena* can be orally administered in an edible composition, such as a food product or a dietary supplement, to treating intestinal inflammation. The purified beta-1,3-glucan can be provided as a paste, a gel, a powder, capsule, tablet, or liquid (such as a suspension), and may be administered by itself or mixed with another food product. For example, the purified beta-1,3-glucan is orally administered in a beverage, such as a nutritional shake, in a nutrional bar, in baked goods, or in a cereal.

Orally administered purified beta-1,3-glucan in a composition can further include one or more added supplements, for example alpha tocopherol, cholecalciferol, zinc, chromium, selenium, arginine, ascorbic acid, alkylglycerol, caffeine, kava kava, *Curcuma longa, Spirulina, Chlorella, stevia*, calcium D-glucarate, coenzyme Q10, peptides, dimethylglycine, docosahexaenoic acid, eicosapentaenoic acid, alpha-lineolenic acid, astaxanthin, beta carotene, lutein, *lactobacillus* probiotics, *bifidobacterium* probiotics, mannoligosaccharide, fructooligosaccharides, *Astragalus, Echinacea*, Esberitox, garlic, glutathione, kelp, L-arginine, L-ornithine, lecithin granules, extracts from maiitake, reishi or shiitake mushrooms, manganese, quercetin, bromelain, olive leaf, *Sambucus*, Umcka, panthothenic acid, quercetin, alpha lipoic acid, essential oils, fish oils, spices and their derivatives, and pterostilbene. Additional components include any of *Haematococcus pluvialis*, astaxanthin, and colostrum.

Purified beta-1,3-glucan can also be used in a pharmaceutical formulation that is administered to a subject, such as a human, to treat intestinal inflammation. The pharmaceutical formulation may further comprise a pharmaceutically acceptable excipient. Example pharmaceutically acceptable excipients include fillers, binders, coatings, preservatives, lubricants, flavoring agents, sweetening agents, coloring agents, surfactants, solvents, buffering agents, chelating agents, or stabilizers. Examples of pharmaceutically acceptable fillers include cellulose, dibasic calcium phosphate, calcium carbonate, microcrystalline cellulose, sucrose, lactose, glucose, mannitol, sorbitol, maltitol, pregelatinized starch, corn starch, and potato starch. Examples of pharmaceutically acceptable binders include polyvinylpyrrolidone, starch, lactose, xylitol, sorbitol, maltitol, gelatin, sucrose, polyethylene glycol, methyl cellulose, and cellulose. Examples of pharmaceutically acceptable coatings include hydroxypropyl methylcellulose (HPMC), shellac, corn protein zein, and gelatin. Examples of pharmaceutically acceptable disintegrants include polyvinylpyrrolidone, carboxymethyl cellulose, and sodium starch glycolate. Examples of pharmaceutically acceptable lubricants include polyethylene glycol, magnesium stearate, and stearic acid. Examples of pharmaceutically acceptable preservatives include methyl parabens, ethyl parabens, propyl paraben, benzoic acid, and sorbic acid. Examples of pharmaceutically acceptable sweetening agents include sucrose, saccharine, aspartame, and sorbitol. Examples of pharmaceutically acceptable buffering agents include carbonates, citrates, gluconates, acetates, phosphates, and tartrates.

The pharmaceutical formulation can be orally administered to a subject or intravenously administered to a subject to treat intestinal inflammation. Orally administered pharmaceutical formulations can be administered as a solid or a liquid, such as in a tablet, capsule, or syrup. For intravenously administered pharmaceutical formulations, the purified beta-1,3-glucan derived from *Euglena* is suspended or dissolved in an aqueous solution, such as a saline solution.

Administration of effective amounts of an edible composition or a pharmaceutical formulation containing beta-1,3-glucan derived from *Euglena* grown using fermentation can treat intestinal inflammation after the course of a dosing regimen. For example, the reduction in symptoms associated with intestinal inflammation can be determined after 7 days, after 14 days, after 21 days, after 30 days, or after 60 days. Reduction in symptoms associated with intestinal inflammation include reduced abdominal pain, reduced diarrhea, reduced weight loss, reduced lack of appetite, and reduced rectal bleeding. These symptoms can be measured by body weight, stool consistency, fecal blood, and colon length. Reduction in symptoms associated with intestinal inflammation can also be determined by reduced immune cell infiltration and damage to the colon as determined by pathology. As described herein, administration of beta-1,3-glucan derived from *Euglena* grown using fermentation results in reduced abdominal pain, reduced diarrhea, reduced weight loss, reduced lack of appetite, and/or reduced rectal bleeding after 30 days of an effective dose. In some embodiments, administration of beta-1,3-glucan derived from *Euglena* grown using fermentation results in about 5% decrease or more in symptoms associated with intestinal inflammation after 30 days of an effective dose, about 10% decrease or more in symptoms associated with intestinal inflammation after 30 days of an effective dose, about 15% decrease or more in symptoms associated with intestinal inflammation after 30 days of an effective dose, about 20% decrease or more in symptoms associated with intestinal inflammation after 30 days of an effective dose, about 25% decrease or more in symptoms associated with intestinal inflammation after 30 days of an effective dose, about 30% decrease or more in symptoms associated with intestinal inflammation after 30 days of an effective dose, about 35% decrease or more in symptoms associated with intestinal inflammation after 30 days of an effective dose, about 40% decrease or more in symptoms associated with intestinal inflammation after 30 days of an effective dose, about 45% decrease or more in symptoms associated with intestinal inflammation after 30 days of an effective dose, about 50% decrease or more in symptoms associated with intestinal inflammation after 30 days of an effective dose, about 55% decrease or more in symptoms associated with intestinal inflammation after 30 days of an effective dose, about 60% decrease or more in symptoms associated with intestinal inflammation after 30 days of an effective dose, about 65% decrease or more in symptoms associated with intestinal inflammation after 30 days of an effective dose, about 70% decrease or more in symptoms associated with intestinal inflammation after 30 days of an effective dose, about 75% decrease or more in symptoms associated with intestinal inflammation after 30 days of an effective dose, about 80% decrease or more in symptoms associated with intestinal inflammation after 30 days of an effective dose, about 85% decrease or more in symptoms associated with intestinal inflammation after 30 days of an effective dose, about 90% decrease or more in symptoms associated with intestinal inflammation after 30 days of an effective dose, about 95% decrease or more in symptoms associated with intestinal inflammation after 30 days of an effective dose, or about 99% decrease or more in symptoms associated with intestinal inflammation after 30 days of an effective dose.

In addition, administration of effective amounts of an edible composition or a pharmaceutical formulation containing beta-1,3-glucan derived from *Euglena* grown using fermentation can increase anti-inflammatory cytokine production after the course of a dosing regimen. For example, IL-10 is implicated in limiting and terminating inflammatory responses (Asadullah, K. et al., *Pharm. Rev.* 2003, 55, 241-269). Additional anti-inflammatory cytokines include IL-1 receptor antagonist, IL-4, IL-6, IL-11, and IL-13. Specific cytokine receptors for IL-1, tumor necrosis factor-α, and IL-18 can function as proinflammatory cytokine inhibitors (Opal, S. M. et al. *CHEST* 2000, 117, 1162-1172).

The increase in anti-inflammatory cytokine production can be determined, for example, after 7 days, after 14 days, after 21 days, after 30 days, or after 60 days. An increase in anti-inflammatory cytokine production in an individual can be determined, for example, by analysis of a blood or tissue sample obtained from the individual. In some embodiments, administration of beta-1,3-glucan derived from *Euglena* grown using fermentation results in about 5% increase or more in anti-inflammatory cytokine production after 30 days of an effective dose, about 10% increase or more in anti-inflammatory cytokine production after 30 days of an effective dose, about 15% increase or more in anti-inflammatory cytokine production after 30 days of an effective dose, about 20% increase or more in anti-inflammatory cytokine production after 30 days of an effective dose, about 25% increase or more in anti-inflammatory cytokine production after 30 days of an effective dose, about 30% increase or more in anti-inflammatory cytokine production after 30 days of an effective dose, about 35% increase or more in anti-inflammatory cytokine production after 30 days of an effective dose, about 40% increase or more in anti-inflammatory cytokine production after 30 days of an effective dose, about 45% increase or more in anti-inflammatory cytokine production after 30 days of an effective dose, about 50% increase or more in anti-inflammatory cytokine production after 30 days of an effective dose, about 55% increase or more in anti-inflammatory cytokine production after 30 days of an effective dose, about 60% increase or more in anti-inflammatory cytokine production after 30 days of an effective dose, about 65% increase or more in anti-inflammatory cytokine production after 30 days of an effective dose, about 70% increase or more in anti-inflammatory cytokine production after 30 days of an effective dose, about 75% increase or more in anti-inflammatory cytokine production after 30 days of an effective dose, about 80% increase or more in anti-inflammatory cytokine production after 30 days of an effective dose, about 85% increase or more in anti-inflammatory cytokine production after 30 days of an effective dose, about 90% increase or more in anti-inflammatory cytokine production after 30 days of an effective dose, about 95% increase or more in anti-inflammatory cytokine production after 30 days of an effective dose, or about 100% increase or more in anti-inflammatory cytokine production after 30 days of an effective dose.

Each of the orally administered composition containing beta-1,3-glucan derived from *Euglena* grown using fermentation, the orally administered pharmaceutical formulation containing beta-1,3-glucan derived from *Euglena* grown using fermentation, and the intravenously administered pharmaceutical formulation containing beta-1,3-glucan derived from *Euglena* grown using fermentation are administered in an effective dose to treat intestinal inflammation. Such dosing regimens are generally understood as an amount of beta-1,3-glucan per kg body weight for each of the composition or pharmaceutical formulation. In some embodiments, the composition or pharmaceutical formulation is administered to the subject at an effective amount of about 0.1 mg beta-1,3-glucan per kg body weight or more, about 0.25 mg beta-1,3-glucan per kg body weight or more, about 0.5 mg beta-1,3-glucan per kg body weight or more, about 1 mg beta-1,3-glucan per kg body weight or more, about 2 mg beta-1,3-glucan per kg body weight or more, about 5 mg beta-1,3-glucan per kg body weight or more, about 10 mg beta-1,3-glucan per kg body weight or more, about 15 mg beta-1,3-glucan per kg body weight or more, about 25 mg beta-1,3-glucan per kg body weight or more, about 50 mg beta-1,3-glucan per kg body weight or more, about 75 mg beta-1,3-glucan per kg body weight or more, or about 100 mg beta-1,3-glucan per kg body weight or more. In some embodiments, the effective amount of the composition or pharmaceutical composition is between about 0.1 mg beta-1,3-glucan per kg body weight and about 100 mg beta-1,3-glucan per kg body weight, between about 0.1 mg beta-1,3-glucan per kg body weight and about 75 mg beta-1,3-glucan per kg body weight, between about 0.1 mg beta-1,3-glucan per kg body weight and about 50 mg beta-1,3-glucan per kg body weight, between about 0.1 mg beta-1,3-glucan per kg body weight and about 25 mg beta-1,3-glucan per kg body weight, between about 0.2 mg beta-1,3-glucan per kg body weight and about 15 mg beta-1,3-glucan per kg body weight, between about 0.5 mg beta-1,3-glucan per kg body weight and about 10 mg beta-1,3-glucan per kg body weight, between about 1 mg beta-1,3-glucan per kg body weight and about 10 mg beta-1,3-glucan per kg body weight, between about 50 mg beta-1,3-glucan per kg body weight and about 100 mg beta-1,3-glucan per kg body weight, between about 50 mg beta-1,3-glucan per kg body weight and about 75 mg beta-1,3-glucan per kg body weight, or between about 25 mg beta-1,3-glucan per kg body weight and about 75 mg beta-1,3-glucan per kg body weight. As described herein, an effective amount of the composition or pharmaceutical formulation can be administered to the subject once per day. In some embodiments, an effective amount of the composition or pharmaceutical formulation can be administered to a subject as multiple doses per day, for example twice per day or more frequently, three times per day or more frequently, or four times per day or more frequently. In some embodiments, an effective amount of the composition or pharmaceutical formulation can be administered to a subject once per week or more frequently, twice per week or more frequently, three times per week or more frequently, four times per week or more frequently, five times per week or more frequently, or six times per week or more frequently.

An effective amount of the composition or pharmaceutical formulation containing the beta-1,3-glucan derived from *Euglena* grown using fermentation can be administered to the subject to treat intestinal inflammation once per day. In some embodiments, an effective amount of an edible or pharmaceutical composition comprising beta-1,3-glucan derived from *Euglena* grown using fermentation is administered to a subject as multiple doses per day, for example twice per day or more frequently, three times per day or more frequently, or four times per day or more frequently. In some embodiments, an effective amount of an edible or pharmaceutical composition comprising beta-1,3-glucan derived from *Euglena* grown using fermentation is administered to a subject once per week or more frequently, twice per week or more frequently, three times per week or more frequently, four times per week or more frequently, five times per week or more frequently, or six times per week or more frequently.

Complexes with Trace Metals

In some embodiments, beta glucan can be complexed with a trace metal in order to create a complex that simultaneously be used to improve trace metal bioavailability while promoting general immune system activity. Trace metals include copper, zinc, iron, cobalt, magnesium, molybdenum, manganese, lithium, chromium, nickel, vanadium, selenium, and combinations thereof. The beta glucan and trace metal complex can be the result of complexing a soluble, inorganic trace metal salt with a beta glucan in solution.

Figure 5:
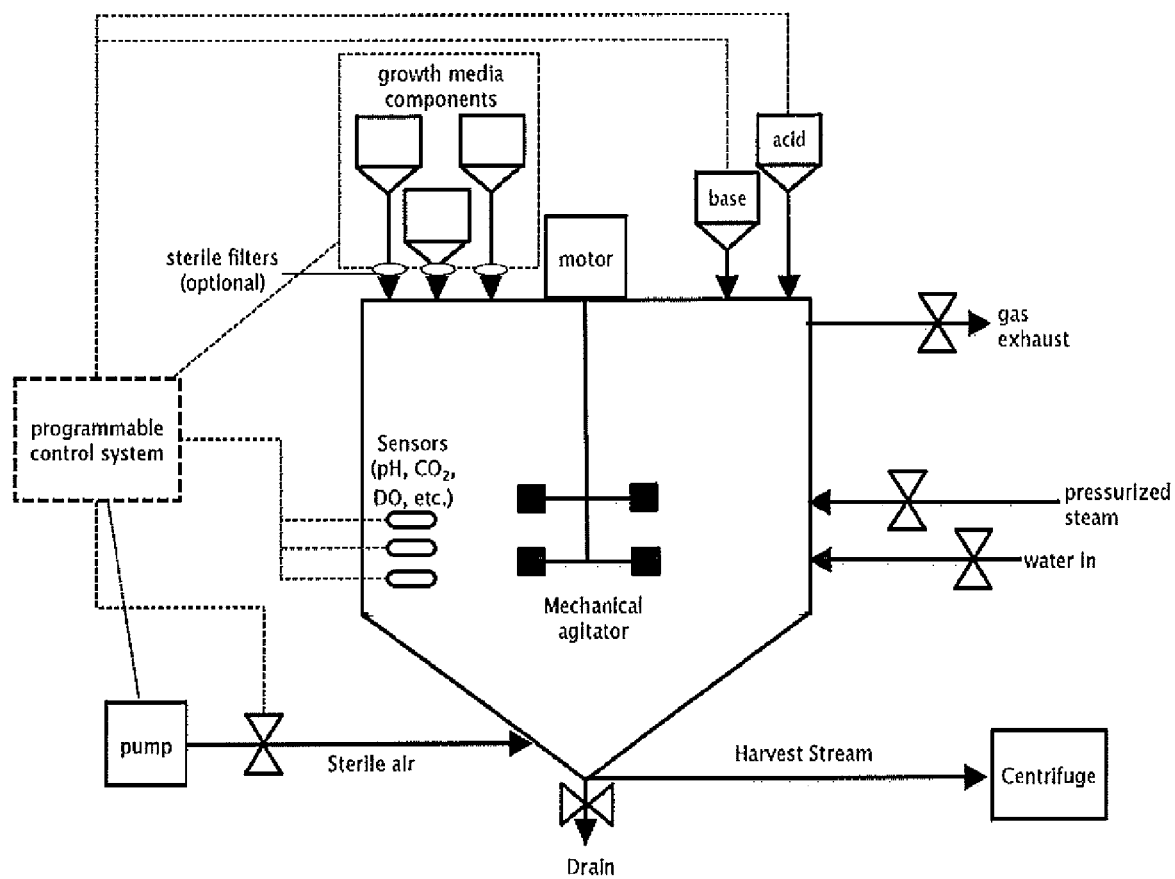
FIG. 5 shows a second embodiment of a system for growing *Euglena* according to the invention.
Figure 6:
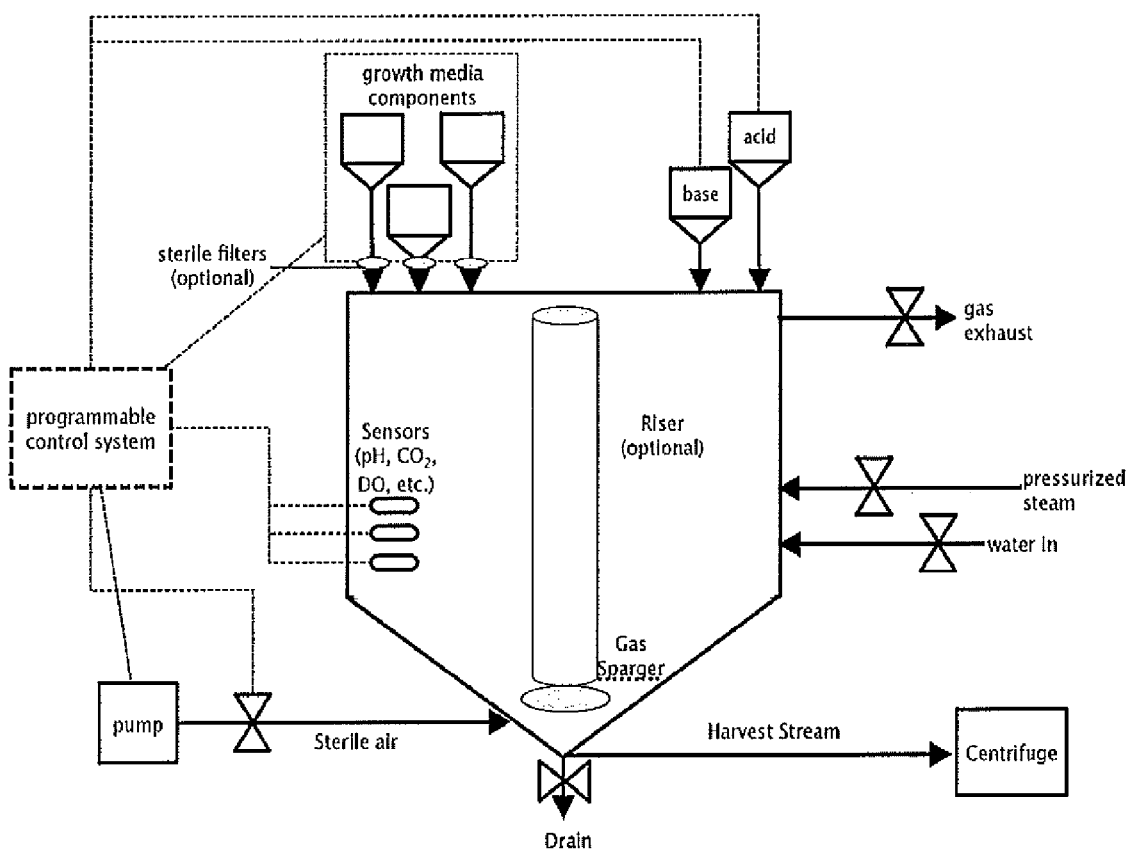
FIG. 6 shows a third embodiment of a system for growing *Euglena* according to the invention.

The beta glucan polysaccharide can comprise either a bioavailable form of beta glucan, such as paramylon granules that are present in a dry or wet whole cell algae suspension or beta glucan present in a dry or wet whole cell yeast, or an extracted source of beta glucan from algae, yeast, or another organism. The polysaccharide can be comprised of a suspension or paste of Euglena gracilis that has been grown heterotrophically in one or more sterile bioreactors. The Euglena can also be grown in an optimal manner such that the beta glucan portion of the algae product comprises greater than 20% of the algae biomass, as measured on a dry weight basis. Examples of processes for growing and creating such products are illustrated in FIGS. 5 and 6.

With reference to FIG. 25, an embodiment of a fermentation process is shown. Algae biomass is produced in a fermenter (1) under sterile conditions on chemically defined media. After the desired amount of time in the fermenter (1), the fermenter broth is transferred to a centrifuge (2) that dewaters the broth to produce two process streams: a wet algae meal that contains about 75% moisture; and used media. The wet algae meal contains a mixture of whole algae cells, algae cell fragments, and polysaccharides granules. The wet algae meal can be a polysaccharide solution containing over 50% by dry weight of beta glucan, a non-digestible polysaccharide. The wet algae meal is transferred to mixer (3), such as a mixing tank or any piece of equipment capable of mixing (e.g., ribbon blender). Optionally, the pH of the polysaccharide solution can be adjusted by the addition of acid or base (A).

A concentrated solution of a soluble metal salt (B), such as $ZnSO_4$—$H_2O$, can be added to the mixer (3) and mixed vigorously with the polysaccharide solution for 1-120 minutes. Any water soluble metal salt (B) may be used. For example, the metal salt (B) can be mixed with the beta glucan so that the final product can be a copper polysaccharide complex, zinc polysaccharide complex, iron polysaccharide complex, cobalt polysaccharide complex, magnesium polysaccharide complex, manganese polysaccharide complex, and combinations thereof. Preparation of the soluble metal salt (B) solution may involve heating a mixture of the metal salt (B) in water with mixing. Optionally, this mixer (3) may be heated or cooled. Optionally, the mixer (3) may be heated to the temperature required to pasteurize the material and inactivate enzyme activity. When the polysaccharide solution and metal salt (B) solution are mixing, some amount of complexation will occur between the metal ions and the polysaccharides present in the wet algae meal such that the final product may be considered a metal polysaccharide complex.

After the desired amount of mixing, the mixture is transferred to a dehydrator (4), which is any device capable of drying the material. For example, the dehydrator (4) may be a tray dryer, belt dryer, rotary drum dryer, etc. Once the material contains less than 10% moisture, it is transferred to a mill (5) where its particle size is reduced to less than 500 µm. More preferably, its particle size is reduced to less than 250 µm. Once the material has been milled, it is packaged (6) into containers of suitable size and labeled. Optionally, the addition of the metal salt (B) solution to the wet algae meal may be omitted and the resultant product will be algae meal.

With reference to FIG. 26, another embodiment of a fermentation process is shown. Algae biomass is produced in a fermenter (7) under sterile conditions on chemically defined media. Optionally, algal biomass may be produced in a growth tank under non-sterile conditions using any media that contains only feed-grade materials and is free of harmful substances (e.g., heavy metals, toxins, dangerous chemicals). After the desired amount of time in the fermenter or growth tank (7), the fermenter broth is transferred to a mixer (8), such as a mixing tank or any piece of equipment capable of providing mixing (e.g., ribbon blender). The fermenter broth contains a mixture of whole algae cells, algae cell fragments, and polysaccharides granules. In the case of a non-sterile growth tank, low levels of non-algal biomass may also be present.

Optionally, the pH of the fermenter broth is adjusted by addition of acid or base chemicals (C) to the mixer (8) to lyse cells, thereby releasing the majority of the polysaccharide granules from within the cells. This may be accomplished by adding base (e.g., NaOH) to the fermenter broth. Optionally, the broth may also be processed mechanically through a high-pressure homogenizer or ultrasonic cell disrupter to lyse cells. Optionally, the broth may be adjusted to an alkaline pH and then neutralized prior to centrifugation. After sufficient time that most if not all cells are lysed, the resultant mixture is transferred to a centrifuge (9) that dewaters the broth to produce two process streams: a crude polysaccharide solution (D); and mixture of other biomass materials (E).

The crude polysaccharide solution (D) is transferred to a mixer (10), such as a mixing tank or any piece of equipment capable of providing mixing (e.g., ribbon blender). The crude polysaccharide solution (D) may optionally be washed with water or a suitable alcohol (ethanol, isopropanol) to remove non-polysaccharide materials. Additional washes may be performed with any chemical suitable to remove non-polysaccharide materials. The pH of the crude polysaccharide solution (D) may optionally be adjusted with acid or base (F).

A concentrated solution of a soluble metal salt (G), such as $ZnSO_4$—$H_2O$, is prepared and added to the mixing tank (10) and mixed vigorously with the polysaccharide solution for 1-120 minutes. Any water-soluble metal salt may be used, such that the final product can be, for example, a copper polysaccharide complex, zinc polysaccharide complex, iron polysaccharide complex, cobalt polysaccharide complex, magnesium polysaccharide complex or manganese polysaccharide complex. Preparation of the soluble metal salt solution may involve heating a mixture of the metal salt in water with mixing. Optionally, mixer (10) may be heated or cooled. Optionally, the mixer (10) may be heated to the temperature required to pasteurize the material and inactivate enzyme activity. When the polysaccharide solution and metal salt solution are mixing, some amount of complexation will occur between the metal ions and the polysaccharides present such that the final product may be considered a metal polysaccharide complex.

After the desired amount of mixing, the mixture is transferred to a dehydrator (11), which is any device capable of drying the material. For example, the dehydrator (11) may be a tray dryer, belt dryer, rotary drum drier, etc. Once the material contains less than 10% moisture, it is transferred to a mill (12) where its particle size is reduced to less than 500 µm. More preferably, its particle size is reduced to less than 250 µm. One the material has been milled, it is packaged (13) into bags of suitable size and labeled.

The non-polysaccharide material (E) contains partially hydrolyzed proteins and amino acids and is transferred to a mixer (14), such as mixing tank or any piece of equipment capable of providing mixing (e.g., ribbon blender). The pH of the non-polysaccharide material (E) may optionally be adjusted with acid or base (H). A concentrated solution of a soluble metal salt (I), such as $ZnSO_4$—$H_2O$ is prepared and added to the mixer (14) and mixed vigorously with the amino acid-rich material for 1-120 minutes. Any water-soluble metal salt may be used, such that the final product can be, for example, a copper proteinate, zinc proteinate, iron proteinate, cobalt proteinate, magnesium proteinate, manganese proteinate, and combinations thereof. Preparation of the soluble metal salt solution may involve heating a mixture of the metal salt in water with mixing. Optionally, mixer (14) may be heated or cooled. Optionally, the mixer (14) may be heated to the temperature required to pasteurize the material and inactivate enzyme activity. When the non-polysaccharide solution and metal salt solution are mixing, some amount of complexation will occur between the metal ions and the partially hydrolyzed proteins and amino acids present such that the final product may be considered a metal proteinate.

After the desired amount of mixing, the mixture is transferred to a dehydrator (15), which is any device capable of drying the material. For example, the dehydrator (15) may be a tray dryer, belt dryer, rotary drum drier, multi-effect evaporator, etc. Once the material contains less than 10% moisture, it is transferred to a mill (16) where its particle size is reduced to less than 500 µm. More preferably, its particle size is reduced to less than 250 µm. Once the material has been milled, it is packaged (17) into bags of suitable size and labeled. Optionally, the addition of the metal salt solution to each process stream (D, E) may be omitted and the resultant products will be a relatively pure polysaccharide and partially hydrolyzed protein meal.

Advantages to complexing the trace metal and the beta glucan include an increase in the bioavailability of the trace metal in combination with the immune system modulating aspects of beta glucan. The beta glucan is indigestible in the gut and can shield the trace metal from binding to an agonist until it is released in the intestine, for example.

Furthermore, because some trace elements, such as zinc, are typically required in the diet in order to obtain optimal immune system functionality, the combination with an immune enhancing compound such as beta glucan can be more preferable in some situations for combining into an animal feed or vitamin premix blend than combining the same trace metal with another source, such as an amino acid or protein, which can also be provided as a separate product. The present processes demonstrate the capability of *Euglena*-derived beta glucan to bind or absorb large enough concentrations of zinc and other trace metals to deliver significant concentrations of the trace metal in an animal diet.

Some embodiments of a metal beta glucan complex include a member selected from the group consisting of a copper beta glucan complex, zinc beta glucan complex, iron beta glucan complex, cobalt beta glucan complex, magnesium beta glucan complex, molybdenum beta glucan complex, manganese beta glucan complex, and combinations thereof.

Although any trace-mineral containing inorganic salt may be used, some examples of salts include those that are commodities already used commercially as feed ingredients. Examples of such inorganic salts include but are not limited to metal sulfates, metal oxides, metal chlorides, hydrated metal salts, metal acetates, metal bromides, metal iodides, metal phosphates, metal selenites, and combinations thereof, where a portion of the salt can include iron, magnesium, lithium, zinc, copper, chromium, nickel, cobalt, vanadium, molybdenum, manganese, selenium, tungsten, iodine, and combinations thereof.

In some embodiments, the resulting metal polysaccharide complex includes 3% to 25% by weight metal and at least 25% by weight beta glucan. In certain cases, the polysaccharide portion of the product can be comprised of at least 50% by weight beta glucan. In certain cases, the polysaccharide portion of the product can be comprised of about 50% to 60% by weight beta glucan. Zinc sulfate or zinc oxide may be used as the trace mineral-containing salt to make a zinc beta glucan complex, where the zinc beta glucan complex can comprise at least 1% by weight zinc on a dry weight basis that can be administered at less than 3% by weight total inclusion in an animal's diet.

In certain cases, the polysaccharide portion of the product can be comprised between about 30 wt % to about 70 wt % beta-1,3-glucan, about 30 wt % to about 40 wt % beta-1,3-glucan, about 40 wt % to about 50 wt % beta-1,3-glucan, about 60 wt % to about 70 wt % beta-1,3-glucan, about 40 wt % to about 70 wt % beta-1,3-glucan, or about 50 wt % to about 70 wt % beta-1,3-glucan. In some embodiments, the polysaccharide portion of the product can be comprised between about 50 wt % to about 60 wt % beta-1,3-glucan, or about 50 wt % to about 55 wt % beta-1,3-glucan.

Method for Producing Compositions Comprising Beta-1,3-Glucan Derived from *Euglena*

*Euglena* is a genus of green algae that naturally grows and reproduces in a photosynthetic state, thus relying on sunlight to for survival. However, large-scale culture of *Euglena* grown using photosynthesis is difficult and not cost-effective. Moreover, *Euglena* grown using photosynthesis results in much lower amounts of beta glucan (i.e. less than 20% of the total *Euglena* cell mass). Accordingly, the *Euglena* useful for the methods and compositions described herein are grown by fermentation in large fermentation tanks. Generally, the fermenting *Euglena* cultures are heterotrophically grown, with little or no ambient light, relying on provided nutrients to synthesize the beta-1,3-glucan and other cellular components. *Euglena* grown using fermentation can grow to a greater cell density than naturally occurring or photosynthetic *Euglena* cultures, thereby producing higher amounts of beta-1,3-glucan. Fermented *Euglena* as described herein may be obtained using the methods described in US 2013/0303752.

Preferably, the *Euglena* useful for the methods disclosed herein is grown in a controlled environment such that the *Euglena* will remain the dominant microorganism in the environment. Controlled growth of any organism is difficult, as many contaminating organisms are capable of competing for the same biological resources (e.g., nutrients, micronutrients, minerals, and/or organic energy). Many of these microorganisms have faster growth rates and are capable of out-competing *Euglena* absent several controlled growth mechanisms that favor *Euglena*. These growth mechanisms can include one or more methods such as employment of growth media that favors *Euglena*, operation at a temperature that favors *Euglena*, pH levels that favor *Euglena*, addition of compounds that are toxic to competing organisms other than *Euglena*, and selective filtration or separation of *Euglena*. Each of these methods affects the growth rate and the ability of *Euglena* to convert energy into beta-1,3-glucan. In general, *Euglena* that are grown in an uncontrolled environment will not display the same beneficial properties of high beta-1,3-glucan concentration, fast growth rates, and efficient production of beta-1,3-glucans that *Euglena* produced in a more controlled growth environment will display.

In order to achieve cost-efficient large-scale *Euglena* cultures that efficiently produce beta-1,3-glucan, the organism is generally grown in large aerobic fermentation tanks. Growth media provides a carbon source, a nitrogen source, and other growth nutrients for *Euglena* growth and beta-1, 3-glucan production. The culture media, harvest schedule, and fermentation conditions are carefully controlled to ensure optimal beta-1,3-glucan production. In some embodiments, the production method yields large quantities of *Euglena* with about 30 wt % to about 70 wt % beta-1,3-glucan, about 30 wt % to about 40 wt % beta-1,3-glucan, about 40 wt % to about 50 wt % beta-1,3-glucan, about 50 wt % to about 60 wt % beta-1,3-glucan, about 60 wt % to about 70 wt % beta-1,3-glucan, about 40 wt % to about 70 wt % beta-1,3-glucan, or about 50 wt % to about 70 wt % beta-1,3-glucan.

Efficient production of beta-1,3-glucan derived from *Euglena* grown using fermentation reduces the cost of beta-1,3-glucan production in several ways. First, the beta-1,3-glucan produced by *Euglena* is not contained in the cell wall of the organisms and does not require elaborate and/or expensive fractionation methods or extraction processes, as is required by other organisms known to produce beta glucan. Second, the *Euglena* organisms are relatively large and may be separated from water relatively quickly by employing a centrifuge, filter, or other separation device. Third, individual *Euglena* cells are composed of a larger percentage of beta-1,3-glucan (as a percent of total cell mass) in comparison to other organisms, which results in easier recovery of the beta-1,3-glucan. In some embodiments, the *Euglena* growth is supplemented by light exposure.

Fermentation Growth of *Euglena*

The beta-1,3-glucan derived from *Euglena* useful for the compositions and methods described herein is produced by growing the *Euglena* using fermentation. Generally, growth media is provided to the *Euglena* such that the culture grows heterotrophically. However, it is contemplated that the *Euglena* can be grown in at least partial exposure to light. The large-scale production of beta-1,3-glucan is substantially more cost effective when the *Euglena* are heterotrophically fermented rather than grown using photosynthesis, due in part to the large-scale set-up of photosynthetic growth conditions for the algae and the increased cell density obtainable during growth using fermentation.

Exemplary methods of growing *Euglena* using fermentation are described herein and in U.S. Patent Publication 2013/0303752. These efficient and cost-effective methods allow for the cultivation of *Euglena* useful for the methods and compositions described herein, including the production of beta-1,3-glucan derived from *Euglena*, which may be administered as a *Euglena* biomass or further purified. The *Euglena* biomass can be used, for example, in an edible composition. Purified beta-1,3-glucan derived from *Euglena* can be administered either as an edible composition or as a pharmaceutical formulation, which may be orally or intravenously administered.

The *Euglena* grown using fermentation is cultivated using a growth medium. The growth medium provides nutrients to the growing *Euglena* culture, including a carbon source, a nitrogen source, and other micronutrients. The growth medium also includes a buffer to maintain the pH of the growth culture. To prevent the growth of unwanted organisms (such as bacteria), the growth medium is sterilized prior to being added to the fermentation tank. The growth medium can be sterilized, for example, by using a filter, steam, autoclaving, or a combination thereof. Optionally, different components of the medium are held in separate storage takes to prevent the formation of a complete growth medium during storage and contamination of the growth medium.

The fermenting *Euglena* relies on a carbon source present in the growth medium. Example carbon sources include glucose, dextrose, or other sugars; acetate; or ethanol. In some embodiments, the *Euglena* are grown in a growth medium with a carbon source at about 50 g/L or less, about 40 g/L or less, about 30 g/L or less, about 25 g/L or less, about 20 g/L or less, about 15 g/L or less, about 10 g/L or less, about 5 g/L or less, about 4 g/L or less, about 3 g/L or less, about 2 g/L or less, about 1 g/L or less, about 0.5 g/L or less, or about 0.1 g/L or less. Optionally, the growth medium is supplemented with additional carbon source during the course of growth. For example, the carbon source can be added two or more times to the growth medium, three or more times to the growth medium, or four or more times to the growth medium during the course of *Euglena* culture growth. The carbon source can be added semi-continuously. The carbon source can also be continuously added to the growth media.

The growth medium useful for growing *Euglena* by fermentation also includes a nitrogen source, such as ammonium hydroxide, ammonium gas, ammonium sulfate, or glutamate. In some embodiments, the growth medium includes about 0.1 g/L to about 3 g/L nitrogen source, about 0.2 g/L to about 2 g/L nitrogen source, or about 0.5 g/L to about 1 g/L nitrogen source. Preferably, the nitrogen source is ammonium hydroxide.

The growth medium further includes additional nutrients necessary for *Euglena* culture. For example, the growth medium can include potassium phosphate (such as about 0.25 g/L to about 5 g/L potassium phosphate, about 0.5 g/L to about 4 g/L potassium phosphate, or about 1 g/L to about 3 g/L potassium phosphate), magnesium sulfate (such as about 0.25 g/L to about 5 g/L magnesium sulfate, about 0.5 g/L to about 4 g/L magnesium sulfate, or about 1 g/L to about 3 g/L magnesium sulfate), calcium chloride (such as about 0.005 g/L to about 0.5 g/L calcium chloride, about 0.01 g/L to about 0.4 g/L calcium chloride, or 0.1 g/L to about 0.25 g/L calcium chloride), or a trace metal stock solution comprising micronutrients.

Maintaining the pH of the growth media allows for efficient beta-1,3-glucan production, *Euglena* cell growth, and helps limit the growth of unwanted bacteria. A pH of about 3 to about 4 is favorable to *Euglena*, but provides lower than the optimal growth conditions for most bacteria. In some embodiments, the pH of the growth medium is about 2 to about 7, about 2 to about 6, about 3 to about 5, about 3 to about 4, or about 3 to about 3.5. A buffer, for example citrate salt and/or citric acid, can be included in the growth media to maintain the pH of the growth medium in the desired range.

The desired pH of the growth medium may be achieved or maintained in several ways. The pH of the growth medium can be manually monitored and acid or base periodically added manually to reach the desired pH of the growth medium. The pH of the growth medium can alternatively or additionally be measured with a pH sensor connected to an automated control system, and the automated control system controls pumps, hoppers, or other devices that automatically adds acid or base to reach the desired pH of the growth medium that is programmed into the automated control system. In some embodiments, the metabolic processes of the *Euglena* sufficiently regulate the pH of the growth medium within the desired range.

To provide sufficient oxygen to the *Euglena* during fermentation, the growth medium can optionally be oxygenated, for example to about 0.5 mg/L to about 4 mg/L oxygen, about 1 mg/L to about 3 mg/L oxygen, or about 2 mg/L oxygen. The cell media can be oxygenated before being added to the fermentation tank or the fermenting *Euglena* culture can be mixed to facilitate dissolving ambient oxygen into the growth media.

Systems for fermenting *Euglena* can include one or more bioreactors. The *Euglena* culture is grown in the bioreactor to a specified cell density or a specified length of time before being the culture is either harvested or used to inoculate a larger bioreactor. Optionally, a portion of the *Euglena* culture can remain in the bioreactor to inoculate fresh growth media added to the bioreactor. The *Euglena* grown using fermentation can be grown in a multi-stage process, which may require two or more, three or more, or four or more bioreactors wherein the contents of an earlier bioreactor are transferred to and diluted in a later bioreactor. In another example of fermenting *Euglena*, the *Euglena* cell culture is grown using a fed-batch process, wherein fresh growth media or specific media components are continually added to the bioreactor as the *Euglena* culture grows. A repeated batch process can also be used to ferment the *Euglena*, wherein the *Euglena* culture is harvested at regular intervals or continuously harvested and replaced by fresh growth media.

In one example, the *Euglena* is grown in a single bioreactor, or a fermentation tank. Cell growth media is added to the bioreactor and inoculated with a *Euglena* culture. The *Euglena* culture can be, for example, a culture from a different bioreactor or a *Euglena* colony selected from a growth plate. In some embodiments, the single bioreactor is about 100 liters or larger, about 200 liters or larger, about 300 liters or larger, about 500 liters or larger, about 750 liters or larger, or about 1000 liters or larger. In some embodiments, the single bioreactor is about 100 liters or larger, about 200 liters or larger, about 300 liters or larger, about 500 liters or larger, about 750 liters or larger, about 1,000 liters or larger, about 5,000 liters or larger, about 10,000 liters or larger, about 15,000 liters or larger, or about 20,000 liters or larger. The *Euglena* ferment in the bioreactor before being harvested.

The *Euglena* culture can also grow in a multi-stage fermentation process, wherein multiple bioreactors are used in sequence. In a multi-stage fermentation process, each bioreactor has a larger bioreactor volume than the bioreactor in the preceding bioreactor. A *Euglena* culture grows in a first to reach a certain cell density. The culture is then used to inoculate the next sequential bioreactor.

Figure 2:
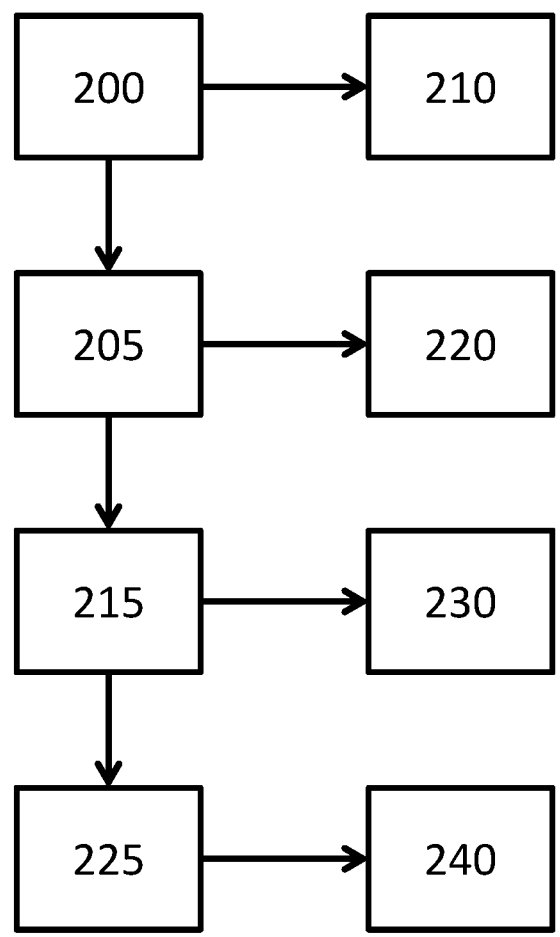
FIG. 2 shows a schematic representation for forming beta-1,3-glucan derived *Euglena* grown using fermentation according to one embodiment of the invention.
Figure 3:
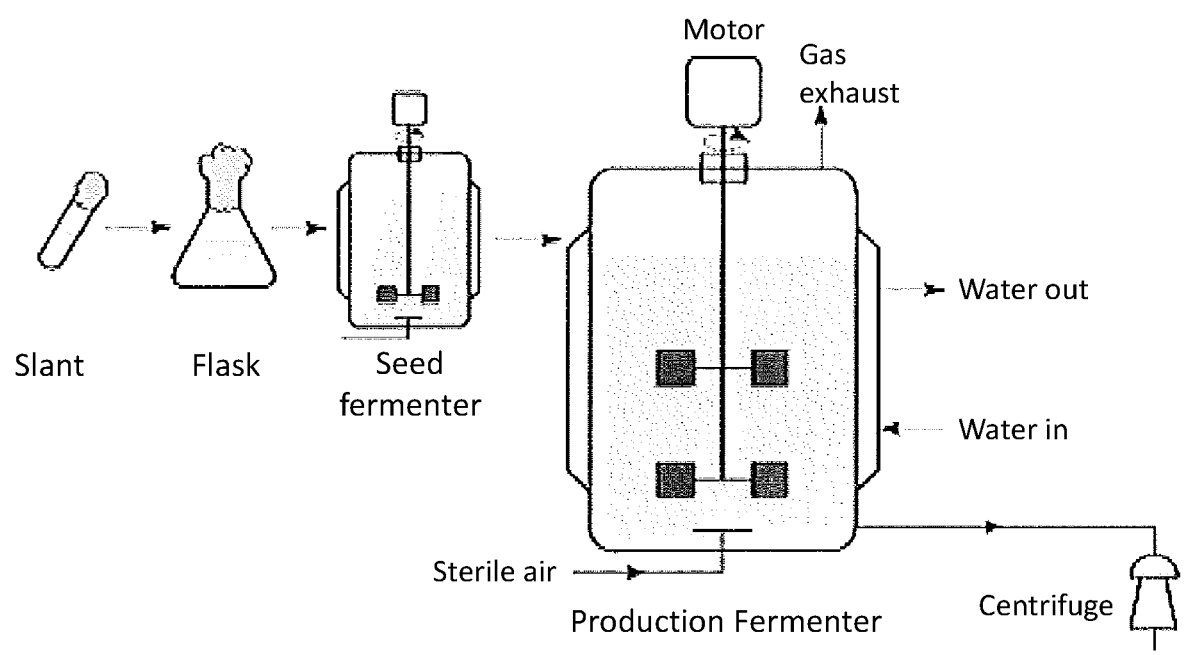
FIG. 3 shows a first embodiment of a system for growing *Euglena* according to the invention.

FIG. 2 illustrates an overview of an exemplary embodiment of forming beta-1,3-glucan derived *Euglena* grown using fermentation in a multi-stage process useful for the methods and compositions disclosed herein. FIG. 3 illustrates exemplary bioreactors that may be used to grow *Euglena* using fermentation in a multi-stage process. At 200, growth media is added to a first bioreactor stage and inoculated with *Euglena* cells. The first bioreactor stage can be, for example, any smaller container useful for a starter culture, for example an Erlenmeyer flask or a slant that is oxygenated through surface diffusion on a rotating or gyrating shaker table or magnetic stir bar. FIG. 3 illustrates one embodiment of a first bioreactor stage, labeled in the figure as "Slant." This first bioreactor can be heated using a heated table. The first bioreactor can also have a climate controlled atmosphere. A heated shaker table, such as a New Brunswick Scientific Innova 4000 Heated Desktop Incubator, is an example of a device that combines heating and the capability to oxygenate the flask by providing sufficient movement to agitate the surface of the growth media. After inoculation of the growth media, the *Euglena* culture grows in the first bioreactor until a predetermined time point or cell density is obtained. In some embodiments, the *Euglena* is grown in the first bioreactor for about 12 hours or more, about 24 hours or more, about 36 hours or more, about 48 hours or more, about 60 hours or more, about 72 hours or more, about 84 hours or more, about 96 hours or more, about 108 hours or more, or about 120 hours or more. In some embodiments, the *Euglena* grow in the bioreactor until reaching a cell density of about 20 grams dry weight per liter or more, about 30 grams dry weight per liter or more, about 40 grams dry weight per liter or more, about 50 grams dry weight per liter or more, about 75 grams dry weight per liter or more, about 100 grams dry weight per liter or more, about 125 grams dry weight per liter or more, about 150 grams dry weight per liter or more, about 175 grams dry weight per liter or more, or about 200 grams dry weight per liter or more. In some embodiments, the *Euglena* grow in the bioreactor until reaching a cell density of about 10 grams dry weight per liter to about 200 grams dry weight per liter, about 15 grams dry weight per liter to about 150 grams dry weight per liter, about 20 grams dry weight per liter to about 100 grams dry weight per liter, about 20 grams dry weight per liter to about 60 grams dry weight per liter, or about 40 grams dry weight per liter to about 60 grams dry weight per liter. If needed or desired, the first bioreactor is supplemented with fresh growth media while the *Euglena* is growing.

At step 205, the contents of the first bioreactor or a portion of the contents of the first bioreactor are transferred to a second bioreactor. Optionally, at step 210, the contents of the first bioreactor or a portion of the contents of the first bioreactor are harvested for further processing. A portion of the contents of the first bioreactor can be retained as an inoculant for a different culture. Optionally, the contents of the first bioreactor stage, at 200, are filtered or the *Euglena* is otherwise concentrated prior to transferring the *Euglena* to the second stage, at 210.

The *Euglena* culture from the first bioreactor is used to inoculate growth media in a second bioreactor to start further *Euglena* growth. Generally, the second bioreactor is larger than the first bioreactor. FIG. 3 illustrates one example of a second bioreactor stage, labeled in the figure as "Flask." The contents of the first bioreactor are diluted in the second bioreactor such that the concentration of *Euglena* in the second bioreactor after dilution is about 0.1 grams dry weight per liter to about 10 grams dry weight per liter. The second bioreactor can be up to about 10 times larger than the first bioreactor stage, up to about 20 times larger than the first bioreactor stage, up to about 30 times larger than the first bioreactor stage, up to about 50 times larger than first bioreactor stage, up to about 75 times larger than the first bioreactor stage, or up to about 100 times larger than the first bioreactor stage. In some embodiments, the *Euglena* grow by fermenting in the second bioreactor for about 12 hours or more, about 24 hours or more, about 36 hours or more, about 48 hours or more, about 60 hours or more, about 72 hours or more, about 84 hours or more, about 96 hours or more, about 108 hours or more, or about 120 hours or more. In some embodiments, the *Euglena* ferment in the bioreactor until reaching a cell density of about 20 grams dry weight per liter or more, about 30 grams dry weight per liter or more, about 40 grams dry weight per liter or more, about 50 grams dry weight per liter or more, about 75 grams dry weight per liter or more, about 100 grams dry weight per liter or more, about 125 grams dry weight per liter or more, about 150 grams dry weight per liter or more, about 175 grams dry weight per liter or more, or about 200 grams dry weight per liter or more. In some embodiments, the *Euglena* ferment in the bioreactor until reaching a cell density of about 10 grams dry weight per liter to about 200 grams dry weight per liter, about 15 grams dry weight per liter to about 150 grams dry weight per liter, about 20 grams dry weight per liter to about 100 grams dry weight per liter, about 20 grams dry weight per liter to about 60 grams dry weight per liter, or about 40 grams dry weight per liter to about 60 grams dry weight per liter. If necessary or desired, the second bioreactor is supplemented with fresh growth media while the *Euglena* is growing.

As further illustrated in FIG. 2, the contents or a portion of the contents of the second bioreactor are transferred to a third bioreactor at step 215. FIG. 3 illustrates one embodiment of a first bioreactor stage, labeled in the figure as "Seed fermenter." Optionally, the contents or a portion of the second bioreactor are harvested from the second bioreactor, at step 220. Generally, the third bioreactor is about 1 to about 100 times larger than the second bioreactor, and can be about 100 liters or more, about 250 liters or more, about 500 liters or more, about 1000 liters or more, about 2500 liters or more, about 5000 liters or more, about 7500 liters or more, about 10,000 liters or more, about 15,000 liters or more, about 25,000 liters or more, about 50,000 liters or more, or about 100,000 liters or more. In some embodiments, *Euglena* grows by fermenting in the third bioreactor for about 12 hours or more, about 24 hours or more, about 36 hours or more, about 48 hours or more, about 60 hours or more, about 72 hours or more, about 84 hours or more, about 96 hours or more, about 108 hours or more, or about 120 hours or more to reach a cell density of about 20 grams dry weight per liter or more, about 30 grams dry weight per liter or more, about 40 grams dry weight per liter or more, about 50 grams dry weight per liter or more, about 75 grams dry weight per liter or more, about 100 grams dry weight per liter or more, about 125 grams dry weight per liter or more, about 150 grams dry weight per liter or more, about 175 grams dry weight per liter or more, or about 200 grams dry weight per liter or more. In some embodiments, the *Euglena* ferment in the third bioreactor until reaching a cell density of about 10 grams dry weight per liter to about 200 grams dry weight per liter, about 15 grams dry weight per liter to about 150 grams dry weight per liter, about 20 grams dry weight per liter to about 100 grams dry weight per liter, about 20 grams dry weight per liter to about 60 grams dry weight per liter, or about 40 grams dry weight per liter to about 60 grams dry weight per liter. If necessary or desired, the third bioreactor is supplemented with fresh growth media while the *Euglena* is growing.

As further illustrated in FIG. 2, the contents or a portion of the contents of the third bioreactor are transferred to a fourth bioreactor at step 225. FIG. 3 illustrates one embodiment of a fourth bioreactor stage, labeled in the figure as "Production Fermenter." Optionally, the contents or a portion of the third bioreactor are harvested from the third bioreactor, at step 230. Generally, the fourth bioreactor has a volume ranging from about 1 to about 100 times greater than the third bioreactor stage, and has a volume of about 100 liters or more, about 250 liters or more, about 500 liters or more, about 1000 liters or more, about 2500 liters or more, about 5000 liters or more, about 7500 liters or more, about 10,000 liters or more, about 15,000 liters or more, about 25,000 liters or more, about 50,000 liters or more, about 100,000 liters or more, about 200,000 liters or more, about 400,000 liters or more, about 600,000 liters or more, about 800,000 liters or more, or about 1,000,000 liters or more. In some embodiments, the *Euglena* grow by fermenting in the fourth bioreactor for about 12 hours or more, about 24 hours or more, about 36 hours or more, about 48 hours or more, about 60 hours or more, about 72 hours or more, about 84 hours or more, about 96 hours or more, about 108 hours or more, or about 120 hours or more to reach a cell density of about 20 grams dry weight per liter or more, about 30 grams dry weight per liter or more, about 40 grams dry weight per liter or more, about 50 grams dry weight per liter or more, about 75 grams dry weight per liter or more, about 100 grams dry weight per liter or more, about 125 grams dry weight per liter or more, about 150 grams dry weight per liter or more, about 175 grams dry weight per liter or more, or about 200 grams dry weight per liter or more. In some embodiments, the *Euglena* ferment in the bioreactor until reaching a cell density of about 10 grams dry weight per liter to about 200 grams dry weight per liter, about 15 grams dry weight per liter to about 150 grams dry weight per liter, about 20 grams dry weight per liter to about 100 grams dry weight per liter, about 20 grams dry weight per liter to about 60 grams dry weight per liter, or about 40 grams dry weight per liter to about 60 grams dry weight per liter. The fourth bioreactor can be supplemented with fresh growth media while the *Euglena* is growing. FIG. 2 illustrates the contents of the fourth bioreactor being harvested at step 240, but it is further contemplated that subsequent bioreactors could be used. FIG. 3 illustrates one method of harvesting using a centrifuge.

Figure 4:
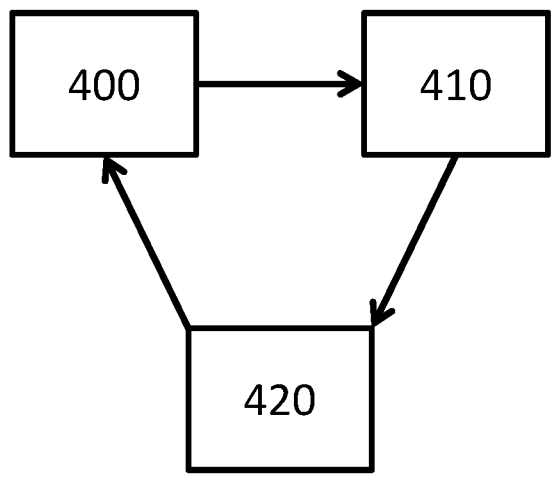
FIG. 4A shows a schematic representation of one embodiment of *Euglena* grown using fermentation by a repeated batch process.
FIG. 4B shows a graphical representation of *Euglena* concentration obtained from a repeat batch growth process according to one embodiment of the invention.
Figure 4:
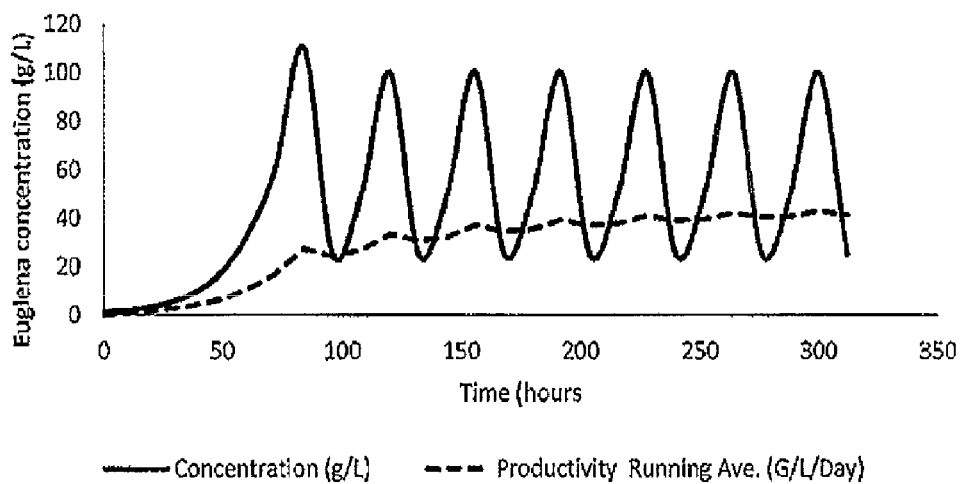

A repeated-batch process can also be used to grow *Euglena* using fermentation. In a repeated-batch process, a portion of the *Euglena* grown in a bioreactor is harvested and/or transferred to a different bioreactor and a portion of the *Euglena* remains in the bioreactor as an inoculant for later *Euglena* growth. The inoculant is then diluted by the addition of fresh growth medium to the bioreactor. FIG. 4A illustrates one exemplary embodiment of *Euglena* grown using fermentation by a repeated batch process. At step 400, growth media is added to a bioreactor and inoculated with *Euglena* cells. The *Euglena* is allowed to grow by fermentation in the bioreactor until the *Euglena* cell density reaches a predetermined cell density of about 20 grams dry weight per liter or more, about 30 grams dry weight per liter or more, about 40 grams dry weight per liter or more, about 50 grams dry weight per liter or more, about 75 grams dry weight per liter or more, about 100 grams dry weight per liter or more, about 125 grams dry weight per liter or more, about 150 grams dry weight per liter or more, about 175 grams dry weight per liter or more, or about 200 grams dry weight per liter or more. In some embodiments, the *Euglena* ferment in the bioreactor until reaching a cell density of about 10 grams dry weight per liter to about 200 grams dry weight per liter, about 15 grams dry weight per liter to about 150 grams dry weight per liter, about 20 grams dry weight per liter to about 100 grams dry weight per liter, about 20 grams dry weight per liter to about 60 grams dry weight per liter, or about 40 grams dry weight per liter to about 60 grams dry weight per liter. *Euglena* growth may continue for about 12 hours or more, about 24 hours or more, about 36 hours or more, about 48 hours or more, or about 60 hours or more to reach the desired cell density.

At step 410, a first portion of the contents of the bioreactor are harvested. A second portion of the contents of the bioreactor remain in the bioreactor to inoculate the next culture. Therefore, after the first portion of the contents of the bioreactor is harvested, fresh media is added to the bioreactor at 420 to dilute the cell density. The process can continue until either the desired amount of *Euglena* production is reached or until a contaminant organism eventually comprises a significant enough portion of the bioreactor to justify emptying the bioreactor and disinfecting it. An example of a repeat batch harvest of *Euglena* growth versus time is shown in FIG. 4B. As can be seen in FIG. 4B, once the *Euglena* ferments to a predetermined cell density, a portion of the contents are harvested and the remained is diluted with fresh media to inoculate a new culture.

A fed-batch process, such as a constantly-fed-batch process, can also be sued to grow *Euglena* using fermentation. In a fed-batch process, the *Euglena* culture is allowed to grow in an inoculated growth medium until it reaches a desired cell density. This initial growth period is generally termed a "batch phase." The batch phase may be about 12 hours or more, about 24 hours or more, about 36 hours or more, about 48 hours or more, or about 60 hours or more, during which time the *Euglena* culture reaches a cell density of about 20 grams dry weight per liter or more, about 30 grams dry weight per liter or more, about 40 grams dry weight per liter or more, about 50 grams dry weight per liter or more, about 75 grams dry weight per liter or more, about 100 grams dry weight per liter or more, about 125 grams dry weight per liter or more, about 150 grams dry weight per liter or more, about 175 grams dry weight per liter or more, or about 200 grams dry weight per liter or more. For example, the *Euglena* can grow in the bioreactor during the batch-phase until reaching a cell density of about 10 grams dry weight per liter to about 200 grams dry weight per liter, about 15 grams dry weight per liter to about 150 grams dry weight per liter, about 20 grams dry weight per liter to about 100 grams dry weight per liter, about 20 grams dry weight per liter to about 60 grams dry weight per liter, or about 40 grams dry weight per liter to about 60 grams dry weight per liter. After the batch phase is complete *Euglena* cells are continuously harvested and replaced by fresh growth media. This harvest and replace process is termed the continuous phase. During the continuous phase nutrient levels, pH, dissolved oxygen, or other parameters are monitored, for example using one or more sensors.

In one embodiment, the repeated-batch process is performed for up to 30 days. In another embodiment, the repeated-batch process is performed for up to 60 days. In still another embodiment, the repeated-batch process is performed for up to 90 days. In yet another embodiment, the repeated-batch process is performed for up to 120 days.

Any one of the bioreactors (whether the first bioreactor, second bioreactor, third bioreactor, fourth bioreactor, or subsequent bioreactor in a multi-stage process, a bioreactor in a repeated batch process, or a bioreactor fed-batch process) can be a metal or glass fermentation tank to contain the *Euglena* during growth. FIGS. 5 and 6 illustrate exemplary bioreactors that are useful in growing *Euglena* by fermentation.

Generally, the bioreactors are closed to the atmosphere during operation with the exception of one or more controlled vents, one or more inputs for aeration or oxygenation, or one or more inputs for supplying additional growth media. This allows better control over the fermentation conditions and limits contamination. Inputs for supplying the grown media can include a sterile filter, for example a filter with a pore size of less than 0.2 microns, in order to prevent undesirable non-*Euglena* microorganisms from entering the chamber. To further limit contamination, any one of the bioreactors can be cleaned or disinfected between batches. Cleaning or disinfecting the bioreactors can include steam, heat, or a disinfectant such as ethanol, bleach, or another chemical.

To help stimulate *Euglena* growth and beta-1,3-glucan production during fermentation, the growth media can be oxygenated or mixed. For example, additional oxygen can be provided to the *Euglena* culture by aerating the growth medium or receiving additional liquid whereby pressurized oxygen has been pre-dissolved into the liquid. The growth media can be aerated, for example, by supplying air enriched with oxygen into the growth medium during growth or by mixing the culture with one or more mixing mechanism to agitate the culture.

One or more of the bioreactors used to ferment *Euglena* can include an air-lift or bubble column system to mix the *Euglena* or aerate the growth medium. FIG. 6 shows an example of a bioreactor for growing *Euglena* using fermentation with an air lift. Air-lift reactors provide adequate mixing and aeration with less shear stress on cells during growth.

One or more bioreactors can include a mechanical stirring apparatus comprising a mixing blade for mixing or aerating the *Euglena* during growth. FIG. 5 illustrates an exemplary bioreactor that includes a mechanical stirring apparatus, for example a low-shear mixing blade such as a marine blade or a fixed-angle blade. The low-shear mixing blades limit damage to the growing *Euglena* cells.

The *Euglena* are harvested or transferred after growing in the final bioreactor, whether this is the first bioreactor, second bioreactor, third bioreactor, fourth bioreactor or subsequent bioreactor. In some embodiments, the *Euglena* ferment in a bioreactor for about 12 hours or more about 24 hours or more, about 36 hours or more, about 48 hours or more, about 60 hours or more, about 72 hours or more, about 84 hours or more, about 96 hours or more, about 108 hours or more, or about 120 hours or more before being harvested or transferred to a new bioreactor. For example, the *Euglena* can be cultivated about 12 to about 120 hours before being harvested or transferred to a new bioreactor, for example after about 24 hours to about 96 hours, about 36 hours to about 72 hours, or about 48 hours to about 60 hours before being harvested or transferred to a new bioreactor. In harvesting the *Euglena* cell culture, either the entire contents of the final bioreactor can harvested or a portion of the cell culture can be reserved. The reserved cell culture can be used as an inoculant in a different bioreactor or the same bioreactor.

In some embodiments, the methods of growing *Euglena* using fermentation produce *Euglena* at a cell density of about 20 grams dry weight per liter or more, about 30 grams dry weight per liter or more, about 40 grams dry weight per liter or more, about 50 grams dry weight per liter or more, about 75 grams dry weight per liter or more, about 100 grams dry weight per liter or more, about 125 grams dry weight per liter or more, about 150 grams dry weight per liter or more, about 175 grams dry weight per liter or more, or about 200 grams dry weight per liter or more. In other embodiments, the method of growing *Euglena* produces *Euglena* at a cell density of about 10 grams dry weight per liter to about 200 grams dry weight per liter, about 15 grams dry weight per liter to about 150 grams dry weight per liter, about 20 grams dry weight per liter to about 100 grams dry weight per liter, about 20 grams dry weight per liter to about 60 grams dry weight per liter, or about 40 grams dry weight per liter to about 60 grams dry weight per liter. In still other embodiments, the *Euglena* have about 30 wt % to about 70 wt % beta-1,3-glucan, such as about 30 wt % to about 40 wt % beta-1,3-glucan, about 40 wt % to about 50 wt % beta-1,3-glucan, about 50 wt % to about 60 wt % beta-1,3-glucan, or about 60 wt % to about 70 wt % beta-1,3-glucan, about 40 wt % to about 70 wt % beta-1,3-glucan, or about 50 wt % to about 70 wt % beta-1,3-glucan.

After the *Euglena* is harvested from the bioreactor, the *Euglena* biomass is separated from the growth media, for example by centrifuge, tangential flow filtration, filter press, belt press, or other solid-liquid separation device. Generally, the *Euglena* biomass is separated from the growth medium until the compositions reaches about 20 wt % solids or more, about 25 wt % solids or more, about 30 wt % solids or more, about 35 wt % solids or more, or about 40 wt % solids or more.

The harvested *Euglena* biomass can then be dried before it is further processed. The *Euglena* biomass can be dried using a belt drier, spray drier, drum dryer, furnace, or by spreading the biomass over a large surface area and using evaporative drying. Heat or vacuum can be applied aid the drying process. The *Euglena* biomass can also be freeze-dried to produce the dried biomass. The *Euglena* biomass can be dried until it reaches a moisture content of about 40% or less, about 30% or less, about 25% or less, about 20% or less, about 15% or less, about 10% or less, about 5% or less, about 4% or less, about 3% or less, about 2% or less, or about 1% or less.

The dried *Euglena* biomass can be administered as an edible composition to reduce blood serum cholesterol levels or blood serum triglyceride levels, or it can be administered to modulate an immune function in a subject. The *Euglena* biomass can also be further processed to purify beta-1,3-glucan from the *Euglena* biomass for use in an edible composition of pharmaceutical formulation administered to reduce blood serum cholesterol levels or blood serum triglyceride levels, or to modulate an immune function in a subject.

The dried *Euglena* biomass can be administered as an edible composition to treat intestinal inflammation in a subject. The *Euglena* biomass can also be further processed to purify beta-1,3-glucan from the *Euglena* biomass for use in an edible composition of pharmaceutical formulation administered to treat intestinal inflammation in a subject.

Purification of Beta-1,3-Glucan Derived from *Euglena* Grown Using Fermentation

The beta glucan can be extracted from the *Euglena* through a liquid/solid separation, a physical separation method, or another method. A substantial portion of the beta-1,3-glucan produced by *Euglena* is in the form of paramylon. The paramylon is generally present in *Euglena* in the form of water-insoluble granules of about 0.5 to about 2 microns in size and located within the *Euglena* cells. Therefore, the beta-1,3-glucan is generally purified by lysing the *Euglena* cells and isolating the beta-1,3-glucan from the residual biomass. Optionally, the beta-1,3-glucan is purified using methanol. Preferably, the beta-1,3-glucan is purified without the use of chloroform.

The beta-1,3-glucan derived from *Euglena* is extracted by lysing the cells and isolating the beta-1,3-glucan. The *Euglena* cells can be lysed using sonication or high pressure homogenization. Optionally, lysing chemicals are included during the lysis step. However, it is possible to lyse the *Euglena* cells without the addition of lysing chemicals. Exemplary lysing chemicals that could be included during the lysis step include detergents (such as sodium dodecyl sulfate), enzymes, bases (such as sodium hydroxide), or acids (such as acetic acid or hydrochloric acid). After lysing the *Euglena* cells, the beta-1,3-glucan is isolated using filtration or gravity separation (such as gravity settling or centrifugation). The isolated beta-1,3-glucan can then be washed, for example with an aqueous solution or an ethanol, to obtain higher purity.

After purification of the beta-1,3-glucan derived from *Euglena*, additional processing steps can modify the purified beta-1,3-glucan. Modified beta-1,3-glucan displays increased binding affinity to immune system receptors, such as Dectin-1, a protein that has been identified as a beta glucan receptor. For example, sulfated polysaccharides have been demonstrated to display anti-HIV activity (e.g., U.S. Pat. No. 5,861,383). In one exemplary method of preparing a sulfated beta-1,3-glucan, the purified beta-1,3-glucan is dissolved in dimethyl sulfoxide and combined with a mixture of dry pyridine and chlorosulfonic acid. The mixture is then heated and the supernatant is decanted. Subsequently, distilled water or methanol is added to the supernatant in order to precipitate pyridinium beta-1,3-glucan sulfate, which can then be collected by filtration. Alternatively, sodium chloride is added to the supernatant and the pH is raised to 9, allowing the sodium beta-1,3-glucan sulfate to precipitate in an acetone solution (see Sakagami et al., In vivo 3:243-248 (1989)).

Beta-1,3-glucan derived from *Euglena* can also be modified to be cationic. Cationic beta glucan can be more biologically active as an immunomodulator, as it has increased binding affinity with beta glucan receptors such as Dectin-1 and complement receptor 3 (see Sakagami et al., *Antiviral Research*, 21:1-14 (1993)). Beta-1,3-glucan derived from *Euglena* grown by fermentation can be modified with dimethylethanolamine (DMAE) to produce the cationic beta-1,3-glucan. One exemplary method of producing DMAE beta-1,3-glucan comprises dissolving the beta-1,3-glucan derived from *Euglena* in a base solution (such as a solution comprising NaOH), and adding a DMAE-chloride (either as a solution or dried powder). The resulting reaction produces DMAE beta-1,3-glucan.

EXEMPLARY EMBODIMENTS

Embodiment I-1

The disclosure provides a method of modulating the immune function in a human in need thereof comprising orally administering to the human an effective amount of a composition comprising beta-1,3-glucan derived from *Euglena* grown using fermentation.

Embodiment I-2

The disclosure provides the method of Embodiment I-1, wherein the effective amount of the composition is between 0.1 mg beta-1,3-glucan/kg body weight and 50 mg beta-1,3-glucan/kg body weight.

Embodiment I-3

The disclosure provides the method of Embodiment I-1, wherein administration of the composition modulates an autoimmune response, blood sugar level, an infection, or inflammation.

Embodiment I-4

The disclosure provides the method of Embodiment I-3, wherein the inflammation is associated with allergies.

Embodiment I-5

The disclosure provides the method of Embodiment I-3, wherein the autoimmune response is associated with diabetes.

Embodiment I-6

The disclosure provides the method of Embodiment I-3, wherein the infection is a bacterial, fungal, or viral infection.

Embodiment I-7

The disclosure provides the method of Embodiment I-1, wherein the *Euglena* is heterotrophically grown.

Embodiment I-8

The disclosure provides the method of Embodiment I-1, wherein the beta-1,3-glucan comprises paramylon.

Embodiment I-9

The disclosure provides the method of Embodiment I-1, wherein the beta-1,3-glucan does not contain beta-1,6-glycosidic bonds.

Embodiment I-10

The disclosure provides the method of Embodiment I-1, wherein the beta-1,3-glucan is purified from *Euglena*.

Embodiment I-11

The disclosure provides the method of Embodiment I-1, wherein the composition comprises *Euglena* biomass, the *Euglena* biomass comprising the beta-1,3-glucan.

Embodiment I-12

The disclosure provides the method of Embodiment I-11, wherein the *Euglena* biomass is dried.

Embodiment I-13

The disclosure provides the method of Embodiment I-12, wherein the *Euglena* biomass has been further processed to have an average particle size of 1000 microns or less.

Embodiment I-14

The disclosure provides the method of Embodiment I-1, wherein the composition is administered daily as a single dose.

Embodiment I-15

The disclosure provides the method of Embodiment I-1, wherein the composition is administered as multiple separate doses in a single day.

Embodiment I-16

The disclosure provides the method of Embodiment I-1, wherein the composition further comprises an additional component selected from the group consisting of alpha tocopherol, cholecalciferol, zinc, chromium, selenium, arginine, ascorbic acid, alkylglycerol, caffeine, kava kava, *Curcuma longa, Spirulina, Chlorella, stevia*, calcium D-glucarate, coenzyme Q10, peptides, dimethylglycine, docosahexaenoic acid, eicosapentaenoic acid, alpha-linolenic acid, astaxanthin, beta carotene, lutein, *lactobacillus* probiotics, *bifidobacterium* probiotics, mannoligosaccharide, fructooligosaccharides, *Astragalus, Echinacea*, Esberitox, garlic, glutathione, kelp, L-arginine, L-ornithine, lecithin granules, extracts from maiitake, reishi or shiitake mushrooms, manganese, quercetin, bromelain, Olive Leaf, *Sambucus*, Umcka, panthothenic acid, quercetin, alpha lipoic acid, essential oils, fish oils, spices and their derivatives, pterostilbene, and combinations thereof.

Embodiment I-17

The disclosure provides the method of Embodiment I-1, wherein the composition is administered as a solid.

Embodiment I-18

The disclosure provides the method of Embodiment I-1, wherein the composition is administered as a suspension.

Embodiment I-19

The disclosure provides a method of modulating the immune function in a human having high cholesterol or at risk of having high cholesterol comprising orally administering to the human an effective amount of a composition comprising beta-1,3-glucan derived from *Euglena* grown using fermentation.

Embodiment I-20

The disclosure provides the method of Embodiment I-19, wherein administration of the composition reduces the level of cholesterol in the human.

Embodiment I-21

The disclosure provides the method of Embodiment I-19, wherein the effective amount of the composition is between 0.1 mg beta-1,3-glucan/kg body weight and 50 mg beta-1,3-glucan/kg body weight.

Embodiment I-22

The disclosure provides the method of Embodiment I-19, wherein the *Euglena* is heterotrophically grown.

Embodiment I-23

The disclosure provides the method of Embodiment I-19, wherein the beta-1,3-glucan comprises paramylon.

Embodiment I-24

The disclosure provides the method of Embodiment I-19, wherein the beta-1,3-glucan does not contain beta-1,6-glycosidic bonds.

Embodiment I-25

The disclosure provides the method of Embodiment I-19, wherein the beta-1,3-glucan is purified from *Euglena*.

Embodiment I-26

The disclosure provides the method of Embodiment I-19, wherein the composition comprises *Euglena* biomass, the *Euglena* biomass comprising the beta-1,3-glucan.

Embodiment I-27

The disclosure provides the method of Embodiment I-26, wherein the *Euglena* biomass is dried.

Embodiment I-28

The disclosure provides the method of Embodiment I-27, wherein the *Euglena* biomass has been further processed to have an average particle size of 1000 microns or less.

Embodiment I-29

The disclosure provides the method of Embodiment I-19, wherein the composition is administered daily as a single dose.

Embodiment I-30

The disclosure provides the method of Embodiment I-19, wherein the composition is administered as multiple separate doses in a single day.

Embodiment I-31

The disclosure provides the method of Embodiment I-19, wherein the composition further comprises an additional component selected from the group consisting of alpha tocopherol, cholecalciferol, zinc, chromium, selenium, arginine, ascorbic acid, alkylglycerol, caffeine, kava kava, *Curcuma longa*, *Spirulina*, *Chlorella*, *stevia*, calcium D-glucarate, coenzyme Q10, peptides, dimethylglycine, docosahexaenoic acid, eicosapentaenoic acid, alpha-linolenic acid, astaxanthin, beta carotene, lutein, *lactobacillus* probiotics, *bifidobacterium* probiotics, mannoligosaccharide, fructooligosaccharides, *Astragalus*, *Echinacea*, Esberitox, garlic, glutathione, kelp, L-arginine, L-ornithine, lecithin granules, extracts from maiitake, reishi or shiitake mushrooms, manganese, quercetin, bromelain, Olive Leaf, *Sambucus*, Umcka, panthothenic acid, quercetin, alpha lipoic acid, essential oils, fish oils, spices and their derivatives, pterostilbene, and combinations thereof.

Embodiment I-32

The disclosure provides the method of Embodiment I-19, wherein the composition is administered in combination with statins, nicotinic acid, bile acid resins, fibric acid derivatives, or cholesterol absorption inhibitors.

Embodiment I-33

The disclosure provides the method of Embodiment I-19, wherein the composition is administered as a solid.

Embodiment I-34

The disclosure provides the method of Embodiment I-19, wherein the composition is administered as a suspension.

Embodiment II-1

The disclosure provides a method of enhancing the immune function in a human having intestinal inflammation comprising orally administering to the human an effective amount of a composition comprising beta-1,3-glucan derived from *Euglena* grown using fermentation.

Embodiment II-2

The disclosure provides the method of Embodiment II-1, wherein the effective amount of the composition is between 0.1 mg beta-1,3-glucan/kg body weight and 100 mg beta-1,3-glucan/kg body weight.

Embodiment II-3

The disclosure provides the method of Embodiment II-1, wherein the intestinal inflammation is inflammatory bowel disease.

Embodiment II-4

The disclosure provides the method of Embodiment II-1, wherein the intestinal inflammation is colitis.

Embodiment II-5

The disclosure provides the method of Embodiment II-1, wherein the intestinal inflammation is Crohn's disease.

Embodiment II-6

The disclosure provides the method of Embodiment II-1, wherein the *Euglena* is heterotrophically grown.

Embodiment II-7

The disclosure provides the method of Embodiment II-1, wherein the beta-1,3-glucan comprises paramylon.

Embodiment II-8

The disclosure provides the method of Embodiment II-1, wherein the beta-1,3-glucan does not contain beta-(1,6)-glycosidic bonds.

Embodiment II-9

The disclosure provides the method of Embodiment II-1, wherein the beta-1,3-glucan is purified from *Euglena*.

Embodiment II-10

The disclosure provides the method of Embodiment II-1, wherein the composition comprises *Euglena* biomass, the *Euglena* biomass comprising the beta-1,3-glucan.

Embodiment II-11

The disclosure provides the method of Embodiment II-10, wherein the *Euglena* biomass is dried.

Embodiment II-12

The disclosure provides the method of Embodiment II-11, wherein the *Euglena* biomass has been further processed to have an average particle size of 1000 microns or less.

Embodiment II-13

The disclosure provides the method of Embodiment II-1, wherein the composition is administered daily as a single dose.

Embodiment II-14

The disclosure provides the method of Embodiment II-1, wherein the composition is administered as multiple separate doses in a single day.

Embodiment II-15

The disclosure provides the method of Embodiment II-1, wherein the composition further comprises an additional component selected from the group consisting of alpha tocopherol, cholecalciferol, zinc, chromium, selenium, arginine, ascorbic acid, alkylglycerol, caffeine, kava kava, *Curcuma longa, Spirulina, Chlorella, stevia*, calcium D-glucarate, coenzyme Q10, peptides, dimethylglycine, docosahexaenoic acid, eicosapentaenoic acid, alpha-linolenic acid, astaxanthin, beta carotene, lutein, *lactobacillus* probiotics, *bifidobacterium* probiotics, mannoligosaccharide, fructooligosaccharides, *Astragalus, Echinacea*, Esberitox, garlic, glutathione, kelp, L-arginine, L-ornithine, lecithin granules, extracts from maiitake, reishi or shiitake mushrooms, manganese, quercetin, bromelain, Olive Leaf, *Sambucus*, Umcka, panthothenic acid, quercetin, alpha lipoic acid, essential oils, fish oils, spices and their derivatives, pterostilbene, and combinations thereof.

Embodiment II-16

The disclosure provides the method of Embodiment II-1, wherein the composition is administered as a solid.

Embodiment II-17

The disclosure provides the method of Embodiment II-1, wherein the composition is administered as a suspension.

Embodiment II-18

The disclosure provides the method of Embodiment II-1, wherein administering the composition increases anti-inflammatory cytokine production.

Embodiment II-19

The disclosure provides the method of Embodiment II-1, wherein the composition is administered in combination with anti-inflammatory drugs, immunosuppression drugs, or antibiotics.

Embodiment III-1

The disclosure provides a method of treating a condition selected from the group consisting of hyperlipidemia, metabolic syndrome, inflammatory bowel disease, colitis, Crohn's disease, and colon cancer in a human with said condition, the method comprising orally administering to the human an effective amount of a composition comprising beta-1,3-glucan from *Euglena* grown using fermentation.

Embodiment III-2

The disclosure provides a method of treating a condition selected from the group consisting of hyperlipidemia, metabolic syndrome, inflammatory bowel disease, colitis, and Crohn's disease in a human with said condition, the method comprising orally administering to the human an effective amount of a composition comprising beta-1,3-glucan from *Euglena* grown using fermentation.

Embodiment III-3

The disclosure provides the method of any one of Embodiments III-1-III-2, wherein the condition is hyperlipidemia.

Embodiment III-4

The disclosure provides the method of Embodiment III-3, wherein administration of the composition reduces the level of cholesterol in the human.

Embodiment III-5

The disclosure provides the method of any one of Embodiments III-3-III-4, wherein the effective amount of the composition comprises between 0.1 mg beta-1,3-glucan/kg body weight and 100 mg beta-1,3-glucan/kg body weight.

Embodiment III-6

The disclosure provides the method of any one of Embodiments III-3-III-4, wherein the effective amount of the composition comprises between 0.1 mg beta-1,3-glucan/kg body weight and 50 mg beta-1,3-glucan/kg body weight.

Embodiment III-7

The disclosure provides the method of any one of Embodiments III-3-III-6, wherein the composition is administered in combination with statins, nicotinic acid, bile acid resins, fibric acid derivatives, or cholesterol absorption inhibitors.

Embodiment III-8

The disclosure provides the method of Embodiment III-1, wherein the condition is selected from the group consisting of inflammatory bowel disease, colitis, Crohn's disease, and colon cancer.

Embodiment III-9

The disclosure provides the method of Embodiment III-1, wherein the condition is selected from the group consisting of inflammatory bowel disease, colitis, and Crohn's disease.

Embodiment III-10

The disclosure provides the method of any one of Embodiments III-8-III-9, wherein the condition is colitis.

Embodiment III-11

The disclosure provides the method of any one of Embodiments III-8-III-9, wherein the condition is inflammatory bowel disease.

Embodiment III-12

The disclosure provides the method of any one of Embodiments III-8-III-9, wherein the condition is Crohn's disease.

Embodiment III-13

The disclosure provides the method of Embodiment III-8, wherein the condition is colon cancer.

Embodiment III-14

The disclosure provides the method of any one of Embodiments III-8-III-13, wherein the effective amount of the composition comprises between 0.1 mg beta-1,3-glucan/kg body weight and 100 mg beta-1,3-glucan/kg body weight.

Embodiment III-15

The disclosure provides the method of any one of Embodiments III-8-III-14, wherein administering the composition increases anti-inflammatory cytokine production.

Embodiment III-16

The disclosure provides the method of any one of Embodiments III-8-III-15, wherein the composition is administered in combination with anti-inflammatory drugs, immunosuppression drugs, or antibiotics.

Embodiment III-17

The disclosure provides the method of any one of Embodiments III-1-III-16, wherein the *Euglena* is *Euglena gracilis*.

Embodiment III-18

The disclosure provides the method of any one of Embodiments III-1-III-17, wherein the *Euglena* is heterotrophically grown.

Embodiment III-19

The disclosure provides the method of any one of Embodiments III-1-III-18, wherein the beta-1,3-glucan is in the form of paramylon.

Embodiment III-20

The disclosure provides the method of any one of Embodiments III-1-III-19, wherein the beta-1,3-glucan does not contain beta-1,6-glycosidic bonds.

Embodiment III-21

The disclosure provides the method of any one of Embodiments III-1-III-20, wherein the beta-1,3-glucan is purified from *Euglena*.

Embodiment III-22

The disclosure provides the method of any one of Embodiments III-1-III-20, wherein the composition comprises *Euglena* biomass, the *Euglena* biomass comprising the beta-1,3-glucan.

Embodiment III-23

The disclosure provides the method of Embodiment III-22, wherein the *Euglena* biomass is dried to a moisture content of about 40% or less.

Embodiment III-24

The disclosure provides the method of Embodiment III-23, wherein the *Euglena* biomass has been further processed to have an average particle size of 1000 microns or less.

Embodiment III-25

The disclosure provides the method of any one of Embodiments III-1-III-24, wherein the composition is administered daily as a single dose.

Embodiment III-26

The disclosure provides the method of any one of Embodiments III-1-III-24, wherein the composition is administered as multiple separate doses in a single day.

Embodiment III-27

The disclosure provides the method of any one of Embodiments III-1-III-26, wherein the composition further comprises an additional component selected from the group consisting of alpha tocopherol, cholecalciferol, zinc, chromium, selenium, arginine, ascorbic acid, alkylglycerol, caffeine, kava kava, *Curcuma longa*, *Spirulina*, *Chlorella*, *stevia*, calcium D-glucarate, coenzyme Q10, peptides, dimethylglycine, docosahexaenoic acid, eicosapentaenoic acid, alpha-lineolenic acid, astaxanthin, beta carotene, lutein, *lactobacillus* probiotics, *bifidobacterium* probiotics, mannoligosaccharide, fructooligosaccharides, *Astragalus*, *Echinacea*, Esberitox, garlic, glutathione, kelp, L-arginine, L-ornithine, lecithin granules, extracts from maiitake, reishi or shiitake mushrooms, manganese, quercetin, bromelain, Olive Leaf, *Sambucus*, Umcka, panthothenic acid, quercetin, alpha lipoic acid, essential oils, fish oils, spices and their derivatives, pterostilbene, and combinations thereof.

Embodiment III-28

The disclosure provides the method of Embodiment III-27, wherein the additional component is zinc.

Embodiment III-29

The disclosure provides the method of any one of Embodiments III-1-III-27, wherein the composition further comprises a metal.

Embodiment III-30

The disclosure provides the method of Embodiment III-29, wherein the metal comprises a member selected from the group consisting of iron, magnesium, lithium, zinc, copper, chromium, nickel, cobalt, vanadium, molybdenum, manganese, selenium, and combinations thereof.

Embodiment III-31

The disclosure provides the method of Embodiment III-30, wherein the beta-(1,3)-glucan and the metal form a complex.

Embodiment III-32

The disclosure provides the method of Embodiment III-31, wherein the complex comprises a zinc beta-(1,3)-glucan complex.

Embodiment III-33

The disclosure provides the method of any one of Embodiments III-1-III-26, wherein the composition further comprises an additional component selected from the group consisting of *Haematococcus pluvialis*, astaxanthin, and colostrum.

Embodiment III-34

The disclosure provides the method of any one of Embodiments III-1-III-33, wherein the composition is administered as a solid.

Embodiment III-35

The disclosure provides the method of any one of Embodiments III-1-III-33, wherein the composition is administered as a suspension.

Embodiment III-36

The disclosure provides a composition comprising beta-1,3-glucan from *Euglena* grown using fermentation for use in the treatment of a condition selected from the group consisting of hyperlipidemia, metabolic syndrome, inflammatory bowel disease, colitis, Crohn's disease, and colon cancer.

Embodiment III-37

The disclosure provides a composition comprising beta-1,3-glucan from *Euglena* grown using fermentation for use in the treatment of a condition selected from the group consisting of hyperlipidemia, metabolic syndrome, inflammatory bowel disease, colitis, and Crohn's disease.

Embodiment III-38

The disclosure provides use of a composition comprising beta-1,3-glucan from *Euglena* grown using fermentation for the manufacture of a medicament for the treatment of a condition selected from the group consisting of hyperlipidemia, metabolic syndrome, inflammatory bowel disease, colitis, Crohn's disease, and colon cancer.

Embodiment III-39

The disclosure provides use of a composition comprising beta-1,3-glucan from *Euglena* grown using fermentation for the manufacture of a medicament for the treatment of a condition selected from the group consisting of hyperlipidemia, metabolic syndrome, inflammatory bowel disease, colitis, and Crohn's disease.

The following examples further illustrate embodiments of the present application. These examples are intended merely to be illustrative of embodiments of the present application and are not to be construed as being limiting.

EXAMPLES

Immune Response/Hyperlipidemia

Example 1: Oral Administration of *Euglena* Biomass Comprising Beta-1,3-Glucan

*Euglena* is grown using fermentation in a bioreactor using a repeated-batch process. In the final step, the *Euglena* is grown to a cell density of about 40 grams dry weight per liter to about 80 grams dry weight per liter and harvested. The *Euglena* cells have a beta-1,3-glucan content of about 70 wt %. The *Euglena* cell culture is filtered using tangential flow filtration, the spent growth media disposed, and the cells washed in water. The resulting *Euglena* biomass is rolled into thin sheets and dried to a moisture content of less than 10%. The *Euglena* biomass is then orally administered to a human to modulate an immune function.

Example 2: Oral Administration of *Euglena* Biomass Comprising Beta-1,3-Glucan as a Nutritional Supplement

*Euglena* is grown using fermentation in a bioreactor using a repeated-batch process. In the final step, the *Euglena* is grown to a cell density of about 40 grams dry weight per liter to about 80 grams dry weight per liter and harvested. The *Euglena* cells have a beta-1,3-glucan content of about 70 wt %. The *Euglena* cell culture is filtered using tangential flow filtration, the spent growth media disposed, and the cells washed in water. The *Euglena* biomass is then dried in a drum dryer to a moisture content of less than 5%. The dry flakes are processed into a powder using a hammer mill with an average grain size of less than 250 microns. The powder is then formed into tablets for oral administration to modulate an immune function, treat hyperlipidemia, or to prophylactically treat hyperlipidemia. Alternatively, the powder is mixed with a food product and orally administered with the food product to modulate an immune function. Alternatively, the powder is placed into a capsule for oral administration to modulate an immune function, treat hyperlipidemia, or to prophylactically treat hyperlipidemia.

Example 3: Purification of Beta-1,3-Glucan from *Euglena*

In one exemplary embodiment, beta-1,3-glucan is purified from *Euglena* by heating *Euglena* grown by fermentation as described herein in a 1% sodium dodecyl sulfate solution, centrifuging the solution, and washing the pellet with water and ethanol. Approximately one part *Euglena* biomass (dry weight basis) is suspended in 5 parts of 1% (w/v) sodium dodecyl sulfate solution. This suspension is mixed and then heated to about 100° C. for about 30 minutes. The solution is then cooled and centrifuged at >500 RCF for about 5 minutes. The supernatant is discarded and the pellet is washed by re-suspension in 10 parts water, mixed vigorously and centrifuged at >500 RCF for 5 minutes. The washing process can be repeated two more times with 10 parts 95% ethanol, to arrive at a 95% pure beta glucan pellet. The pellet can be further dried to a white powder.

In another exemplary embodiment, beta-1,3-glucan is purified from *Euglena* by pumping *Euglena* grown by fermentation as described herein through a high pressure homogenizer to lyse the cells. The lysed mixture is then centrifuged to recover the beta-1,3-glucan. The supernatant is discarded and the pellet is washed by re-suspension in water, mixed vigorously and centrifuged at >500 RCF. The washing process can be repeated two more times with 10 parts water, to arrive at a 95% pure beta-1,3-glucan pellet. The pellet can be further dried to a white powder.

The methods described herein are less toxic than some of the previous methods described for extracting beta-1,3-glucan, which may have added benefit of receiving safety and all-natural product certifications necessary for producing a food-grade or nutraceutical-grade product. The resulting purified beta-1,3-glucan is then formed into tablets for oral administration or mixed with a food product and orally administered. Alternatively, the purified beta-1,3-glucan can be mixed with an aqueous solution as a pharmaceutical composition. The pharmaceutical composition may further comprise a pharmaceutically acceptable excipient. The pharmaceutical composition can then be intravenously administered.

Example 4: Immune Response of Mice Administered Beta-1,3-Glucan Derived from *Euglena*

*Euglena* biomass comprising beta-1,3-glucan was grown using fermentation processes as described herein. The whole cell product and purified beta glucan extract were tested in a mouse study. The whole cell product was produced from *Euglena* cells grown on glucose as the organic carbon source. The whole cell product contained about 50 wt % beta-1,3-glucan and was centrifuged and then dried without any further processing. Fractionating the whole cell product to isolate the beta-1,3-glucan and then repeatedly washing the beta glucan fraction to remove non-beta glucan cell components produced the purified sample of beta-1,3-glucan. The purified sample comprised about 93 wt % beta-1,3-glucan. Also compared was commercially available yeast-derived beta glucan.

The whole cell *Euglena* biomass sample, purified beta-1,3-glucan sample, and yeast-derived beta glucan product were dried and ground to particle sizes of less than 500 microns. These dry powders were then mixed with PBS buffer and diluted to appropriate concentrations before being dosed by gavage to BALB/c mice. Blood was taken from each mouse to measure non-specific immune system activity. The following parameters were assessed: phagocytosis activity (the ability of macrophages to ingest foreign particles), natural killer (NK) cell activity (the ability of NK cells to destroy foreign or infected cells), and antibody titers.

Phagocytosis

Figure 7:
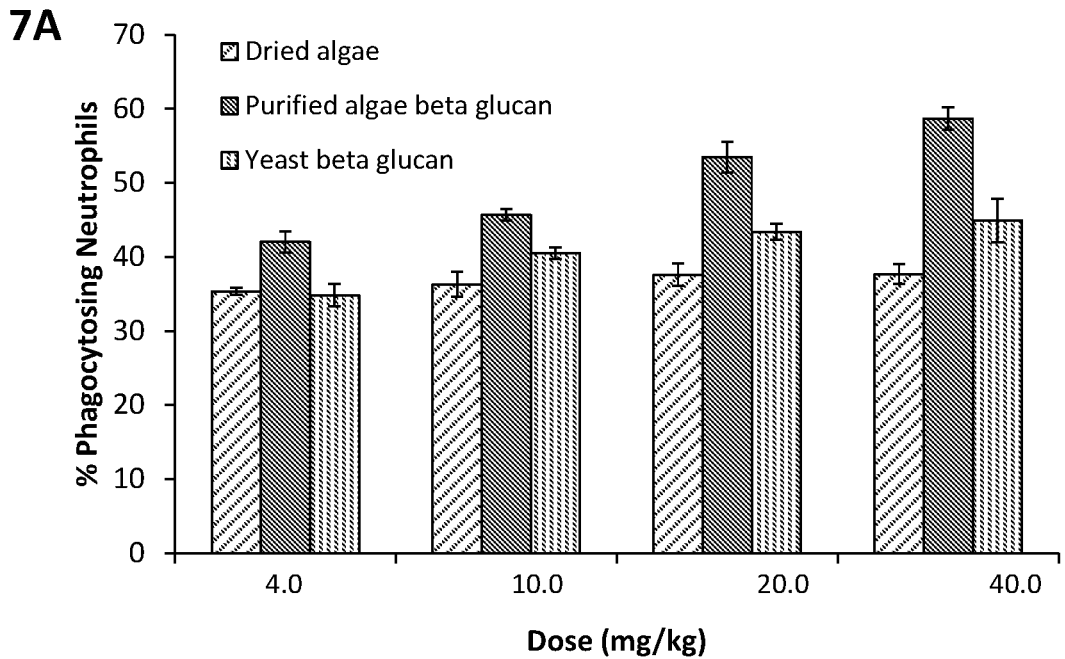
FIG. 7A graphically shows the phagocytosis index of mouse neutrophils sampled from peripheral blood on day 14 of the beta glucan treatment. The negative control received no beta glucan and had a response of 29.8±0.37%. Bars represent means±standard error (n=3 mice per treatment group).
FIG. 7B graphically shows natural killer (NK) cell activity of mouse spleen cells harvested on day 14 of the beta glucan treatment. The negative control received no beta glucan and had a response of 11.6±0.28%. Bars represent means±standard error (n=3 mice per treatment group).
FIG. 7C graphically shows antibody formation following ovalbumin injection of mice and daily dosing of beta glucan treatments for 23 days. The negative control received ovalbumin but no beta glucan and had a response of 49.1±4.6. Bars represent means±standard error (n=3 mice per treatment group).
Figure 7:
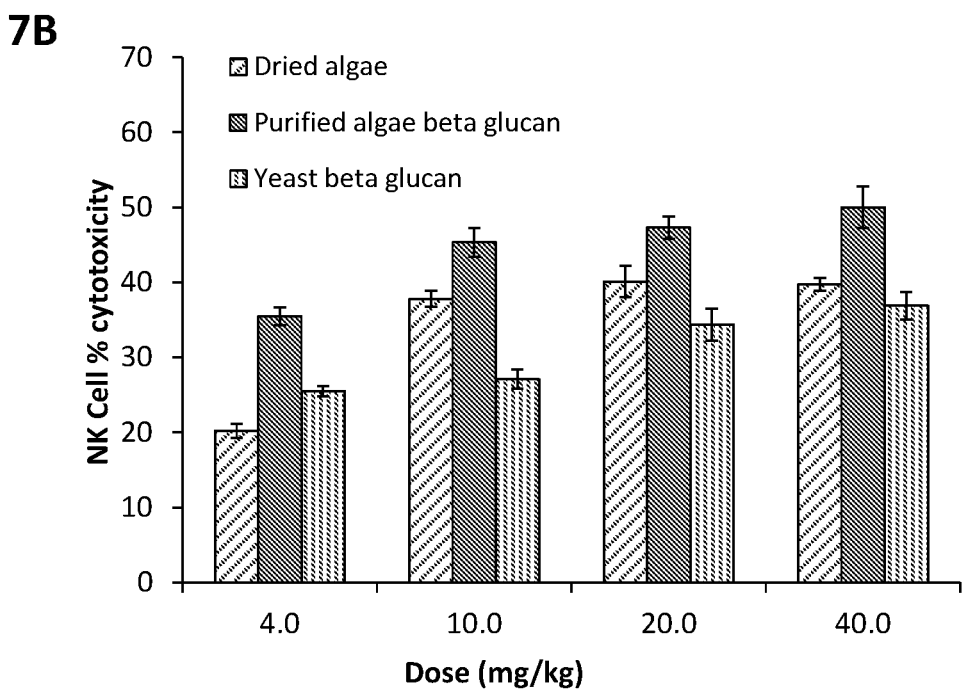
Figure 7:
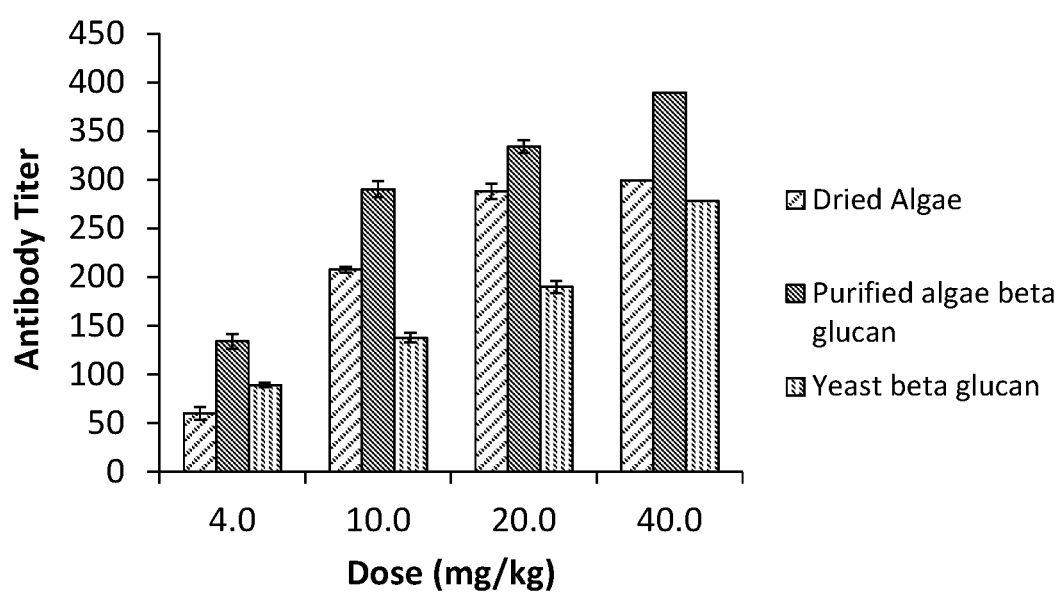

Phagocytosis is one response by the immune system to capture and destroy potentially harmful particles (e.g., bacteria). The phagocytosis index was measured as the percent of neutrophils that actively captured and engulfed labeled particles (FIG. 7A). Nine BALB/c mice were allocated to each treatment group and fed beta glucan products (20 mg/kg mice) by gavage daily. The control group received only a PBS gavage. On day 1, 7, and 14, three mice from each treatment group were sacrificed to harvest material for analyses. The phagocytosis index is measured as the percent of neutrophil cells that actively capture and engulf labeled particles in an allotted time. Mice that were given only the PBS control had a phagocytosis index of 30%, whereas mice fed the highest dose of purified beta glucan derived from *Euglena* demonstrated nearly twice the phagocytosis activity (59%). The group that received the purified algae beta glucan product demonstrated the best performance at each dosage level. The mice fed whole *Euglena* biomass and yeast-derived beta glucan demonstrated similar phagocytosis activity at the two lowest dosage levels, but mice fed yeast-derived beta glucan at the two highest dosage levels had slightly higher phagocytosis activity.

Natural Killer Cell Cytotoxicity

Natural killer (NK) cell activity (the ability of NK cells to destroy foreign or infected cells) was measured to determine the degree of immune function modulation due to the administered beta glucan (FIG. 7B). NK cell cytotoxicity is an index of the non-specific immune response by NK cells to kill potentially pathogenic organisms. Nine BALB/c mice were allocated to each treatment group and fed beta glucan products (20 mg/kg mice) by gavage daily. The control group received only a PBS gavage. On day 1, 7, and 14, three mice from each treatment group were sacrificed to harvest material for analyses. Mice that were fed the PBS control displayed a cytotoxicity index of 12%, whereas the mice fed with doses as low as 10 mg/kg of either whole *Euglena* biomass or purified *Euglena* beta glucan demonstrated a cytotoxicity index over three times higher (36 to 50%). At doses of 20 mg/kg and higher, both the whole *Euglena* biomass and purified *Euglena* beta glucan treatments elicited a stronger cytotoxicity response than the yeast-derived beta glucan product.

Antibody Titers

Antibody formation indicates that beta glucan can act as an adjuvant (modulator) for vaccines. Three BALB/c mice were allocated to each treatment group and received a daily oral dose of beta glucan products equivalent to 4, 10, 20, and 40 mg/kg starting on day 0. The antigen (ovalbumin) was given by intraperitoneal injection on days 3 and 16, and antibody titers were measured on day 23 using an ELISA assay with a PBS gavage as the negative control (FIG. 7C). Significant increases in antibody titers indicate the potential for products like beta glucan to serve as an adjuvant (enhancer) to vaccines. All of the beta glucan treatment groups elicited an increase in antibody production relative to the negative control, and this effect was enhanced at higher doses. The purified algae beta glucan treatment produced the most antibodies at each of the treatment levels, followed closely by the whole *Euglena* biomass treatment group. The mice fed the yeast beta glucan product demonstrated substantially lower (between 15 and 50% lower) antibody titers compared to those fed beta-1,3-glucan derived from *Euglena* at moderate dosing levels (10 and 20 mg/kg), but had similar titers to mice fed the whole *Euglena* biomass product at the highest dosage rate.

SUMMARY

Both specific immune responses (i.e. antibody production) and non-specific immune responses (NK cell cytotoxicity and phagocytosis activity) increased significantly for treatment groups fed any of the beta glucan products. For all of the immune metrics, purified algae beta-1,3-glucan elicited the strongest immune response at all treatment levels. Both whole *Euglena* biomass and purified algae beta-1,3-glucan elicited a very strong antibody response that was several fold higher than the titers found in the negative control. These data indicate the potential for these products to serve as adjuvants.

Whole *Euglena* biomass performed as well, if not better than, the yeast-derived beta glucan product at nearly all treatment levels in both antibody production and NK cell cytotoxicity assays. In most cases, whole *Euglena* biomass induced nearly the same or better response compared to the yeast-derived product at only a quarter to half the dosage level.

The yeast-derived beta glucan product elicited a lower phagocytosis response than purified algae beta glucan, but performed as well or better than the whole *Euglena* biomass product in this category. In general, the overall impact of all beta glucan products on phagocytosis is more tempered than NK cell cytotoxicity and antibody production.

Example 5: *E. coli* Challenge of Mice Administered Beta-1,3-Glucan Derived from *Euglena*

*Euglena* was grown in a sterile fermenter as described herein. Once the target density of *Euglena* biomass was reached in the fermenter, the cells were centrifuged and the resulting paste was stored frozen at −20° C. The frozen paste was thawed, dried at 65° C. until it formed dry flakes, and then ground to a particle size of less than 250 microns to produce a composition comprising *Euglena* biomass, the biomass comprising the beta-1,3-glucan derived from the *Euglena*. Purified beta-1,3-glucan derived from *Euglena* was produced by lysing the *Euglena* cells and isolating the beta-1,3-glucan through a process that results in an extract with >90% beta glucan and a particle size of less than 250 microns. To compare the samples of beta-1,3-glucan derived from *Euglena* with a sample of purified beta glucan derived from yeast, each dry product was mixed with phosphate buffered saline (PBS) and diluted to appropriate concentrations before being dosed by gavage to the mice at prescribed dosing levels.

Ten BALB/c mice were allocated to each treatment group and received a nominal lethal dose of *E. coli* ($3 \times 10^7$) via intramuscular injection on day 0. Beta glucan products (20 mg/kg mice) were orally dosed by gavage to the mice daily starting two days prior to the *E. coli* injection (day −2) through two days following the injection (day+2). The control group received only a PBS gavage, while an antibiotic-treated group received oral doses of Ampicillin (13 mg/kg) on days 0, 1, 2, 3, and 4. Mice were evaluated daily up through day 10.

Figure 8:
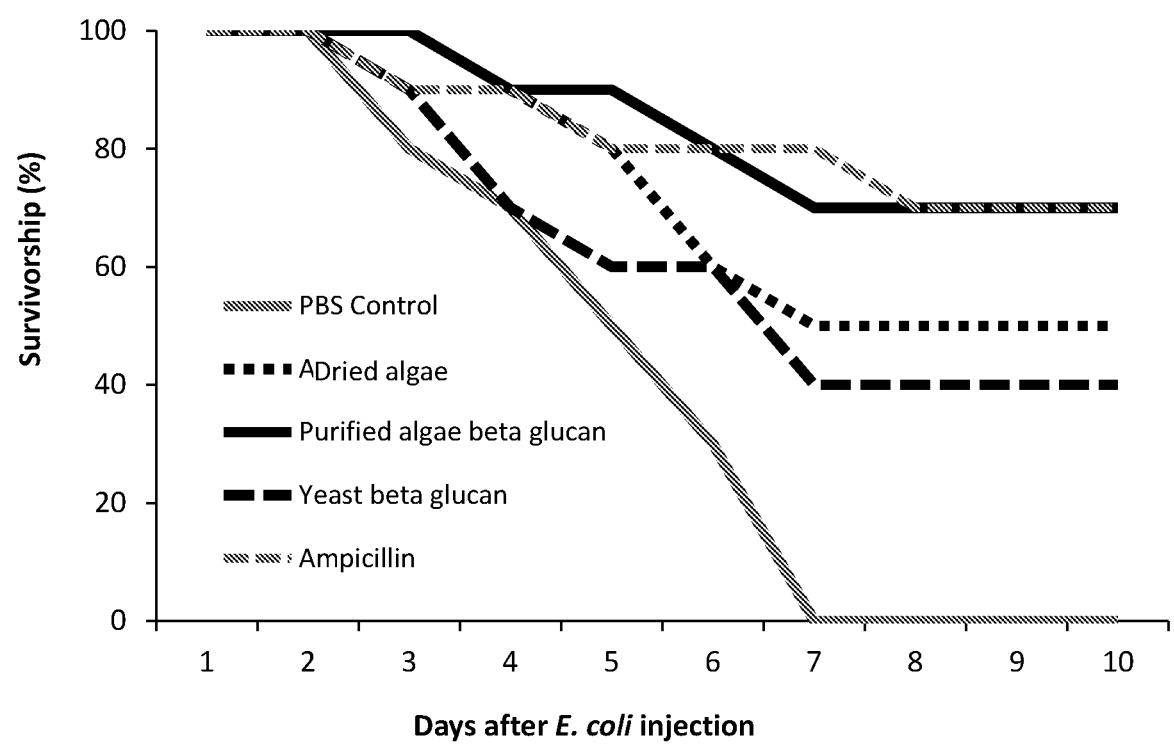
FIG. 8 graphically shows survivorship of mice following an injection of *E. coli* on day 0. Dried algae (i.e., *Euglena*), purified algae beta-1,3-glucan, and yeast-derived beta glucan were fed orally by gavage for 5 days at a dose equivalent to 0.01% of the daily feed ration starting 2 days before the *E. coli* injection (day −2). The PBS control group was given just a PBS gavage while the antibiotic treatment group was given 13 mg/kg of Ampicillin orally on days 0 through 4. Each treatment group consisted of n=10 mice. The light grey dashed line represents Ampicillin and the highest to lowest lines as viewed on the far right of the graph (i.e., days 7-10) represent purified algae beta-1,3-glucan, dried algae, yeast beta glucan, and PBS control, respectively.

FIG. 8 summarizes the results of the *E. coli* challenge experiments. All mice in the control group which received only PBS died within seven days of the *E. coli* injection. In contrast, mortality at day 10 was decreased in all treatment groups by at least 40%. Notably, 70% of the mice receiving purified beta-1,3-glucan derived from *Euglena* survived 10 days following *E. coli* injection. This treatment group and the one receiving Ampicillin showed very similar survival rates over time, suggesting that the algae beta-1,3-glucan treatment provided similar protection to the mice against bacterial infection as the common antibiotic Ampicillin. Mice receiving whole *Euglena* biomass product, which contained about 50% beta glucan, also showed a significant decline in mortality compared to the control group. In this treatment group, 50% of the mice survived 10 days following *E. coli* injection, compared to 40% surviving in the group fed the yeast-derived beta glucan extract.

Example 6: Cytokine Expression in Mice Administered Beta-1,3-Glucan Derived from *Euglena*

*Euglena* biomass comprising beta-1,3-glucan was grown using fermentation processes as described herein. The whole cell product was fractionated to isolate the beta glucan, and then the beta glucan fraction was repeatedly washed to remove non-beta-1,3-glucan cell components. The purified sample comprised about 93 wt % beta-1,3-glucan. The purified beta glucan product was used to evaluate the effect of beta-1,3-glucan on cytokine expression. Cytokines play an important role in the immune system and are involved in host responses to infection and inflammation.

Figure 9:
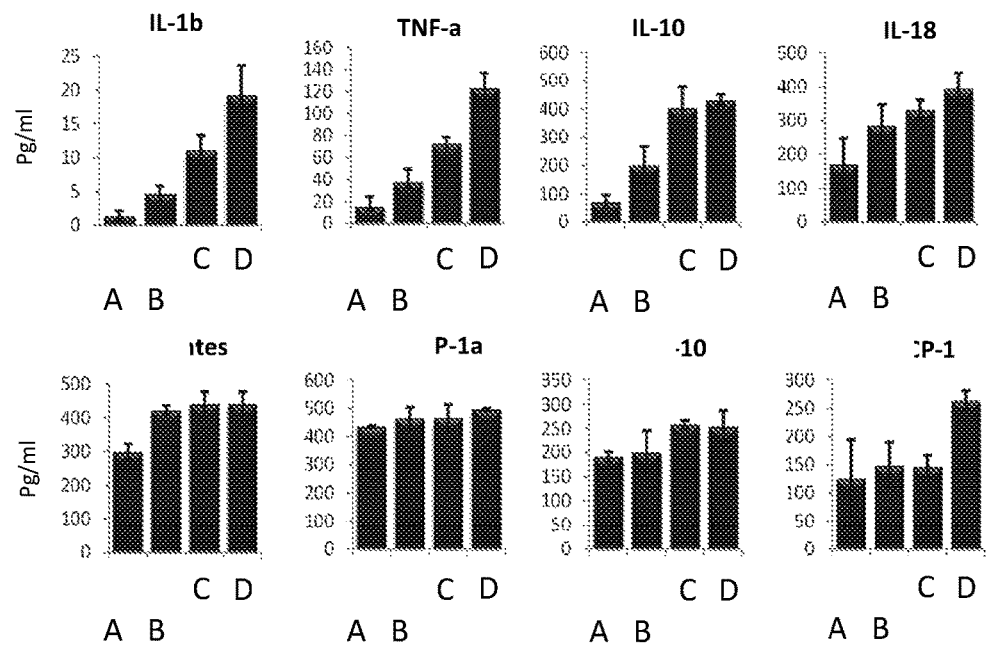
FIG. 9A graphically shows the effect of purified beta-1,3-glucan derived from *Euglena* on cytokine production by mouse dendritic cells following treatment with the beta glucan for 7 days.
FIG. 9B graphically shows the effect of purified beta-1,3-glucan derived from *Euglena* on cytokine production by mouse macrophages following treatment with the beta glucan for 7 days.
FIG. 9C graphically shows the effect of purified beta-1,3-glucan derived from *Euglena* on cytokine expression in mouse NK cells following treatment with the beta glucan for 7 days.
Figure 9:
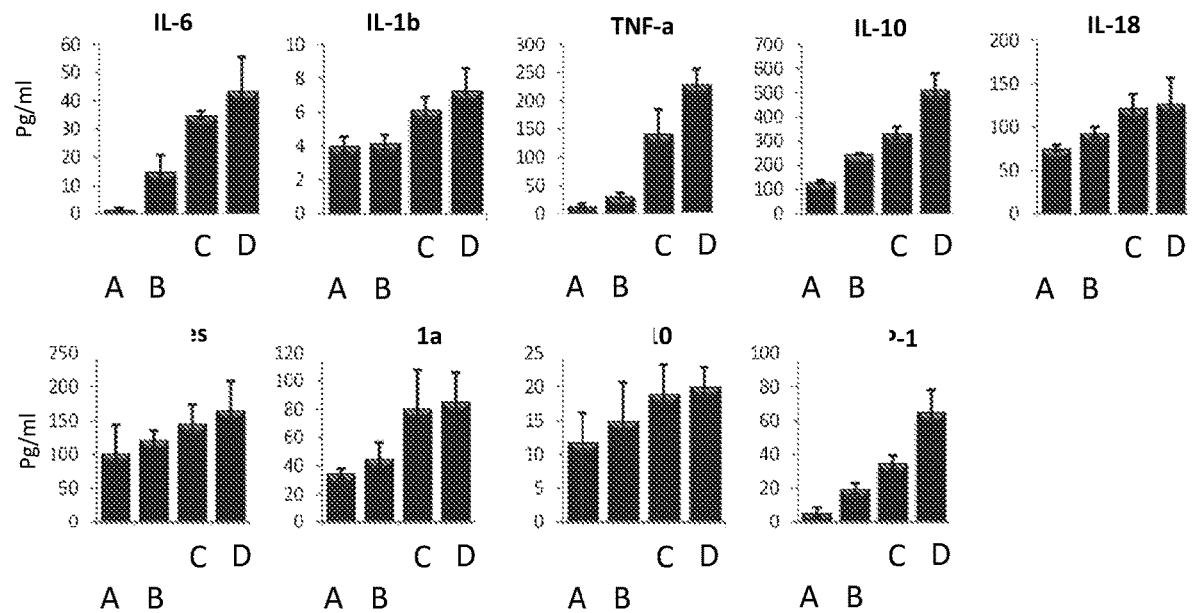
Figure 9:
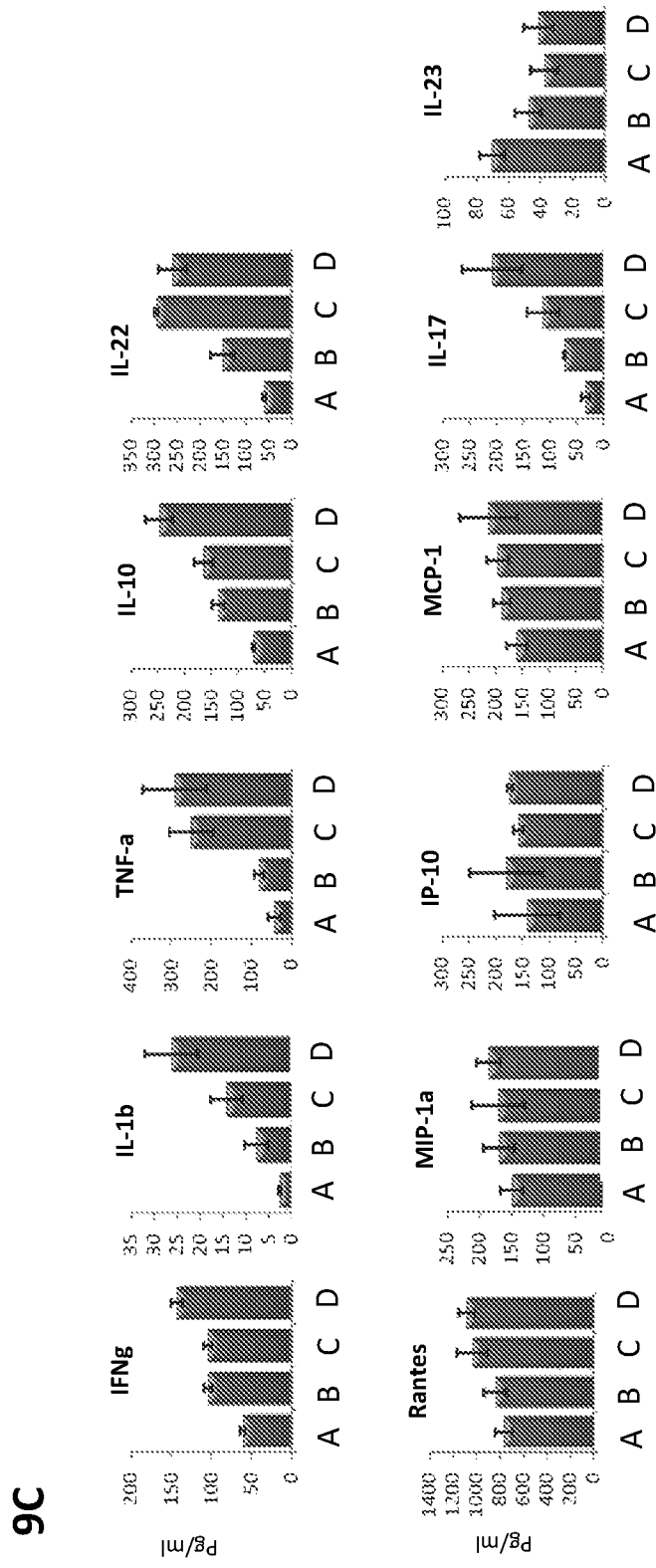

BALB/c mice (6/group) were given the purified beta-1,3-glucan product by oral gavage for 7 days. The mice were administered doses of 0 mg/kg (A), 5 mg/kg (B), 20 mg/kg (C), and 200 mg/kg (D). On day 8, dendritic cells (DCs; CD11c+ cells) were isolated from collagenase digested small intestine by magnetic sorting and cultured overnight. The supernatants were tested for various cytokine and chemokine factors by luminex multiplex assay. As shown in FIG. 9A, increasing amounts of beta-1,3-glucan increased production of IL-1b, TNF-α, IL-10, IL-18, IP-10, and MCP-1. The dose effect was less pronounced for Rantes and MIP-1a, as the level of these chemokines was high and relatively unchanged for beta-1,3-glucan administered at doses of 5, 20, and 200 mg/kg. Expression of IFN-g, IL-12, IL-6, IL-9, IL-2, IL-23, GMCSF, IL-4, and IL-5 was not detectable.

BALB/c mice (6/group) were given the purified beta-1,3-glucan product by oral gavage for 7 days. The mice were administered doses of 0 mg/kg (A), 5 mg/kg (B), 20 mg/kg (C), and 200 mg/kg (D). On day 8, macrophages (F4/80 cells) were isolated from collagenase digested small intestine by magnetic sorting and cultured overnight. The supernatants were tested for various cytokine and chemokine factors by luminex multiplex assay. FIG. 9B shows that increasing amounts of beta-1,3-glucan increased production of IL-6, IL-1b, TNF-α, IL-10, IL-18, Rantes, MIP-1a, IP-10, and MCP-1. Expression of IFN-g, IL-17, IL-22, IL-4, IL-9, IL-18, IL-2, IL-23, and GMCSF was not detectable.

BALB/c mice (6/group) were given the purified beta-1,3-glucan product by oral gavage for 7 days. The mice were administered doses of 0 mg/kg (A), 5 mg/kg (B), 20 mg/kg (C), and 200 mg/kg (D). On day 8, NK1.1+ cells (NK cells) were isolated from collagenase digested small intestine by magnetic sorting and cultured overnight. The supernatants were tested for various cytokine and chemokine factors by luminex multiplex assay. FIG. 9C shows that increasing amounts of beta-1,3-glucan increased production of IFNg, IL-1b, TNF-α, IL-10, IL-22, Rantes, and IL-17. In contrast, the effect of beta-1,3-glucan on expression of MIP-1a, IP-10, and MCP-1 appears to be relatively independent of the administered beta glucan dosage. The production of IL-23 decreased with increasing amounts of beta-1,3-glucan. Expression of IL-6, IL-4, IL-9, IL-2, and GMCSF was not detectable.

Example 7: Treatment of Hyperlipidemia in Mice by Administering Beta-1,3-Glucan Derived from *Euglena*

*Euglena* was grown in a sterile fermenter as described herein. Once the target density of *Euglena* biomass was reached in the fermenter, the *Euglena* was filtered, lysed and the beta-1,3-glucan was purified. The purified beta-1,3-glucan derived from *Euglena* was used in the mice experiment described below. Phosphate buffered saline was administered as a control.

Figure 10:
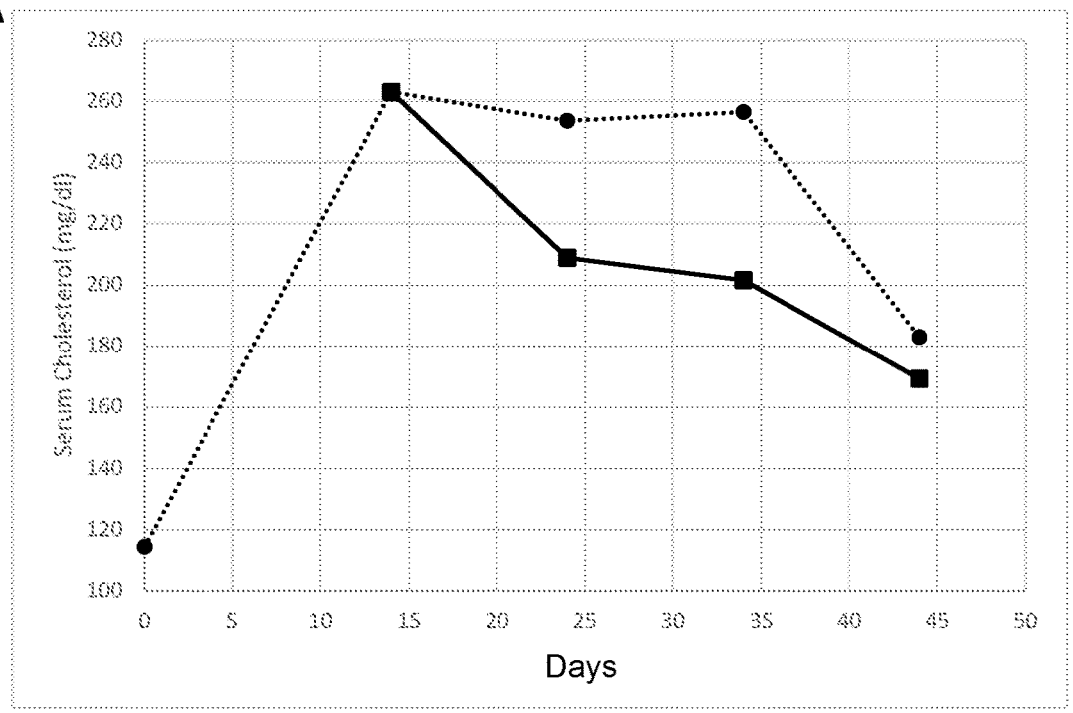
FIG. 10 graphically shows (A) serum cholesterol levels and (B) serum triglyceride levels in mice fed a high cholesterol diet without beta glucans for 14 days, followed by a diet with normal levels of cholesterol that contained a beta glucan product (or control diet) for an additional 30 days. Beta glucan was administered at a dose of 20 mg/kg. Serum was collected from the mice after 12 hours of food deprivation. The dotted lines represent the PBS control, and the solid lines represent purified beta glucan derived from *Euglena*.
Figure 10:
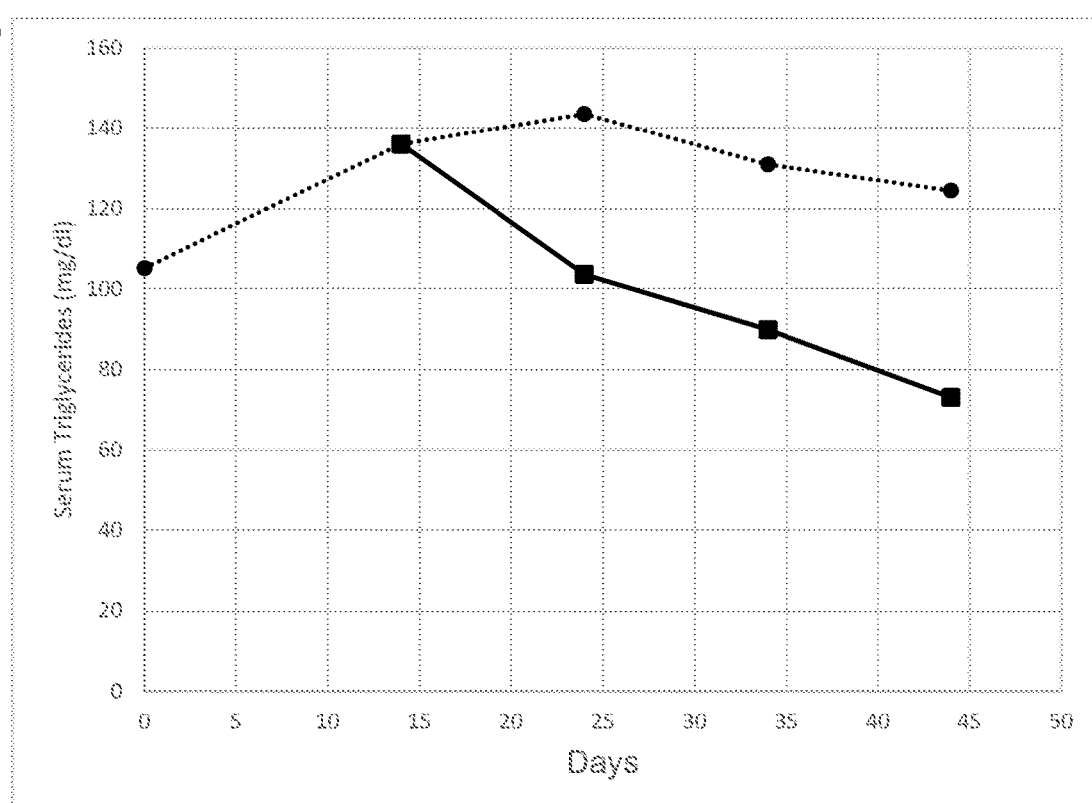

In a first experiment, Balb/c mice were fed a high-cholesterol diet (approximately 16 mg cholesterol daily) free of beta glucans for 14 days. After this period, the mice were fed a diet with normal levels of cholesterol (approximately 110 mg/dL) that contained purified beta-1,3-glucan derived from *Euglena* or the control for an additional 30 days. Serum was collected after 12 hours of food deprivation and blood cholesterol and triglycerides were measured. As illustrated in FIG. 10A, serum cholesterol levels in the mice rose during the high-cholesterol diet from an average of about 115 mg/dL to about 265 mg/dL. For the control mice administered phosphate buffered saline after return to a diet with normal amounts of cholesterol, the cholesterol levels remained elevated until at least day 34, and decreased to about 181 mg/dL by day 44. In contrast, mice administered the beta-1,3-glucan derived from *Euglena* saw an immediate and steady decline in blood cholesterol levels. Similar results were obtained for triglyceride levels. As seen in FIG. 10B, serum triglyceride levels rose from about 105 mg/dL to about 138 mg/dL while the mice consumed a high-cholesterol diet. The control mice saw only a slight decrease in serum triglyceride levels after 30 days on the normal-cholesterol diet. In contrast, mice administered beta glucan saw an immediate and continuous decrease in serum triglyceride levels, which by day 44 were lower than the start of the experiment.

Figure 11:
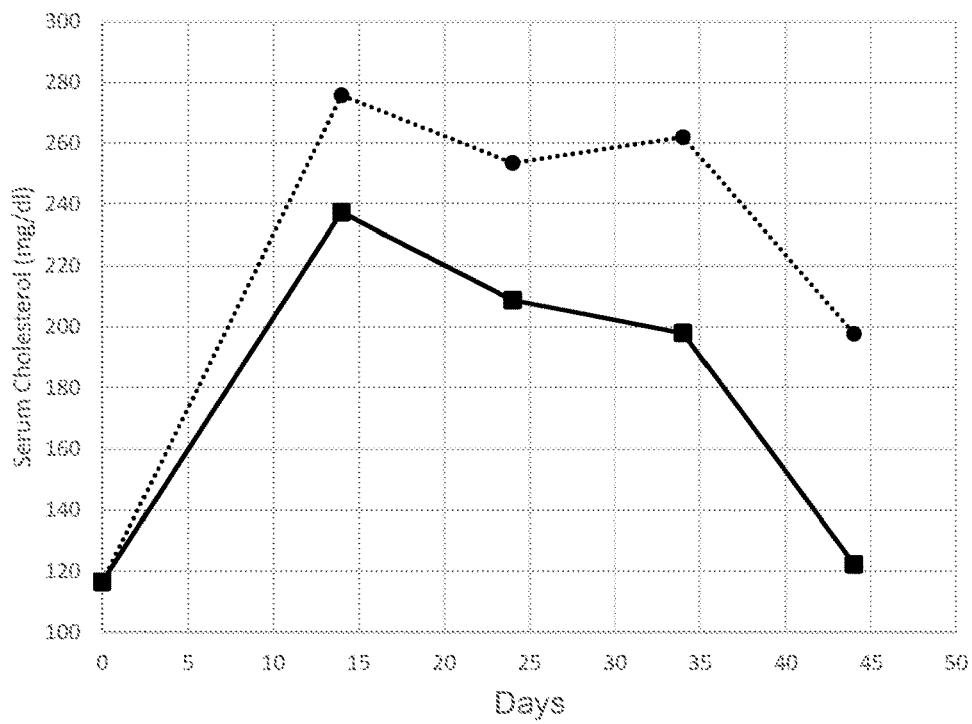
FIG. 11 graphically shows (A) serum cholesterol levels and (B) serum triglyceride levels in mice a high cholesterol diet with beta glucans (or control diet) for 14 days, followed by a diet with normal levels of cholesterol that contained a beta glucan product (or control diet) for an additional 30 days. Beta glucan was administered at a dose of 20 mg/kg. Serum was collected from the mice after 12 hours of food deprivation. The dotted lines represent the PBS control, and the solid lines represent purified beta glucan derived from *Euglena*.
Figure 11:
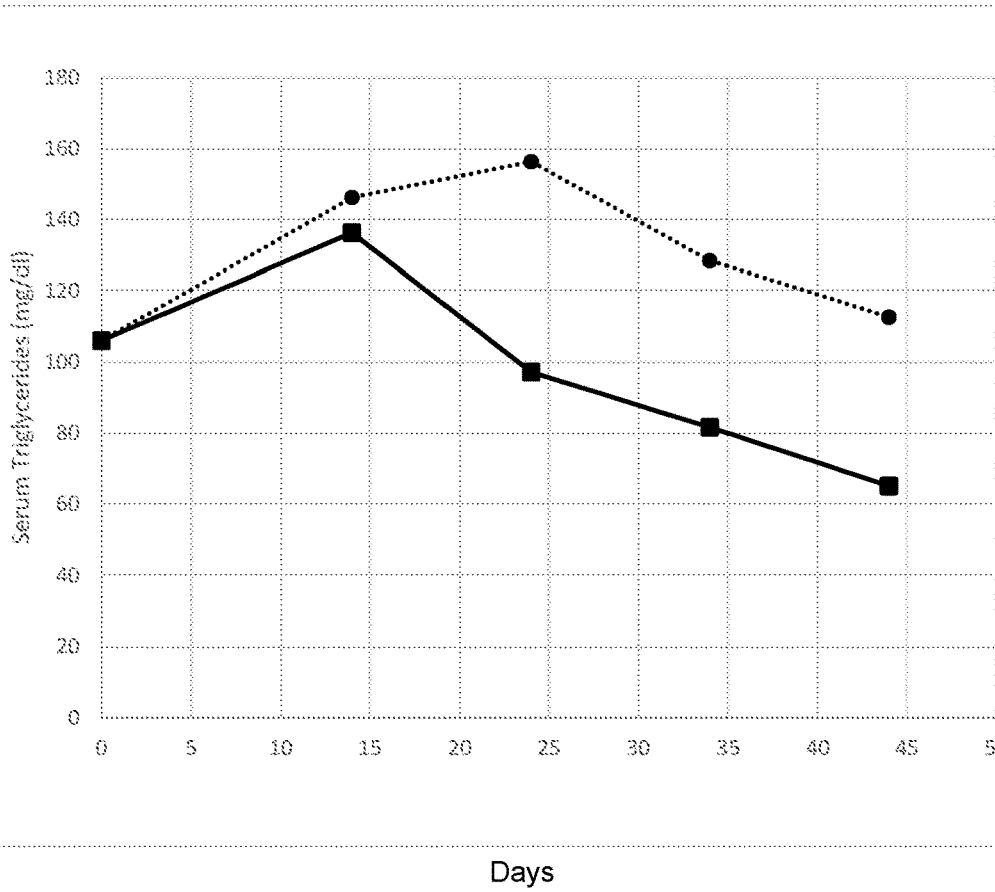

In a second experiment, Balb/c mice were fed a high-cholesterol diet (approximately 16 mg cholesterol daily) in conjunction with purified beta-1,3-glucan derived from *Euglena* or the control for 14 days. After the 14 days, the mice were fed a normal-cholesterol diet (approximately 110 mg/dL) and administered the same beta-glucan product or control for an additional 30 days. Serum was collected after 12 hours of food deprivation and blood cholesterol and triglycerides were measured. As illustrated in FIG. 11A, serum cholesterol of the mice administered only the control rose the most during the 14 days with the high-cholesterol diet, rising from about 118 mg/dL to about 275 mg/dL. The mice administered purified beta-1,3-glucan derived from *Euglena* showed a smaller increase of blood serum cholesterol, from about 118 mg/dL to about 230 mg/dL. Similar results were obtained for triglyceride levels. As seen in FIG. 11B, serum triglyceride levels of the control mice increased the most while being fed the high-cholesterol diet (from about 105 mg/dL to about 145 mg/dL). The control mice saw only a slight decrease in serum triglyceride levels after 30 days on the normal-cholesterol diet. In contrast, mice administered beta glucan saw an immediate and continuous decrease in serum triglyceride levels after returning to the normal-cholesterol diet, which by day 44 were lower than the start of the experiment.

Example 8: Clinical Study to Assess the Effect of Consuming Beta-1,3-Glucan Derived from *Euglena* on Metabolic Health in Individuals A clinical trial is used to evaluate the effects of consuming beta-1,3-glucan derived from *Euglena* on cholesterol levels, blood sugar levels, infection, and inflammation. Participants are recruited after providing written informed consent (as approved by a registered Institutional Review Board) and a screening process. The study is 4 weeks in duration and evaluations take place at baseline, 2, and 4 weeks of beta-1,3-glucan consumption. Beta-1,3-glucan derived from *Euglena* is administered in capsule form to provide a daily dose of 250 mg to each individual.

The effect of beta glucan on metabolic health is measured using one or more of the following: fasting blood levels of markers pertaining to glucose and lipid metabolism, evaluation of general health and wellness, and determination of blood pressure and blood chemistry. Analysis of blood chemistry can include protein carbonyl content (a marker for oxidative stress), acute phase inflammatory markers (such as C-reactive protein, alpha-1 acid glycoprotein, fibrinogen, and platelet factor-4), metabolic biomarkers (such as C-peptide, cortisol, pancreatic polypeptide, proinsulin, and peptide YY), cytokine panel, and antibody analysis.

Intestinal Inflammation

Example 9: Oral Administration of *Euglena* Biomass Comprising Beta-1,3-Glucan

*Euglena* is grown using fermentation in a bioreactor using a repeated-batch process. In the final step, the *Euglena* is grown to a cell density of about 40 grams dry weight per liter to about 80 grams dry weight per liter and harvested. The *Euglena* cells have a beta-1,3-glucan content of about 50 wt %. The *Euglena* cell culture is filtered using tangential flow filtration, the spent growth media disposed, and the cells washed in water. The resulting *Euglena* biomass is rolled into thin sheets and dried to a moisture content of less than 10%. The dried biomass is milled to less than 1000 microns and the *Euglena* biomass is then orally administered to a human to treat intestinal inflammation.

Example 10: Oral Administration of *Euglena* Biomass Comprising Beta-1,3-Glucan as a Nutritional Supplement

*Euglena* is grown using fermentation in a bioreactor using a repeated-batch process. In the final step, the *Euglena* is grown to a cell density of about 40 grams dry weight per liter to about 80 grams dry weight per liter and harvested. The *Euglena* cells have a beta-1,3-glucan content of about 50 wt %. The *Euglena* cell culture is filtered using tangential flow filtration, the spent growth media disposed, and the cells washed in water. The *Euglena* biomass is then dried in a drum dryer to a moisture content of less than 5%. The dry flakes are processed into a powder using a hammer mill with an average grain size of less than 250 microns. The powder is then formed into tablets for oral administration to treat intestinal inflammation. Alternatively, the powder is mixed with a food product and orally administered with the food product to treat intestinal inflammation. Alternatively, the powder is placed into a capsule for oral administration to treat intestinal inflammation.

Example 11: Purification of Beta-1,3-Glucan from *Euglena*

In one exemplary embodiment, beta-1,3-glucan is purified from *Euglena* by heating *Euglena* grown by fermentation as described herein in a 1% sodium dodecyl sulfate solution, centrifuging the solution, and washing the pellet with water and ethanol. Approximately one part *Euglena* biomass (dry weight basis) is suspended in 5 parts of 1% (w/v) sodium dodecyl sulfate solution. This suspension is mixed and then heated to about 100° C. for about 30 minutes. The solution is then cooled and centrifuged at >500 RCF for about 5 minutes. The supernatant is discarded and the pellet is washed by re-suspension in 10 parts water, mixed vigorously and centrifuged at >500 RCF for 5 minutes. The washing process can be repeated two more times with 10 parts 95% ethanol, to arrive at a 95% pure beta glucan pellet. The pellet can be further dried to a white powder.

In another exemplary embodiment, beta-1,3-glucan is purified from Euglena by pumping Euglena grown by fermentation as described herein through a high pressure homogenizer to lyse the cells. The lysed mixture is then centrifuged to recover the beta-1,3-glucan. The supernatant is discarded and the pellet is washed by re-suspension in water, mixed vigorously and centrifuged at >500 RCF. The washing process can be repeated two more times with 10 parts water, to arrive at a 95% pure beta-1,3-glucan pellet. The pellet can be further dried to a white powder.

The methods described herein are less toxic than some of the previous methods described for extracting beta-1,3-glucan, which may have added benefit of receiving safety and all-natural product certifications necessary for producing a food-grade or nutraceutical-grade product. The resulting purified beta-1,3-glucan is then formed into tablets for oral administration or mixed with a food product and orally administered. Alternatively, the purified beta-1,3-glucan can be mixed with an aqueous solution as a pharmaceutical composition. The pharmaceutical composition may further comprise a pharmaceutically acceptable excipient. The pharmaceutical composition can then be intravenously administered.

Example 12: In Vivo Study to Determine the Effect of Pre-Treatment of Beta-1,3-Glucan Derived from Euglena on Chemically Induced Acute Colitis Euglena biomass comprising beta-1,3-glucan was grown using fermentation processes as described herein. The dried Euglena biomass and purified beta glucan extract were tested in a mouse study. The dried Euglena biomass was produced from Euglena cells grown on glucose as the organic carbon source. The Euglena biomass contained about 50 wt % beta-1,3-glucan and was centrifuged and then dried without any further processing. Fractionating the Euglena biomass product to isolate the beta-1,3-glucan and then repeatedly washing the beta glucan fraction to remove non-beta glucan cell components produced the purified sample of beta-1,3-glucan. The purified sample comprised about 95 wt % beta-1,3-glucan. Phosphate buffered saline (PBS) was used as a negative control.

The dried Euglena biomass sample and purified beta-1, 3-glucan sample were dried and ground to particle sizes of less than 500 microns. These dry powders were then mixed with PBS buffer and diluted to appropriate concentrations before being dosed by gavage to C57BL/6J mice. For the duration of the trial (15 days), mice were treated once per day after 2 hours of fasting with either (i) PBS ("None"), (ii) dried Euglena biomass ("A50"; 250 μg/mouse/day), or (iii) purified beta-1,3-glucan ("AG"; 125 μg/mouse/day). This dosing ensured that mice administered the dried Euglena biomass received an equivalent dose of beta-1,3-glucan as the mice administered the purified beta-1,3-glucan. Ten mice were used in each treatment group. After 5 days (Day 0), mice were administered a 2.5% solution of dextran sodium sulfate (DSS), a compound known to induce acute colitis, in their drinking water until Day 5, and then switched back to regular water. Body weight and visual observations were performed each day. Mice were euthanized on Day 10. Colon samples were processed and immune cells were isolated for cytokine analyses. The effect of pre-treatment of beta-1,3-glucan derived from Euglena on chemically induced acute colitis as determined using a variety of parameters is described in Examples 13-19.

Figure 12:
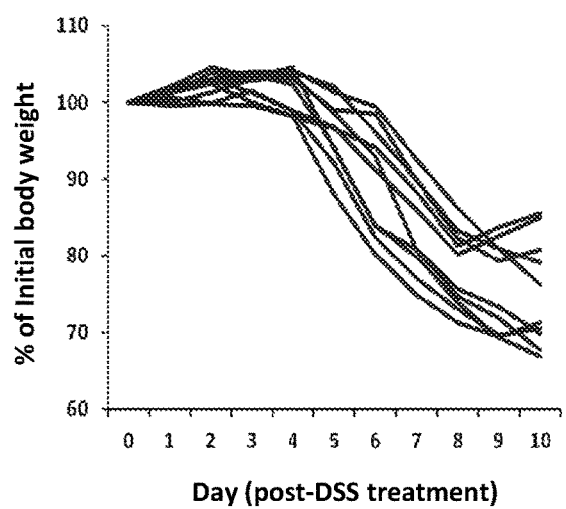
FIG. 12A graphically shows the effect on body weight of administering PBS ("None") to mice with DSS-induced colitis.
FIG. 12B graphically shows the effect on body weight of administering purified beta-1,3-glucan (>99 wt %) ("AG") to mice with DSS-induced colitis.
FIG. 12C graphically shows the effect on body weight of administering dried *Euglena gracilis* containing about 50 weight % beta-1,3-glucan ("A50") to mice with DSS-induced colitis.
Figure 12:
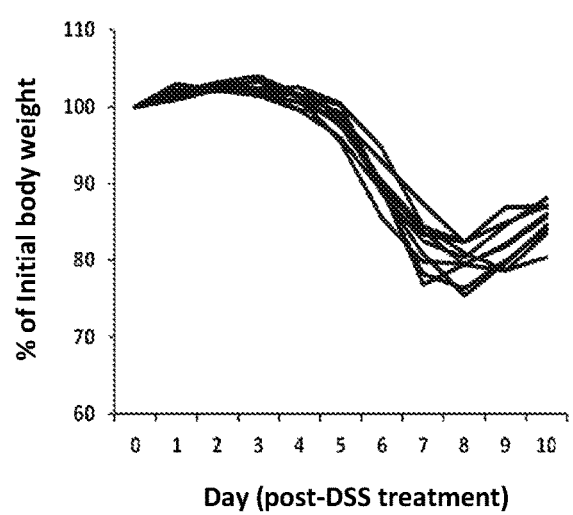
Figure 12:
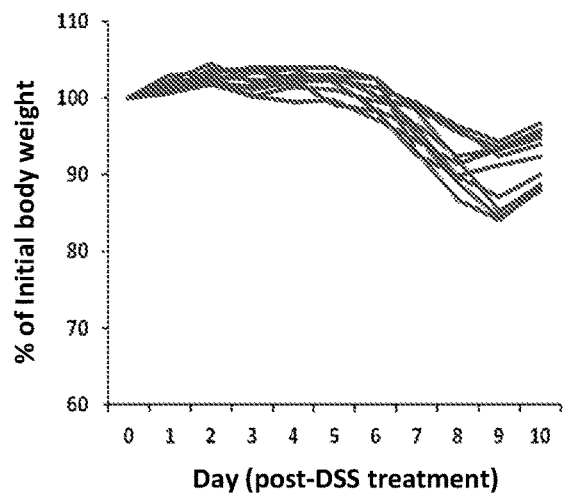

Example 13: Effect of Pre-Treatment of Beta-1,3-Glucan Derived from Euglena on Body Weight in Mice with Chemically Induced Acute Colitis Mice were treated as described in Example 12. Body weight of each mouse was recorded every day during the experiment. Loss of body weight is considered a sign of colitis. Initial body weight was considered as 100% for calculating percentage of body weight for subsequent time points. The percent of initial body weight was measured as a function of time following DSS treatment (FIG. 12A-12C). The statistical significance of this data is presented in Table 2.

TABLE 2

| p- values of t-test for body weight data (% of initial body weight). | | | | | | | | | | | |
|---|---|---|---|---|---|---|---|---|---|---|---|
| Day | 0 | 1 | 2 | 3 | 4 | 5 | 6 | 7 | 8 | 9 | 10 |
| A50 | 0 | 0.1971 | 0.3156 | 0.9217 | 0.4897 | 0.0042 | 0.0017 | 0.0003 | 0.0002 | 0.0014 | 0.0004 |
| AG | 0 | 0.1246 | 0.5088 | 0.7166 | 0.6594 | 0.1861 | 0.8449 | 0.2767 | 0.2303 | 0.0058 | 0.0017 |

Mice treated with either PBS (FIG. 12A) or purified beta-1,3-glucan (FIG. 12B) showed a sharp decrease in body weight by Day 5 following DSS treatment. By Day 10, the body weight of mice treated with PBS fell to approximately 75% of initial body weight. Mice treated with purified beta-1,3-glucan showed a similar decrease in body weight from Day 5 to Day 8, falling to approximately 80% of initial body weight. However, on Days 9 and 10, the body weight of mice treated with purified beta-1,3-glucan increased to approximately 83% and 85%, respectively. The data suggests that treatment using purified beta-1,3-glucan is effective for early recovery from DSS-induced acute colitis, particular when taken together with other factors (such as stool consistency and presence of fecal blood).

Mice treated with dried Euglena biomass showed no significant decrease in body weight until Day 6 following DSS treatment, at which time a gradual decrease in body weight was observed (FIG. 12C). By Day 9, the body weight of mice treated with dried Euglena biomass decreased to approximately 92% of initial body weight. However, the body weight of mice treated with dried Euglena biomass increased slightly on Day 10 to approximately 95%. The data show that treatment using dried Euglena biomass is effective at preventing or minimizing the severity of acute colitis induced by DSS in mice.

Figure 13:
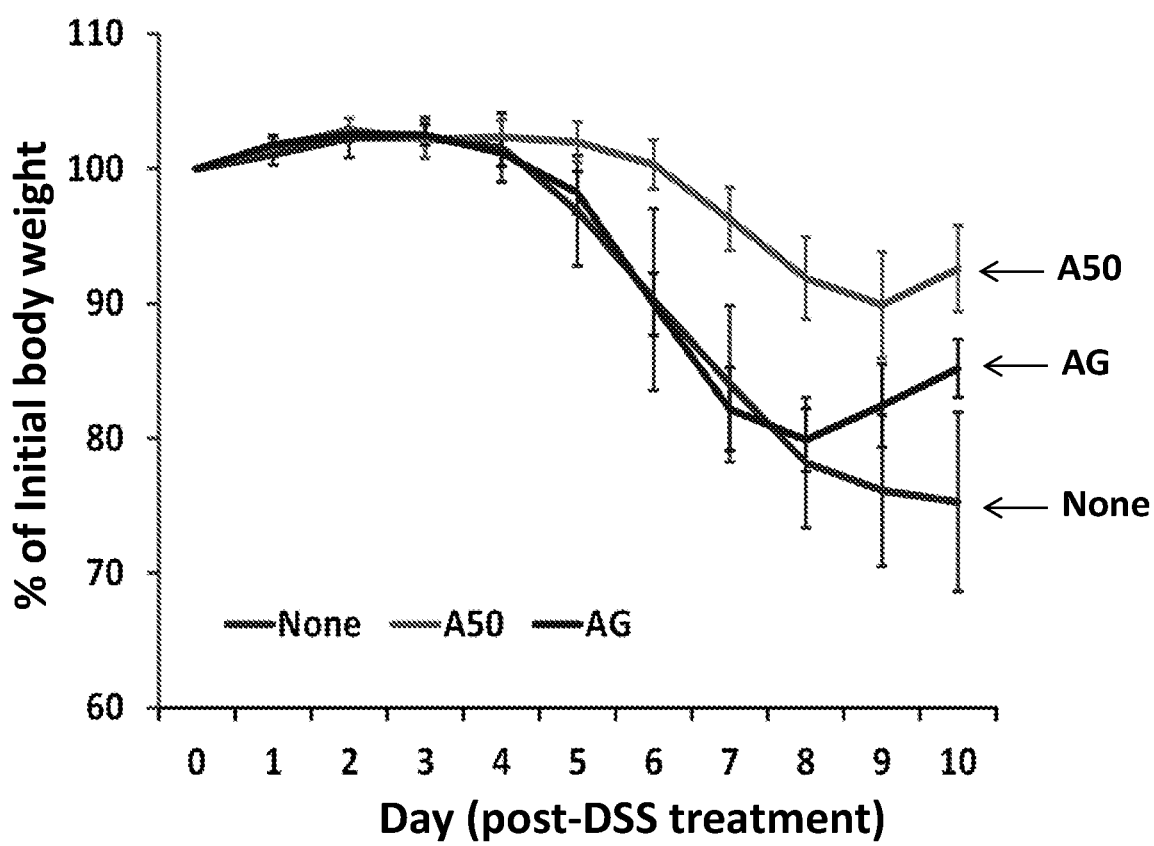
FIG. 13 graphically shows the effect of beta-1,3-glucan on body weight of mice with DSS-induced colitis. The graph depicts the combined results of mice treated with PBS ("None"), purified beta-1,3-glucan ("AG"), or dried *Euglena gracilis* ("A50") based on % of initial body weight as a function of time. Bars represent means±standard error (n=10 mice per treatment group).
Figure 14:
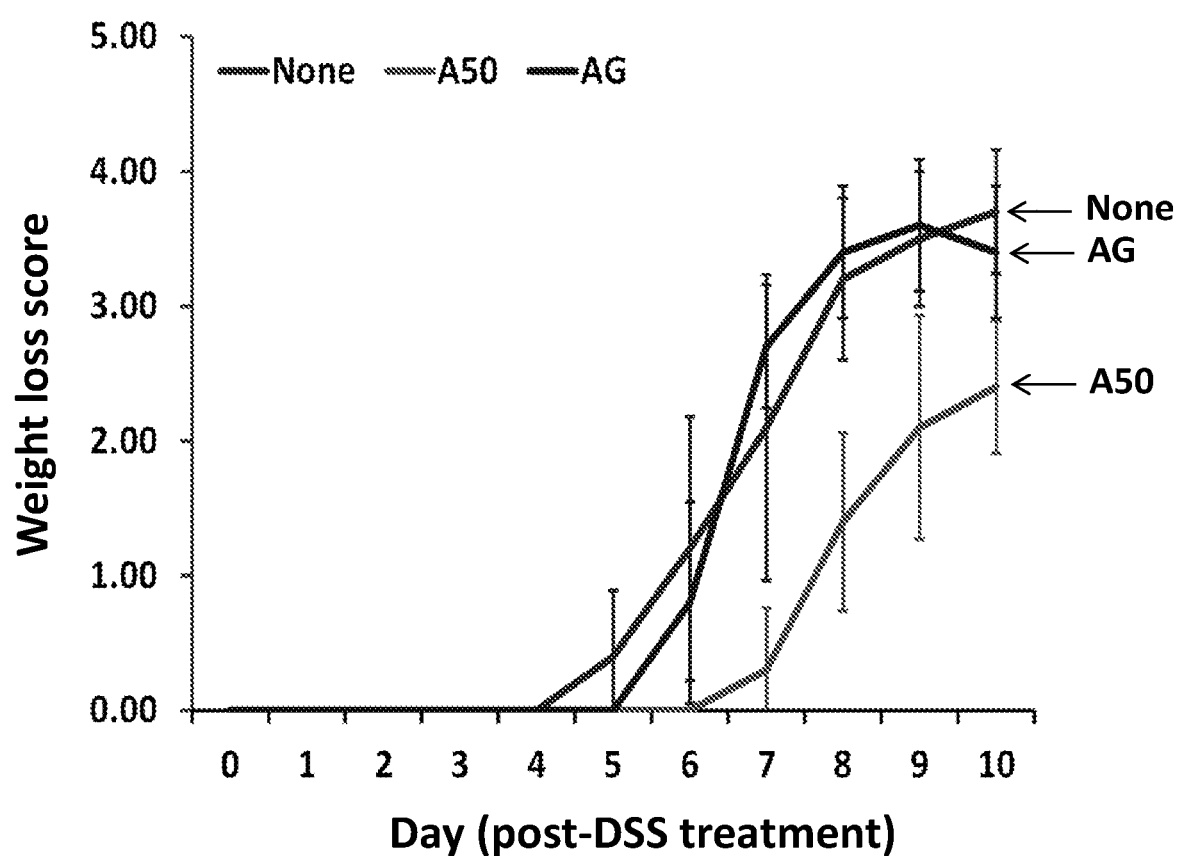
FIG. 14 graphically shows the effect of beta-1,3-glucan on body weight of mice with DSS-induced colitis. The graph depicts the combined results of mice treated with PBS ("None"), purified beta-1,3-glucan ("AG"), or dried *Euglena gracilis* ("A50") based on weight loss score as a function of time. Weight loss scores were calculated as follows: 0 (no loss), 1 (1-5%), 2 (5-10%), 3 (10-20%), and 4 (>20%). Bars represent means±standard error (n=10 mice per treatment group).

The combined results of mice treated with PBS, purified beta-1,3-glucan, or dried Euglena biomass are shown in FIG. 13. The combined results of mice treated with PBS, purified beta-1,3-glucan, or dried Euglena biomass are also represented as a function of weight loss score over time (FIG. 14). Weight loss scores were calculated as follows: 0 (no loss), 1 (1-5%), 2 (5-10%), 3 (10-20%), and 4 (>20%).

The statistical significance of this data is presented in Table 3.

TABLE 3 p- values of t-test for body weight data (weight loss score).

| Day | 0 | 1 | 2 | 3 | 4 | 5 | 6 | 7 | 8 | 9 | 10 |
|---|---|---|---|---|---|---|---|---|---|---|---|
| A50 | | | | | 0.036878 | 0.005121 | 0.002798 | 0.000725 | 0.004405 | 0.000746 | 0.000746 |
| AG | | | | | 0.036787 | 0.343436 | 0.051003 | 0.343436 | 0.343436 | 0.193422 | 0.010708 |

Figure 15:
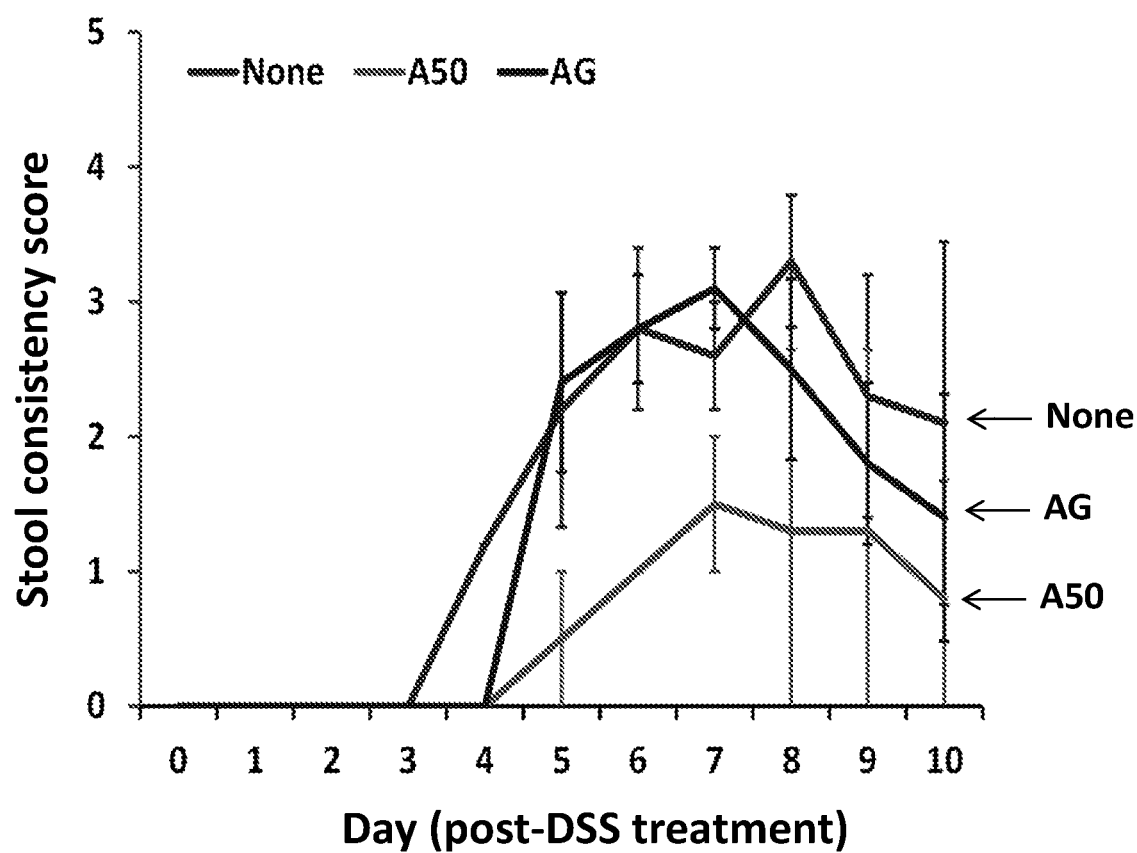
FIG. 15 graphically shows the effect of beta-1,3-glucan on stool consistency of mice with DSS-induced colitis. The graph depicts the combined results of mice treated with PBS ("None"), purified beta-1,3-glucan ("AG"), or dried *Euglena gracilis* ("A50"). Stool consistency was scored as follows: 0 (normal solid), 2 (semisolid/soft), 3 (loose stool), and 4 (watery/diarrhea). Bars represent means±standard error (n=10 mice per treatment group).

Example 14: Effect of Pre-Treatment of Beta-1,3-Glucan Derived from *Euglena* on Stool Consistency in Mice with Chemically Induced Acute Colitis Mice with chemically-induced acute colitis were treated as described in Example 12. Stool consistency of each mouse was recorded every day during the experiment. Loss of body weight is considered a sign of colitis. Stool consistency was scored as follows: 0 (normal solid), 2 (semisolid/soft), 3 (loose stool), and 4 (watery/diarrhea). The stool consistency was determined as a function of time following DSS treatment (FIG. 15). The statistical significance of this data is presented in Table 4.

TABLE 4 p- values of t-test for stool consistency data.

| Day | 0 | 1 | 2 | 3 | 4 | 5 | 6 | 7 | 8 | 9 | 10 |
|---|---|---|---|---|---|---|---|---|---|---|---|
| A50 | | | | | 0.002561 | 0.000108 | 0.0001 | 0.003241 | 0.011508 | 0.21258 | 0.089781 |
| AG | | | | | 0.002561 | 0.508646 | 1 | 0.014956 | 0.00311 | 0.21258 | 0.110765 |

Mice treated with PBS showed normal stool consistency on Days 0-3. Beginning on Day 4, mice treated with PBS developed loose stools. Mice treated with purified beta-1,3-glucan showed normal stool consistency on Days 0-4, and developed loose stools beginning on Day 5. Mice treated with dried *Euglena* biomass produced normal stool consistency until Day 5, at which time semisolid/soft stools were produced. The data show that treatment using dried *Euglena* biomass is particularly effective at preventing or minimizing the severity of acute colitis induced by DSS in mice.

Figure 16:
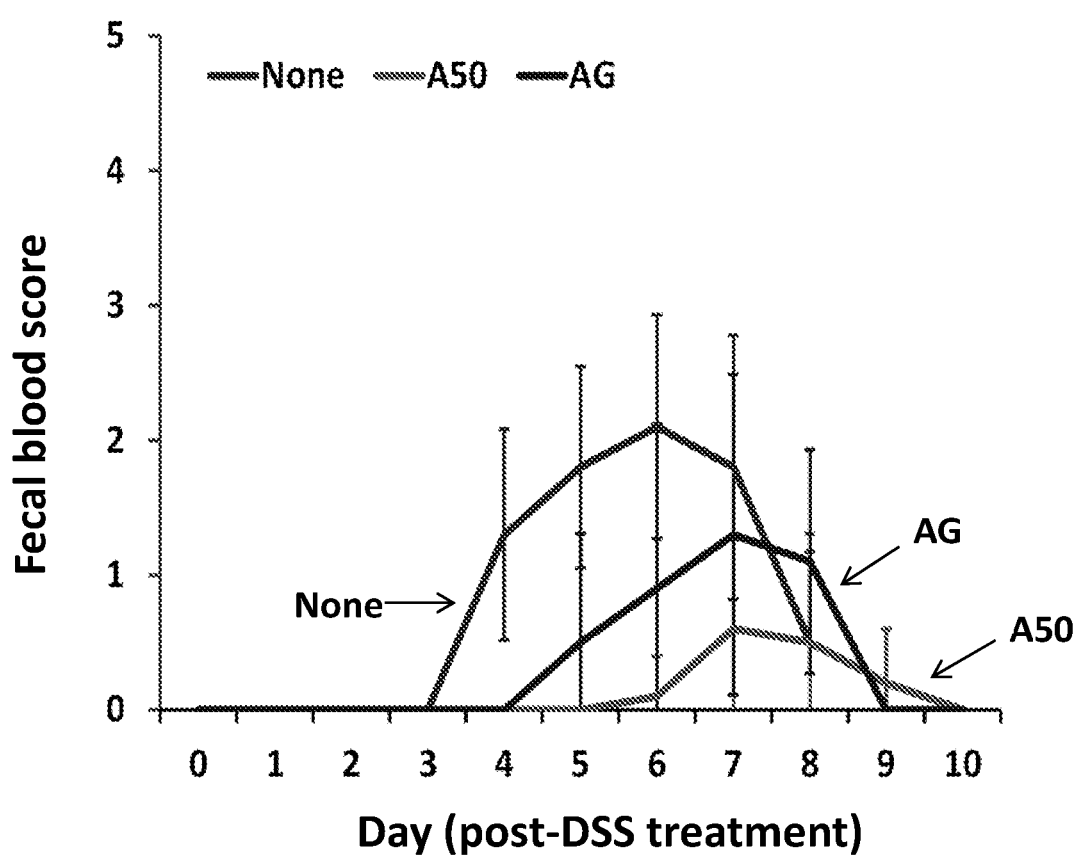
FIG. 16 graphically shows the effect of beta-1,3-glucan on fecal blood in mice with DSS-induced colitis. The graph depicts the combined results of mice treated with PBS ("None"), purified beta-1,3-glucan ("AG"), or dried *Euglena gracilis* ("A50"). Bars represent means±standard error (n=10 mice per treatment group).

Example 15: Effect of Pre-Treatment of Beta-1,3-Glucan Derived from *Euglena* on Fecal Blood in Mice with Chemically Induced Acute Colitis Mice with chemically-induced acute colitis were treated as described in Example 12. The degree of visible fecal blood/rectal bleeding levels of each mouse was recorded every day during the experiment. Fecal blood was scored as follows: 0 (no blood), 1 (red tinge on fecal pellet), 2 (patches of blood on feces), 3 (blood covered/mixed feces), and 4 (gross bleeding/blood around anus). The fecal blood score was recorded as a function of time following DSS treatment (FIG. 16). The statistical significance of this data is presented in Table 5.

TABLE 5 p- values of t-test for fecal blood data.

| Day | 0 | 1 | 2 | 3 | 4 | 5 | 6 | 7 | 8 | 9 | 10 |
|---|---|---|---|---|---|---|---|---|---|---|---|
| A50 | | | | | 0.000746 | $5 \times 10^{-5}$ | $2.86 \times 10^{-5}$ | 0.023856 | 1 | 1 | |
| AG | | | | | 0.000746 | 0.027655 | 0.036787 | 0.397385 | 0.239172 | 0.167851 | |

Mice treated with PBS showed no fecal blood on Days 0-3. Beginning on Day 4, mice treated with PBS developed blood in the feces. Mice treated with purified beta-1,3-glucan showed no fecal blood on Days 0-4, and began to show blood in the feces on Day 5. The amount of fecal blood produced by mice treated with purified beta-1,3-glucan was significantly less than that produced by mice treated with PBS. Mice treated with dried *Euglena* biomass produced no fecal blood until Day 6, at which time minor amounts of fecal blood were evident. The amount of fecal blood produced by mice treated with dried *Euglena* biomass was less than that produced by mice treated with purified beta-1,3-glucan. The data show that treatment using dried *Euglena gracilis* or purified beta-1,3-glucan is effective at preventing or minimizing the severity of acute colitis induced by DSS in mice.

Figure 17:
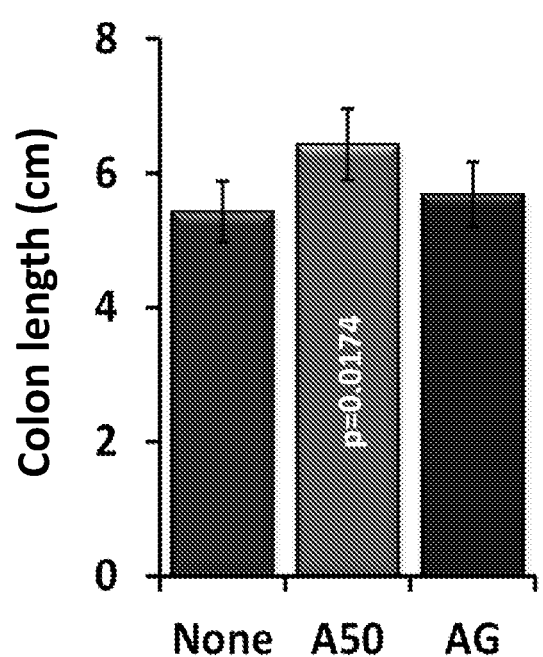
FIG. 17 graphically shows the effect of beta-1,3-glucan on colon length in mice with DSS-induced colitis. The graph shows the colon length at Day 10 of mice treated with PBS ("None"), purified beta-1,3-glucan ("AG"), or dried *Euglena gracilis* ("A50"). Bars represent means±standard error (n=7 mice per treatment group).

Example 16: Effect of Pre-Treatment of Beta-1,3-Glucan Derived from *Euglena* on Colon Length in Mice with Chemically Induced Acute Colitis Mice with chemically-induced acute colitis were treated as described in Example 12. The length of the colon of individual mice was measured following euthanasia of mice on Day 10 (7 mice/treatment group). The data is presented in FIG. 17. The colon length of mice treated with PBS or purified beta-1,3-glucan are within error, but the colon length of mice treated with dried *Euglena* biomass is significantly increased. Specifically, the colon length of mice treated with PBS is approximately 5.5 cm, whereas the colon length of mice treated with dried *Euglena gracilis* is approximately 6.5. The data show that treatment using dried *Euglena* biomass is particularly effective at preventing or minimizing the severity of acute colitis induced by DSS in mice.

Figure 18:
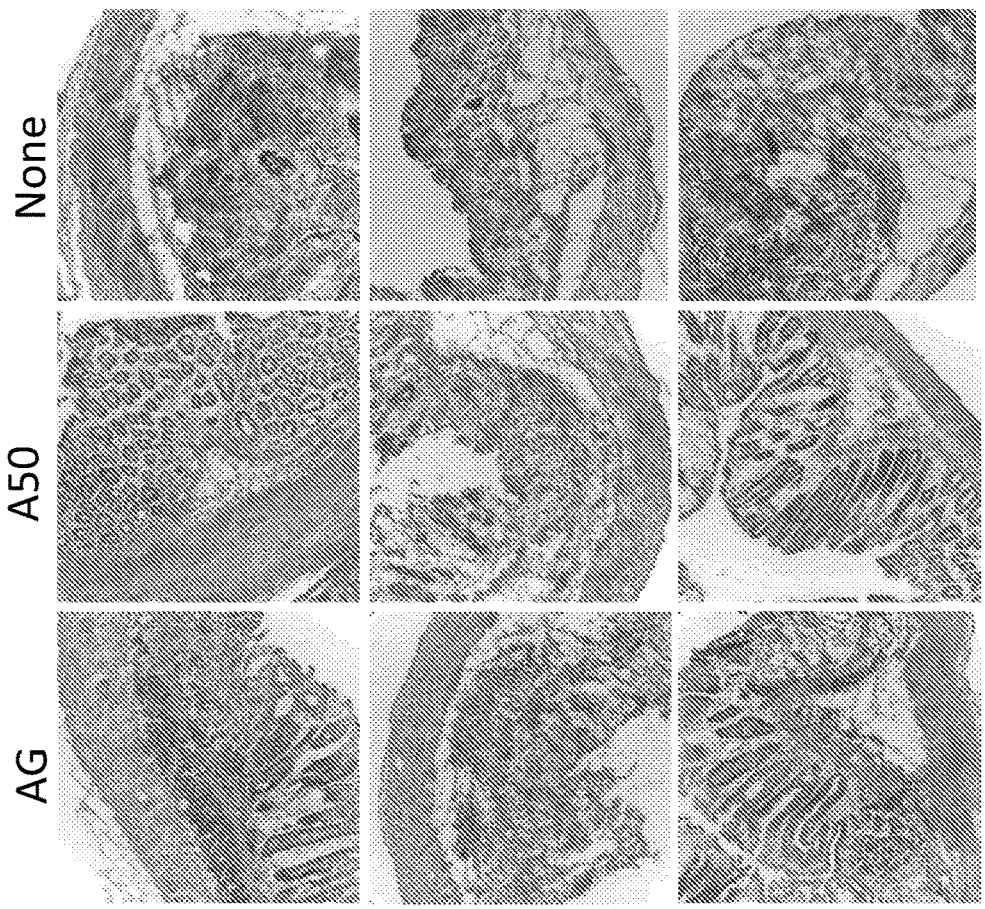
FIG. 18A shows representative images of colonic inflammation at Day 10 of mice treated with PBS ("None"), purified beta-1,3-glucan ("AG"), or dried *Euglena gracilis* ("A50"). Images were obtained under a light microscope using a 10× objective lens.
FIG. 18B graphically shows the effect of beta-1,3-glucan on the severity of colonic inflammation in mice with DSS-induced colitis that were treated with PBS ("None"), purified beta-1,3-glucan ("AG"), or dried *Euglena gracilis* ("A50"). Bars represent means±standard error (n=3 mice per treatment group).
Figure 18:
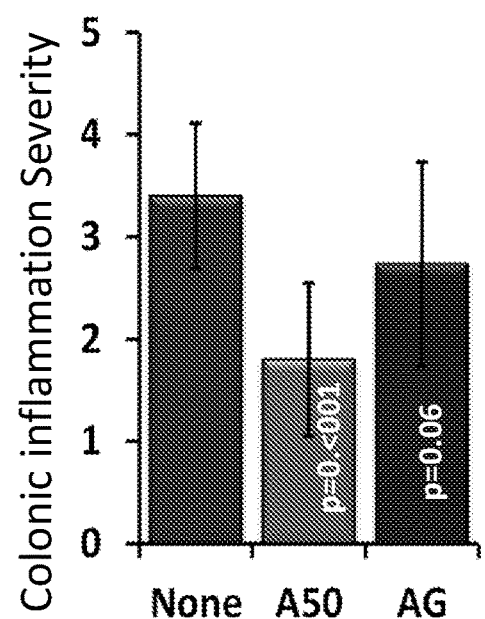

Example 17: Effect of Pre-Treatment of Beta-1,3-Glucan Derived from *Euglena* on Colonic Inflammation in Mice with Chemically Induced Acute Colitis Mice with chemically-induced acute colitis were treated as described in Example 12. The degree of colonic inflammation was determined following euthanasia of mice on Day 10 (3 mice/treatment group). Distal colon pieces were snap frozen, cryo-sectioned (6 μm sections), and subjected to hematoxylin/Eosin staining. Representative images for each treatment group are shown in FIG. 18A. The severity of colonic inflammation in individual mice was also graded (0-4) based on immune cell infiltration and damage to overall architecture of mucosa and submucosa by a pathologist (FIG. 18B). A total of 15 sections (each at 500 μm distance) were examined for 3 mice.

Of the three treatment groups, mice treated with PBS showed the highest level of colonic inflammation (graded as approximately 3.4). Mice treated with purified beta-1,3-glucan showed slightly lower levels of colonic inflammation (graded as approximately 2.8), and mice treated with dried *Euglena gracilis* had the lowest levels of colonic inflammation (graded as approximately 1.8). The data show that treatment using dried *Euglena gracilis* or purified beta-1,3-glucan is effective at preventing or minimizing the severity of acute colitis induced by DSS in mice.

Figure 19:
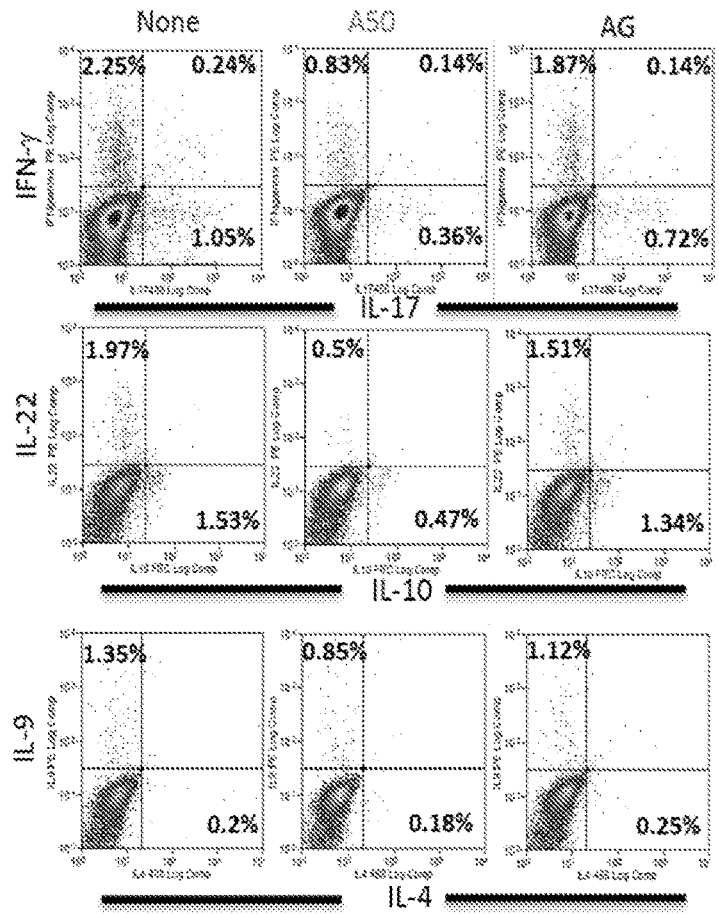
FIG. 19A shows representative FACS analysis images of T helper cell frequencies at Day 10 of mice treated with PBS ("None"), purified beta-1,3-glucan ("AG"), or dried *Euglena gracilis* ("A50").
FIG. 19B graphically shows the effect on production of cytokine positive cells of administering PBS ("None"), purified beta-1,3-glucan ("AG"), or dried *Euglena*
Figure 19:
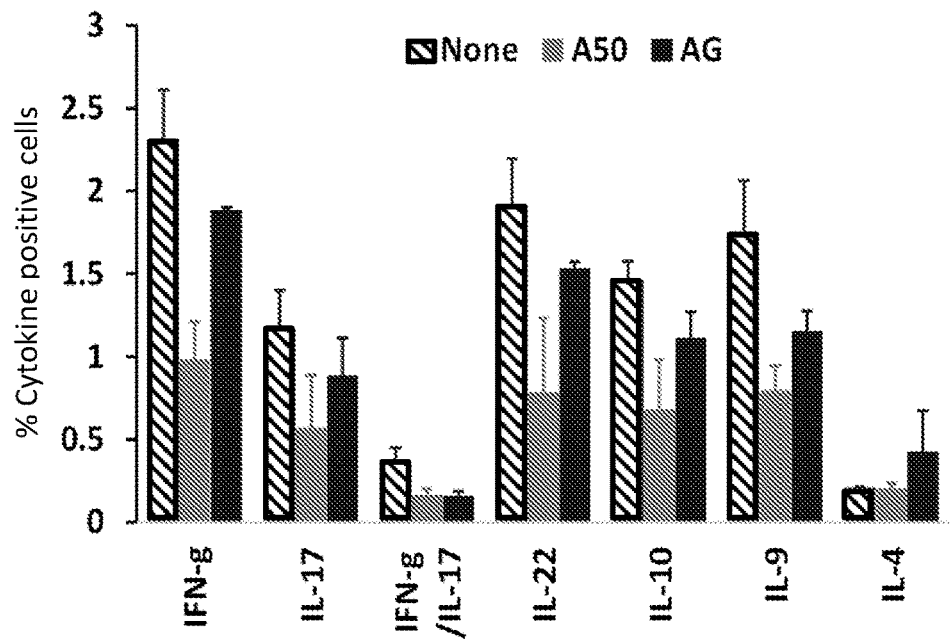

Example 18: Effect of Pre-Treatment of Beta-1,3-Glucan Derived from *Euglena* on T Helper Cell Response in Mice with Chemically Induced Acute Colitis Mice with chemically-induced acute colitis were treated as described in Example 12. The frequency of cytokines related to T helper cell function was analyzed in individual mice on Day 10 (3 mice/treatment group). Mesenteric lymph node cells were activated using PMA/Ionomycin, stained for the presence of cytokines related to T helper cell function, and analyzed by FACS (FIG. 19A). The percent of cytokine positive cells is shown in FIG. 19B.

Mice treated with dried *Euglena* biomass showed significantly lower frequencies of Th1 (IFN-γ), Th17 (IL-17 and IL-22), and Th9 (IL-9) producing CD4+ T cells than mice treated with PBS. Mice treated with purified beta-1,3-glucan show relatively lower levels of Th1 (IFN-γ) producing CD4+ T cells than mice treated with PBS. The statistical significance of this data is presented in Table 6.

TABLE 6

| | p- values of t-test for cytokine positive cells data. | | | | | | |
|---|---|---|---|---|---|---|---|
| | IFN-γ | IL-17 | IFN-γ/IL-17 | IL-22 | IL-10 | IL-9 | IL-4 |
| A50 | 0.00317 | 0.012647 | 0.055607 | 0.028488 | 0.12169 | 0.059027 | 0.772352 |
| AG | 0.036243 | 0.462057 | 0.909833 | 0.167452 | 0.262387 | 0.213291 | 0.291673 |

Example 19: Effect of Pre-Treatment of Beta-1,3-Glucan Derived from *Euglena* on T Helper Cell Cytokine Profile in Mice with Chemically Induced Acute Colitis Mice with chemically-induced acute colitis were treated as described in Example 12. Cytokine production by colonic immune cells was analyzed in individual mice on Day 10 (3 mice/treatment group). Immune cells were isolated from colon tissues using magnetic separation, and equal numbers of cells from each mouse were cultured for 24 hours. The levels of spontaneously released cytokine (T helper cell specific) were determined using a multiplex assay in triplicate (FIG. 20).

The data show that Th 1 (IFN-γ) and Th17 (IL-17) cytokines were suppressed in mice treated with dried *Euglena* biomass. Higher levels of both pro-inflammatory (IL-22, IL-9 (Th9)) and anti-inflammatory (IL-10, IL-4 (Th2)) cytokines were produced by colonic immune cells in mice treated with purified beta-1,3-glucan. The particularly pronounced protection of mice from colitis by treatment with dried *Euglena* biomass appears to be due to increased production of cytokine IL-10 and inhibition of pro-inflammatory immune cell recruitment.

Example 20: Clinical Study to Assess the Effect of Consuming Beta-1,3-Glucan Derived from *Euglena* on Intestinal Inflammation in Individuals A clinical trial is used to evaluate the effects of consuming beta-1,3-glucan derived from *Euglena* on treating intestinal inflammation. Participants are recruited after providing written informed consent (as approved by a registered Institutional Review Board) and a screening process. The study is 4 weeks in duration and evaluations take place at baseline, 2, and 4 weeks of beta-1,3-glucan consumption. Beta-1,3-glucan derived from *Euglena* is administered in capsule form to provide a daily dose of 250 mg to each individual.

The effect of beta glucan on intestinal inflammation is measured using one or more of the following: degree of abdominal pain, occurrence of diarrhea, body weight, level of appetite, presence of rectal bleeding, evaluation of general health and wellness, and determination of blood pressure and blood chemistry. Analysis of blood chemistry can include protein carbonyl content (a marker for oxidative stress), acute phase inflammatory markers (such as C-reactive protein, alpha-1 acid glycoprotein, fibrinogen, and platelet factor-4), cytokine panel, and antibody analysis.

Oral consumption of beta-1,3-glucan derived from *Euglena* reduces the number of inflammatory basophils in an individual, as shown in FIG. 21. This data demonstrates that beta-1,3-glucan derived from *Euglena* modulates the immune system function of an individual.

Oral consumption of beta-1,3-glucan derived from *Euglena* affects the number of urgent bowel movements or diarrhea in an individual, as shown in FIG. 22. The data indicates a statistically significant decrease in bowel problems from 0-2 weeks ($p<0.05$, *), and an increase in bowel problems from 2-4 weeks, reaching a statistical trend ($p<0.1$, (*)). This data demonstrates that beta-1,3-glucan derived from *Euglena* plays a role in the health of an individual's intestine.

Oral consumption of beta-1,3-glucan derived from *Euglena* also modulates an individual's response to oxidative stress, which may play a role in inflammation. Superoxide Dismutase (SOD) is an enzyme that participates in neutralizing superoxide ions, which are highly reactive and damaging free radicals. SOD plays a critical role in reducing oxidative stress. Oral consumption of beta-1,3-glucan derived from *Euglena* increases the level of SOD in an individual, as shown in FIG. 23. During the first 2 weeks of oral consumption of beta-1,3-glucan derived from *Euglena*, a significant increase in the average SOD level was seen, followed by a mild decrease during the next two weeks. Despite the mild decrease over the last two weeks of the study, the overall improvement across the 4 weeks was highly significant ($p<0.01$, **) for all participants.

Another measure for free radical stress in the body is lipid peroxidation. Lipid peroxidation is one of the main mechanisms of cellular damage induced by oxidative stress. Specifically, malondialdehyde is a marker for free radical stress in the body, and a measure of oxidative damage to lipids in the blood stream. During the first 2 weeks of oral consumption of beta-1,3-glucan derived from *Euglena*, a significant reduction in lipid peroxidation was seen, followed by a mild increase during the next two weeks (FIG. 24). Despite the mild increase over the last two weeks of the study, the overall improvement across the 4 weeks was highly significant ($p<0.01$, **).

The above description includes several numerical ranges in the text and figures. The numerical ranges support any range or value within the disclosed numerical ranges even though a precise range limitation is not stated verbatim in the specification because embodiments of the invention can be practiced throughout the disclosed numerical ranges.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. The entire disclosure of the patents and publications referred to in this application are hereby incorporated herein by reference. Finally, the invention can be construed according to the claims and their equivalents.

What is claimed is:

1. A method of treating a condition selected from the group consisting of hyperlipidemia, metabolic syndrome, inflammatory bowel disease, colitis, Crohn's disease in a human with said condition, the method comprising orally administering to the human an effective amount of a composition comprising beta-1,3-glucan from *Euglena* grown using fermentation and dried to contain less than 10% moisture, said beta-1,3-glucan having no beta-1,6-glycosidic bonds, wherein the effective amount of the composition comprises between 0.1 mg beta-1,3-glucan/kg body weight and 100 mg beta-1,3-glucan/kg body weight.

2. The method of claim 1, wherein the condition is hyperlipidemia.

3. The method of claim 2, wherein administration of the composition reduces the level of cholesterol in the human.

4. The method of claim 2, wherein the composition is administered in combination with statins, nicotinic acid, bile acid resins, fibric acid derivatives, or cholesterol absorption inhibitors.

5. The method of claim 1, wherein the condition is selected from the group consisting of inflammatory bowel disease, colitis, and Crohn's disease.

6. The method of claim 1, wherein the condition is selected from the group consisting of inflammatory bowel disease, colitis, and Crohn's disease.

7. The method of claim 5, wherein the condition is colitis.

8. The method of claim 5, wherein the condition is inflammatory bowel disease.

9. The method of claim 5, wherein the condition is Crohn's disease.

10. The method of claim 5, wherein the effective amount of the composition comprises between 0.1 mg beta-1,3-glucan/kg body weight and 100 mg beta-1,3-glucan/kg body weight.

11. The method of claim 5, wherein administering the composition increases anti-inflammatory cytokine production.

12. The method of claim 5, wherein the composition is administered in combination with anti-inflammatory drugs, immunosuppression drugs, or antibiotics.

13. The method of claim 1, wherein the *Euglena* is *Euglena gracilis*.

14. The method of claim 1, wherein the *Euglena* is heterotrophically grown.

15. The method of claim 1, wherein the beta-1,3-glucan is in the form of paramylon.

16. The method of claim 1, wherein the beta-1,3-glucan is purified from *Euglena*.

17. The method of claim 1, wherein the composition comprises *Euglena* biomass, the *Euglena* biomass comprising the beta-1,3-glucan.

18. The method of claim 17, wherein the *Euglena* biomass has been further processed to have an average particle size of 1000 microns or less.

19. The method of claim 1, wherein the composition is administered daily as a single dose.

20. The method of claim 1, wherein the composition is administered as multiple separate doses in a single day.

21. The method of claim 1, wherein the composition further comprises an additional component selected from the group consisting of alpha tocopherol, cholecalciferol, zinc, chromium, selenium, arginine, ascorbic acid, alkylglycerol, caffeine, kava kava, *Curcuma longa, Spirulina*, Chlorella, *stevia*, calcium D-glucarate, coenzyme Q10, peptides, dimethylglycine, docosahexaenoic acid, eicosapentaenoic acid, alpha-lineolenic acid, astaxanthin, beta carotene, lutein, *lactobacillus* probiotics, *bifidobacterium* probiotics, mannoligosaccharide, fructooligosaccharides, *Astragalus, Echinacea*, Esberitox, garlic, glutathione, kelp, L-arginine, L-ornithine, lecithin granules, extracts from maiitake, reishi or shiitake mushrooms, manganese, quercetin, bromelain, Olive Leaf, *Sambucus*, Umcka, panthothenic acid, quercetin, alpha lipoic acid, essential oils, fish oils, spices and their derivatives, pterostilbene, and combinations thereof.

22. The method of claim 1, wherein the composition further comprises an additional component selected from the group consisting of *Haematococcus pluvialis*, astaxanthin, and colostrum.

23. The method of claim 1, wherein the composition is administered as a solid.

24. The method of claim 1, wherein the composition is administered as a suspension.

25. The method of claim 1, whereby the effective amount of the composition comprises between 0.1 mg beta-1,3 glucan/kg body weight and 50 mg beta-1,3 glucan/kg body weight.

* * * * *